(12) United States Patent
Lin et al.

(10) Patent No.: US 10,407,673 B2
(45) Date of Patent: Sep. 10, 2019

(54) METHODS FOR GLYCOPROTEIN REMODELING USING ENDOGLYCOSIDASE MUTANTS

(71) Applicants: CHO Pharma Inc., Taipei (TW); Academia Sinica, Taipei (TW)

(72) Inventors: Nan-Horng Lin, Vernon Hills, IL (US); Lin-Ya Huang, New Taipei (TW); Sachin S Shivatare, Taipei (TW); Li-Tzu Chen, Taipei (TW); Chi-Huey Wong, Taipei (TW); Chung-Yi Wu, New Taipei (TW); Ting Cheng, Keelung (TW)

(73) Assignees: CHO Pharma Inc., Taipei (TW); Academia Sinica, Taipei (TW)

( * ) Notice: Subject to any disclaimer, the term of this patent is extended or adjusted under 35 U.S.C. 154(b) by 0 days.

(21) Appl. No.: 16/011,622

(22) Filed: Jun. 18, 2018

(65) Prior Publication Data

US 2018/0298361 A1    Oct. 18, 2018

Related U.S. Application Data

(62) Division of application No. 15/684,897, filed on Aug. 23, 2017, now Pat. No. 10,000,747.

(60) Provisional application No. 62/378,806, filed on Aug. 24, 2016.

(51) Int. Cl.
*C12N 9/42* (2006.01)
*C12P 21/00* (2006.01)
*C07K 16/28* (2006.01)

(52) U.S. Cl.
CPC ........ *C12N 9/2434* (2013.01); *C07K 16/2887* (2013.01); *C12P 21/005* (2013.01); *C12Y 302/01096* (2013.01); *C07K 2317/24* (2013.01); *C07K 2317/41* (2013.01); *C07K 2317/732* (2013.01); *C07K 2319/21* (2013.01)

(58) Field of Classification Search
None
See application file for complete search history.

(56) References Cited

U.S. PATENT DOCUMENTS 9,493,752 B2 * 11/2016 Collin ............ C12Y 302/01096

OTHER PUBLICATIONS

Sjogren et al. (Biochem. J. (2013) 455, 107-118).*
Li et al. (The Journal of Biological Chemistry vol. 291, No. 32, pp. 16508-16518, Aug. 5, 2016).*

* cited by examiner

*Primary Examiner* — Suzanne M Noakes
*Assistant Examiner* — Jae W Lee
(74) *Attorney, Agent, or Firm* — Liang Legal Group, PLLC

(57) ABSTRACT

A mutant of EndoS2 includes one or more mutations in the sequence of a wild-type EndoS2 (SEQ ID NO:1), wherein the one or more mutations are in a peptide region located within residues 133-143, residues 177-182, residues 184-189, residues 221-231, and/or residues 227-237, wherein the mutant of EndoS2 has a low hydrolyzing activity and a high tranglycosylation activity, as compared to those of the wild-type EndoS2. A method for preparing an engineered glycoprotein using the mutant of EndoS2 includes coupling an activated oligosaccharide to a glycoprotein acceptor. The activated oligosaccharide is a glycan oxazoline.

12 Claims, 11 Drawing Sheets

Specification includes a Sequence Listing.

Figure 1

```
  1  MKKLLVKRILGCVDAATLMGAALATHRDSLRTYKASEKTVQTGKTDQQVGAKLVQEIREDKRGPLYAGYFRTWHDKAST  80
 81  GIDGKQQHPENTMAEVPKEVDILFVPHDRTASDSPFWSELKDSYVHKLHQQGTALVQITGVNELNGRTGLSKDYPDTPEG 160
161  NKALAAAIVKAFVTRGVDKLEDIBHEFTWKRTPEEDARALNVFKEIAQLIGKKGSDKSKLLINHILSVENSPIFKGI   240
241  AKELDYLLAQYTGSQGGEAEVETIRSDSKQYQNYIDASQFMIGFGFFEESASKGNLWFDVNKYDPNNPEKGKDIEGTRAK 320
321  KYAEKQPSTGGLKASIFSYAIDRKGVAHVFSTYKNRTSTRLQKHEVDNISHTDYTVSRKLKTLMTEDKRYGVIDQKGIPD 400
401  FALREQIIQQVGQYKGDLEKYRKTLVLJGDKIQNLRGLEKLSKLQRLELAQLSNVYKEITPELLPESRKDAELVMVGNTG 480
481  LEKLKLSGLRPQTLGGIDVNGITKLTSFGISHNSLRLSEKGEDPKLLKTLMEQVGNHQKITVENTAFERQKPKGTYPQTY 560
561  DTKEGRYDVRKEHDILTDFVFGTVTKANTFIGDKKAFAIYKEGAVDGRQYVSKDYTFEAFRKDYKGYKVRLTASRLGET  640
641  VTSKVTATTDETYLVDVSGGBKVVHKWKLNIGGGRIMMEBLAKGAKVIGTGGDFEQAKKIFDGEKSDRFFTWGQTNKIAF 720
721  DLGRINLAKEWRLFRAETNTEIRTDSSINVAKGRLQILKDTTIDLERKDIKNRKEYLSNDENWTDVAQMDDAKAIFNSKL 800
801  SNVLSPYWRFCVDGGAESYYPQYTELQILQQRLSNDVAPTLKD 843
```

Figure 2

M : Marker
Lane 1 : Commercial Rituximab
Lane 2 : GlcNAc-Rituximab
Lane 3 : Rtx-G1
Lane 4 : Rtx-G2
Lane 5 : Rtx-G3
Lane 6 : Rtx-G4
Lane 7 : Rtx-G5

M : Marker
Lane 1 : Commercial Rituximab
Lane 2 : GlcNAc-Rituximab
Lane 3 : Rtx-G6
Lane 4 : Rtx-G7
Lane 5 : Rtx-G8
Lane 6 : Rtx-G9
Lane 7 : Rtx-G10

M : Marker
Lane 1 : Commercial Rituximab
Lane 2 : GlcNAc-Rituximab
Lane 3 : Rtx-G11
Lane 4 : Rtx-G12
Lane 5 : Rtx-G13
Lane 6 : Rtx-G14
Lane 7 : Rtx-G15
Lane 8 : Rtx-G16

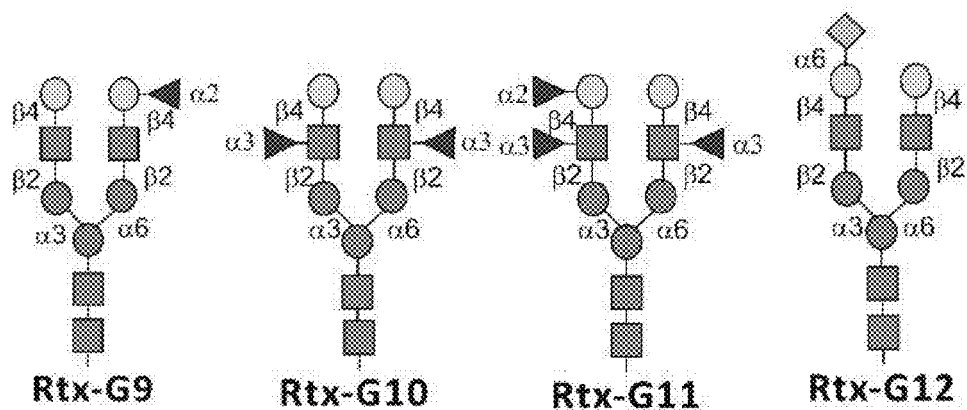
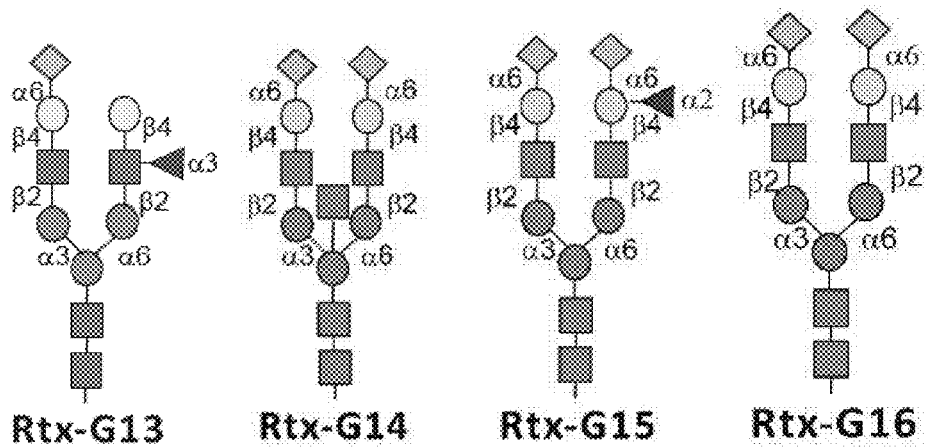
Figure 15 (Continued)

SEQUENCE LISTING

<160> NUMBER OF SEQ ID NOS: 19

<210> SEQ ID NO 1
<211> LENGTH: 842
<212> TYPE: PRT
<213> ORGANISM: Streptococcus pyogenes

<400> SEQUENCE: 1

```
Met Asp Lys His Leu Leu Val Lys Arg Thr Leu Gly Cys Val Cys Ala
 1               5                  10                  15

Ala Thr Leu Met Gly Ala Ala Leu Ala Thr His His Asp Ser Leu Asn
                20                  25                  30

Thr Val Lys Ala Glu Glu Lys Thr Val Gln Thr Gly Lys Thr Asp Gln
            35                  40                  45

Gln Val Gly Ala Lys Leu Val Gln Glu Ile Arg Glu Gly Lys Arg Gly
        50                  55                  60

Pro Leu Tyr Ala Gly Tyr Phe Arg Thr Trp His Asp Arg Ala Ser Thr
65                  70                  75                  80

Gly Ile Asp Gly Lys Gln Gln His Pro Glu Asn Thr Met Ala Glu Val
                85                  90                  95

Pro Lys Glu Val Asp Ile Leu Phe Val Phe His Asp His Thr Ala Ser
            100                 105                 110

Asp Ser Pro Phe Trp Ser Glu Leu Lys Asp Ser Tyr Val His Lys Leu
        115                 120                 125

His Gln Gln Gly Thr Ala Leu Val Gln Thr Ile Gly Val Asn Glu Leu
    130                 135                 140

Asn Gly Arg Thr Gly Leu Ser Lys Asp Tyr Pro Asp Thr Pro Glu Gly
145                 150                 155                 160

Asn Lys Ala Leu Ala Ala Ile Val Lys Ala Phe Val Thr Asp Arg
                165                 170                 175

Gly Val Asp Gly Leu Asp Ile Asp Ile Glu His Glu Phe Thr Asn Lys
            180                 185                 190

Arg Thr Pro Glu Glu Asp Ala Arg Ala Leu Asn Val Phe Lys Glu Ile
        195                 200                 205

Ala Gln Leu Ile Gly Lys Asn Gly Ser Asp Lys Ser Lys Leu Leu Ile
    210                 215                 220

Met Asp Thr Thr Leu Ser Val Glu Asn Asn Pro Ile Phe Lys Gly Ile
225                 230                 235                 240

Ala Glu Asp Leu Asp Tyr Leu Leu Arg Gln Tyr Tyr Gly Ser Gln Gly
                245                 250                 255

Gly Glu Ala Glu Val Asp Thr Ile Asn Ser Asp Trp Asn Gln Tyr Gln
            260                 265                 270

Asn Tyr Ile Asp Ala Ser Gln Phe Met Ile Gly Phe Ser Phe Glu
        275                 280                 285

Glu Ser Ala Ser Lys Gly Asn Leu Trp Phe Asp Val Asn Glu Tyr Asp
    290                 295                 300

Pro Asn Asn Pro Glu Lys Gly Lys Asp Ile Glu Gly Thr Arg Ala Lys
305                 310                 315                 320

Lys Tyr Ala Glu Trp Gln Pro Ser Thr Gly Gly Leu Lys Ala Gly Ile
                325                 330                 335

Phe Ser Tyr Ala Ile Asp Arg Asp Gly Val Ala His Val Pro Ser Thr
            340                 345                 350

Tyr Lys Asn Arg Thr Ser Thr Asn Leu Gln Arg His Glu Val Asp Asn
        355                 360                 365
```

```
Ile Ser His Thr Asp Tyr Thr Val Ser Arg Lys Leu Lys Thr Leu Met
370                 375                 380

Thr Glu Asp Lys Arg Tyr Asp Val Ile Asp Gln Lys Asp Ile Pro Asp
385                 390                 395                 400

Pro Ala Leu Arg Glu Gln Ile Ile Gln Gln Val Gly Gln Tyr Lys Gly
                405                 410                 415

Asp Leu Glu Arg Tyr Asn Lys Thr Leu Val Leu Thr Gly Asp Lys Ile
                420                 425                 430

Gln Asn Leu Lys Gly Leu Glu Leu Ser Lys Leu Gln Lys Leu Glu
                435                 440                 445

Leu Arg Gln Leu Ser Asn Val Lys Glu Ile Thr Pro Glu Leu Leu Pro
450                 455                 460

Glu Ser Met Lys Lys Asp Ala Glu Leu Val Met Val Gly Met Thr Gly
465                 470                 475                 480

Leu Glu Lys Leu Asn Leu Ser Gly Leu Asn Arg Gln Thr Leu Asp Gly
                485                 490                 495

Ile Asp Val Asn Ser Ile Thr His Leu Thr Ser Phe Asp Ile Ser His
                500                 505                 510

Asn Ser Leu Asp Leu Ser Glu Lys Ser Glu Asp Arg Lys Leu Leu Met
                515                 520                 525

Thr Leu Met Glu Gln Val Ser Asn His Gln Lys Ile Thr Val Lys Asn
530                 535                 540

Thr Ala Phe Glu Asn Gln Lys Pro Lys Gly Tyr Tyr Pro Gln Thr Tyr
545                 550                 555                 560

Asp Thr Lys Glu Gly His Tyr Asp Val Asp Asn Ala Glu His Asp Ile
                565                 570                 575

Leu Thr Asp Phe Val Phe Gly Thr Val Thr Lys Arg Asn Thr Phe Ile
                580                 585                 590

Gly Asp Glu Glu Ala Phe Ala Ile Tyr Lys Glu Gly Ala Val Asp Gly
                595                 600                 605

Arg Gln Tyr Val Ser Lys Asp Tyr Thr Tyr Glu Ala Phe Arg Lys Asp
                610                 615                 620

Tyr Lys Gly Tyr Lys Val His Leu Thr Ala Ser Asn Leu Gly Glu Thr
625                 630                 635                 640

Val Thr Ser Lys Val Thr Ala Thr Thr Asp Glu Thr Tyr Leu Val Asp
                645                 650                 655

Val Ser Asp Gly Glu Lys Val Val His His Met Lys Leu Asn Ile Gly
                660                 665                 670

Ser Gly Ala Ile Met Met Glu Asn Leu Ala Lys Gly Ala Lys Val Ile
                675                 680                 685

Gly Thr Ser Gly Asp Phe Glu Gln Ala Lys Lys Ile Phe Asp Gly Glu
                690                 695                 700

Lys Ser Asp Arg Phe Phe Thr Trp Gly Gln Thr Asn Trp Ile Ala Phe
705                 710                 715                 720

Asp Leu Gly Glu Ile Asn Leu Ala Lys Glu Trp Arg Leu Phe Asn Ala
                725                 730                 735

Glu Thr Asn Thr Glu Ile Lys Thr Asp Ser Ser Leu Asn Val Ala Lys
                740                 745                 750

Gly Arg Leu Gln Ile Leu Lys Asp Thr Thr Ile Asp Leu Glu Lys Met
                755                 760                 765

Asp Ile Lys Asn Arg Lys Glu Tyr Leu Ser Asn Asp Glu Asn Trp Thr
770                 775                 780

Asp Val Ala Gln Met Asp Asp Ala Lys Ala Ile Phe Asn Ser Lys Leu
```

```
                        785                 790                 795                 800
Ser Asn Val Leu Ser Arg Tyr Trp Arg Phe Cys Val Asp Gly Gly Ala
                805                 810                 815

Ser Ser Tyr Tyr Pro Gln Tyr Thr Glu Leu Gln Ile Leu Gly Gln Arg
                820                 825                 830

Leu Ser Asn Asp Val Ala Asn Thr Leu Asp
                835                 840

<210> SEQ ID NO 2
<211> LENGTH: 842
<212> TYPE: PRT
<213> ORGANISM: Artificial Sequence
<220> FEATURE:
<223> OTHER INFORMATION: Synthetic

<400> SEQUENCE: 2

Met Asp Lys His Leu Leu Val Lys Arg Thr Leu Gly Cys Val Cys Ala
1               5                   10                  15

Ala Thr Leu Met Gly Ala Ala Leu Ala Thr His His Asp Ser Leu Asn
                20                  25                  30

Thr Val Lys Ala Glu Glu Lys Thr Val Gln Thr Gly Lys Thr Asp Gln
            35                  40                  45

Gln Val Gly Ala Lys Leu Val Gln Glu Ile Arg Glu Gly Lys Arg Gly
        50                  55                  60

Pro Leu Tyr Ala Gly Tyr Phe Arg Thr Trp His Asp Arg Ala Ser Thr
65                  70                  75                  80

Gly Ile Asp Gly Lys Gln Gln His Pro Glu Asn Thr Met Ala Glu Val
                85                  90                  95

Pro Lys Glu Val Asp Ile Leu Phe Val Phe His Asp His Thr Ala Ser
            100                 105                 110

Asp Ser Pro Phe Trp Ser Glu Leu Lys Asp Ser Tyr Val His Lys Leu
        115                 120                 125

His Gln Gln Gly Thr Ala Leu Val Gln Thr Ile Gly Val Asn Glu Leu
    130                 135                 140

Asn Gly Arg Thr Gly Leu Ser Lys Asp Tyr Pro Asp Thr Pro Glu Gly
145                 150                 155                 160

Asn Lys Ala Leu Ala Ala Ala Ile Val Lys Ala Phe Val Thr Asp Arg
                165                 170                 175

Gly Val Asp Gly Leu Gln Ile Asp Ile Glu His Glu Phe Thr Asn Lys
            180                 185                 190

Arg Thr Pro Glu Glu Asp Ala Arg Ala Leu Asn Val Phe Lys Glu Ile
        195                 200                 205

Ala Gln Leu Ile Gly Lys Asn Gly Ser Asp Lys Ser Lys Leu Leu Ile
    210                 215                 220

Met Asp Thr Thr Leu Ser Val Glu Asn Asn Pro Ile Phe Lys Gly Ile
225                 230                 235                 240

Ala Glu Asp Leu Asp Tyr Leu Leu Arg Gln Tyr Tyr Gly Ser Gln Gly
                245                 250                 255

Gly Glu Ala Glu Val Asp Thr Ile Asn Ser Asp Trp Asn Gln Tyr Gln
            260                 265                 270

Asn Tyr Ile Asp Ala Ser Gln Phe Met Ile Gly Phe Ser Phe Phe Glu
        275                 280                 285

Glu Ser Ala Ser Lys Gly Asn Leu Trp Phe Asp Val Asn Glu Tyr Asp
    290                 295                 300

Pro Asn Asn Pro Glu Lys Gly Lys Asp Ile Glu Gly Thr Arg Ala Lys
```

-continued

```
            305                 310                 315                 320
Lys Tyr Ala Glu Trp Gln Pro Ser Thr Gly Gly Leu Lys Ala Gly Ile
                325                 330                 335

Phe Ser Tyr Ala Ile Asp Arg Asp Gly Val Ala His Val Pro Ser Thr
                340                 345                 350

Tyr Lys Asn Arg Thr Ser Thr Asn Leu Gln Arg His Glu Val Asp Asn
                355                 360                 365

Ile Ser His Thr Asp Tyr Thr Val Ser Arg Lys Leu Lys Thr Leu Met
370                 375                 380

Thr Glu Asp Lys Arg Tyr Asp Val Ile Asp Gln Lys Asp Ile Pro Asp
385                 390                 395                 400

Pro Ala Leu Arg Glu Gln Ile Ile Gln Gln Val Gly Gln Tyr Lys Gly
                405                 410                 415

Asp Leu Glu Arg Tyr Asn Lys Thr Leu Val Leu Thr Gly Asp Lys Ile
                420                 425                 430

Gln Asn Leu Lys Gly Leu Glu Lys Leu Ser Lys Leu Gln Lys Leu Glu
                435                 440                 445

Leu Arg Gln Leu Ser Asn Val Lys Glu Ile Thr Pro Glu Leu Leu Pro
450                 455                 460

Glu Ser Met Lys Lys Asp Ala Glu Leu Val Met Val Gly Met Thr Gly
465                 470                 475                 480

Leu Glu Lys Leu Asn Leu Ser Gly Leu Asn Arg Gln Thr Leu Asp Gly
                485                 490                 495

Ile Asp Val Asn Ser Ile Thr His Leu Thr Ser Phe Asp Ile Ser His
                500                 505                 510

Asn Ser Leu Asp Leu Ser Glu Lys Ser Glu Asp Arg Lys Leu Leu Met
                515                 520                 525

Thr Leu Met Glu Gln Val Ser Asn His Gln Lys Ile Thr Val Lys Asn
                530                 535                 540

Thr Ala Phe Glu Asn Gln Lys Pro Lys Gly Tyr Tyr Pro Gln Thr Tyr
545                 550                 555                 560

Asp Thr Lys Glu Gly His Tyr Asp Val Asp Asn Ala Glu His Asp Ile
                565                 570                 575

Leu Thr Asp Phe Val Phe Gly Thr Val Thr Lys Arg Asn Thr Phe Ile
                580                 585                 590

Gly Asp Glu Glu Ala Phe Ala Ile Tyr Lys Glu Gly Ala Val Asp Gly
                595                 600                 605

Arg Gln Tyr Val Ser Lys Asp Tyr Thr Tyr Glu Ala Phe Arg Lys Asp
                610                 615                 620

Tyr Lys Gly Tyr Lys Val His Leu Thr Ala Ser Asn Leu Gly Glu Thr
625                 630                 635                 640

Val Thr Ser Lys Val Thr Ala Thr Thr Asp Glu Thr Tyr Leu Val Asp
                645                 650                 655

Val Ser Asp Gly Glu Lys Val Val His His Met Lys Leu Asn Ile Gly
                660                 665                 670

Ser Gly Ala Ile Met Met Glu Asn Leu Ala Lys Gly Ala Lys Val Ile
                675                 680                 685

Gly Thr Ser Gly Asp Phe Glu Gln Ala Lys Lys Ile Phe Asp Gly Glu
                690                 695                 700

Lys Ser Asp Arg Phe Phe Thr Trp Gly Gln Thr Asn Trp Ile Ala Phe
705                 710                 715                 720

Asp Leu Gly Glu Ile Asn Leu Ala Lys Glu Trp Arg Leu Phe Asn Ala
                725                 730                 735
```

Glu Thr Asn Thr Glu Ile Lys Thr Asp Ser Ser Leu Asn Val Ala Lys
                740                 745                 750

Gly Arg Leu Gln Ile Leu Lys Asp Thr Thr Ile Asp Leu Glu Lys Met
            755                 760                 765

Asp Ile Lys Asn Arg Lys Glu Tyr Leu Ser Asn Asp Glu Asn Trp Thr
770                 775                 780

Asp Val Ala Gln Met Asp Asp Ala Lys Ala Ile Phe Asn Ser Lys Leu
785                 790                 795                 800

Ser Asn Val Leu Ser Arg Tyr Trp Arg Phe Cys Val Asp Gly Gly Ala
                805                 810                 815

Ser Ser Tyr Tyr Pro Gln Tyr Thr Glu Leu Gln Ile Leu Gly Gln Arg
            820                 825                 830

Leu Ser Asn Asp Val Ala Asn Thr Leu Asp
            835                 840

<210> SEQ ID NO 3
<211> LENGTH: 842
<212> TYPE: PRT
<213> ORGANISM: Artificial Sequence
<220> FEATURE:
<223> OTHER INFORMATION: Synthetic

<400> SEQUENCE: 3

Met Asp Lys His Leu Leu Val Lys Arg Thr Leu Gly Cys Val Cys Ala
1               5                   10                  15

Ala Thr Leu Met Gly Ala Ala Leu Ala Thr His His Asp Ser Leu Asn
                20                  25                  30

Thr Val Lys Ala Glu Glu Lys Thr Val Gln Thr Gly Lys Thr Asp Gln
            35                  40                  45

Gln Val Gly Ala Lys Leu Val Gln Glu Ile Arg Glu Gly Lys Arg Gly
        50                  55                  60

Pro Leu Tyr Ala Gly Tyr Phe Arg Thr Trp His Asp Arg Ala Ser Thr
65                  70                  75                  80

Gly Ile Asp Gly Lys Gln Gln His Pro Glu Asn Thr Met Ala Glu Val
                85                  90                  95

Pro Lys Glu Val Asp Ile Leu Phe Val Phe His Asp His Thr Ala Ser
                100                 105                 110

Asp Ser Pro Phe Trp Ser Glu Leu Lys Asp Ser Tyr Val His Lys Leu
            115                 120                 125

His Gln Gln Gly Thr Ala Leu Val Gln Thr Ile Gly Val Asn Glu Leu
        130                 135                 140

Asn Gly Arg Thr Gly Leu Ser Lys Asp Tyr Pro Asp Thr Pro Glu Gly
145                 150                 155                 160

Asn Lys Ala Leu Ala Ala Ile Val Lys Ala Phe Val Thr Asp Arg
                165                 170                 175

Gly Val Asp Gly Leu Asp Ile Asp Ile Glu His Glu Phe Thr Asn Lys
            180                 185                 190

Arg Thr Pro Glu Glu Asp Ala Arg Ala Leu Asn Val Phe Lys Glu Ile
        195                 200                 205

Ala Gln Leu Ile Gly Lys Asn Gly Ser Asp Lys Ser Lys Leu Leu Ile
    210                 215                 220

Met Gln Thr Thr Leu Ser Val Glu Asn Asn Pro Ile Phe Lys Gly Ile
225                 230                 235                 240

Ala Glu Asp Leu Asp Tyr Leu Leu Arg Gln Tyr Tyr Gly Ser Gln Gly
                245                 250                 255

```
Gly Glu Ala Glu Val Asp Thr Ile Asn Ser Asp Trp Asn Gln Tyr Gln
            260                 265                 270

Asn Tyr Ile Asp Ala Ser Gln Phe Met Ile Gly Phe Ser Phe Phe Glu
            275                 280                 285

Glu Ser Ala Ser Lys Gly Asn Leu Trp Phe Asp Val Asn Glu Tyr Asp
290                 295                 300

Pro Asn Asn Pro Glu Lys Gly Lys Asp Ile Glu Gly Thr Arg Ala Lys
305                 310                 315                 320

Lys Tyr Ala Glu Trp Gln Pro Ser Thr Gly Gly Leu Lys Ala Gly Ile
                325                 330                 335

Phe Ser Tyr Ala Ile Asp Arg Asp Gly Val Ala His Val Pro Ser Thr
            340                 345                 350

Tyr Lys Asn Arg Thr Ser Thr Asn Leu Gln Arg His Glu Val Asp Asn
            355                 360                 365

Ile Ser His Thr Asp Tyr Thr Val Ser Arg Lys Leu Lys Thr Leu Met
            370                 375                 380

Thr Glu Asp Lys Arg Tyr Asp Val Ile Asp Gln Lys Asp Ile Pro Asp
385                 390                 395                 400

Pro Ala Leu Arg Glu Gln Ile Ile Gln Gln Val Gly Gln Tyr Lys Gly
                405                 410                 415

Asp Leu Glu Arg Tyr Asn Lys Thr Leu Val Leu Thr Gly Asp Lys Ile
            420                 425                 430

Gln Asn Leu Lys Gly Leu Glu Lys Leu Ser Lys Leu Gln Lys Leu Glu
            435                 440                 445

Leu Arg Gln Leu Ser Asn Val Lys Glu Ile Thr Pro Glu Leu Leu Pro
450                 455                 460

Glu Ser Met Lys Lys Asp Ala Glu Leu Val Met Val Gly Met Thr Gly
465                 470                 475                 480

Leu Glu Lys Leu Asn Leu Ser Gly Leu Asn Arg Gln Thr Leu Asp Gly
                485                 490                 495

Ile Asp Val Asn Ser Ile Thr His Leu Thr Ser Phe Asp Ile Ser His
            500                 505                 510

Asn Ser Leu Asp Leu Ser Glu Lys Ser Glu Asp Arg Lys Leu Leu Met
            515                 520                 525

Thr Leu Met Glu Gln Val Ser Asn His Gln Lys Ile Thr Val Lys Asn
530                 535                 540

Thr Ala Phe Glu Asn Gln Lys Pro Lys Gly Tyr Tyr Pro Gln Thr Tyr
545                 550                 555                 560

Asp Thr Lys Glu Gly His Tyr Asp Val Asp Asn Ala Glu His Asp Ile
                565                 570                 575

Leu Thr Asp Phe Val Phe Gly Thr Val Thr Lys Arg Asn Thr Phe Ile
            580                 585                 590

Gly Asp Glu Glu Ala Phe Ala Ile Tyr Lys Glu Gly Ala Val Asp Gly
            595                 600                 605

Arg Gln Tyr Val Ser Lys Asp Tyr Thr Tyr Glu Ala Phe Arg Lys Asp
610                 615                 620

Tyr Lys Gly Tyr Lys Val His Leu Thr Ala Ser Asn Leu Gly Glu Thr
625                 630                 635                 640

Val Thr Ser Lys Val Thr Ala Thr Thr Asp Glu Thr Tyr Leu Val Asp
                645                 650                 655

Val Ser Asp Gly Glu Lys Val Val His His Met Lys Leu Asn Ile Gly
            660                 665                 670
```

```
Ser Gly Ala Ile Met Met Glu Asn Leu Ala Lys Gly Ala Lys Val Ile
            675                 680                 685

Gly Thr Ser Gly Asp Phe Glu Gln Ala Lys Lys Ile Phe Asp Gly Glu
    690                 695                 700

Lys Ser Asp Arg Phe Phe Thr Trp Gly Gln Thr Asn Trp Ile Ala Phe
705                 710                 715                 720

Asp Leu Gly Glu Ile Asn Leu Ala Lys Glu Trp Arg Leu Phe Asn Ala
                725                 730                 735

Glu Thr Asn Thr Glu Ile Lys Thr Asp Ser Ser Leu Asn Val Ala Lys
            740                 745                 750

Gly Arg Leu Gln Ile Leu Lys Asp Thr Thr Ile Asp Leu Glu Lys Met
    755                 760                 765

Asp Ile Lys Asn Arg Lys Glu Tyr Leu Ser Asn Asp Glu Asn Trp Thr
770                 775                 780

Asp Val Ala Gln Met Asp Asp Ala Lys Ala Ile Phe Asn Ser Lys Leu
785                 790                 795                 800

Ser Asn Val Leu Ser Arg Tyr Trp Arg Phe Cys Val Asp Gly Gly Ala
                805                 810                 815

Ser Ser Tyr Tyr Pro Gln Tyr Thr Glu Leu Gln Ile Leu Gly Gln Arg
            820                 825                 830

Leu Ser Asn Asp Val Ala Asn Thr Leu Asp
            835                 840

<210> SEQ ID NO 4
<211> LENGTH: 842
<212> TYPE: PRT
<213> ORGANISM: Artificial Sequence
<220> FEATURE:
<223> OTHER INFORMATION: Synthetic

<400> SEQUENCE: 4

Met Asp Lys His Leu Leu Val Lys Arg Thr Leu Gly Cys Val Cys Ala
1               5                   10                  15

Ala Thr Leu Met Gly Ala Ala Leu Ala Thr His His Asp Ser Leu Asn
            20                  25                  30

Thr Val Lys Ala Glu Glu Lys Thr Val Gln Thr Gly Lys Thr Asp Gln
        35                  40                  45

Gln Val Gly Ala Lys Leu Val Gln Glu Ile Arg Glu Gly Lys Arg Gly
    50                  55                  60

Pro Leu Tyr Ala Gly Tyr Phe Arg Thr Trp His Asp Arg Ala Ser Thr
65                  70                  75                  80

Gly Ile Asp Gly Lys Gln Gln His Pro Glu Asn Thr Met Ala Glu Val
                85                  90                  95

Pro Lys Glu Val Asp Ile Leu Phe Val Phe His Asp His Thr Ala Ser
            100                 105                 110

Asp Ser Pro Phe Trp Ser Glu Leu Lys Asp Ser Tyr Val His Lys Leu
        115                 120                 125

His Gln Gln Gly Thr Ala Leu Val Gln Thr Ile Gly Val Asn Glu Leu
    130                 135                 140

Asn Gly Arg Thr Gly Leu Ser Lys Asp Tyr Pro Asp Thr Pro Glu Gly
145                 150                 155                 160

Asn Lys Ala Leu Ala Ala Ile Val Lys Ala Phe Val Thr Asp Arg
                165                 170                 175

Gly Val Asp Gly Leu Asp Ile Asp Ile Glu His Glu Phe Thr Asn Lys
            180                 185                 190
```

```
Arg Thr Pro Glu Glu Asp Ala Arg Ala Leu Asn Val Phe Lys Glu Ile
            195                 200                 205

Ala Gln Leu Ile Gly Lys Asn Gly Ser Asp Lys Ser Lys Leu Leu Ile
    210                 215                 220

Met Asp Gln Thr Leu Ser Val Glu Asn Asn Pro Ile Phe Lys Gly Ile
225                 230                 235                 240

Ala Glu Asp Leu Asp Tyr Leu Leu Arg Gln Tyr Tyr Gly Ser Gln Gly
                245                 250                 255

Gly Glu Ala Glu Val Asp Thr Ile Asn Ser Asp Trp Asn Gln Tyr Gln
            260                 265                 270

Asn Tyr Ile Asp Ala Ser Gln Phe Met Ile Gly Phe Ser Phe Phe Glu
        275                 280                 285

Glu Ser Ala Ser Lys Gly Asn Leu Trp Phe Asp Val Asn Glu Tyr Asp
    290                 295                 300

Pro Asn Asn Pro Glu Lys Gly Lys Asp Ile Glu Gly Thr Arg Ala Lys
305                 310                 315                 320

Lys Tyr Ala Glu Trp Gln Pro Ser Thr Gly Gly Leu Lys Ala Gly Ile
                325                 330                 335

Phe Ser Tyr Ala Ile Asp Arg Asp Gly Val Ala His Val Pro Ser Thr
            340                 345                 350

Tyr Lys Asn Arg Thr Ser Thr Asn Leu Gln Arg His Glu Val Asp Asn
        355                 360                 365

Ile Ser His Thr Asp Tyr Thr Val Ser Arg Lys Leu Lys Thr Leu Met
    370                 375                 380

Thr Glu Asp Lys Arg Tyr Asp Val Ile Asp Gln Lys Asp Ile Pro Asp
385                 390                 395                 400

Pro Ala Leu Arg Glu Gln Ile Ile Gln Gln Val Gly Gln Tyr Lys Gly
                405                 410                 415

Asp Leu Glu Arg Tyr Asn Lys Thr Leu Val Leu Thr Gly Asp Lys Ile
            420                 425                 430

Gln Asn Leu Lys Gly Leu Glu Lys Leu Ser Lys Leu Gln Lys Leu Glu
        435                 440                 445

Leu Arg Gln Leu Ser Asn Val Lys Glu Ile Thr Pro Glu Leu Leu Pro
    450                 455                 460

Glu Ser Met Lys Lys Asp Ala Glu Leu Val Met Val Gly Met Thr Gly
465                 470                 475                 480

Leu Glu Lys Leu Asn Leu Ser Gly Leu Asn Arg Gln Thr Leu Asp Gly
                485                 490                 495

Ile Asp Val Asn Ser Ile Thr His Leu Thr Ser Phe Asp Ile Ser His
            500                 505                 510

Asn Ser Leu Asp Leu Ser Glu Lys Ser Glu Asp Arg Lys Leu Leu Met
        515                 520                 525

Thr Leu Met Glu Gln Val Ser Asn His Gln Lys Ile Thr Val Lys Asn
    530                 535                 540

Thr Ala Phe Glu Asn Gln Lys Pro Lys Gly Tyr Tyr Pro Gln Thr Tyr
545                 550                 555                 560

Asp Thr Lys Glu Gly His Tyr Asp Val Asp Asn Ala Glu His Asp Ile
                565                 570                 575

Leu Thr Asp Phe Val Phe Gly Thr Val Thr Lys Arg Asn Thr Phe Ile
            580                 585                 590

Gly Asp Glu Glu Ala Phe Ala Ile Tyr Lys Glu Gly Ala Val Asp Gly
        595                 600                 605

Arg Gln Tyr Val Ser Lys Asp Tyr Thr Tyr Glu Ala Phe Arg Lys Asp
```

```
                    610                 615                 620
Tyr Lys Gly Tyr Lys Val His Leu Thr Ala Ser Asn Leu Gly Glu Thr
625                 630                 635                 640

Val Thr Ser Lys Val Thr Ala Thr Thr Asp Glu Thr Tyr Leu Val Asp
                    645                 650                 655

Val Ser Asp Gly Glu Lys Val Val His His Met Lys Leu Asn Ile Gly
                660                 665                 670

Ser Gly Ala Ile Met Met Glu Asn Leu Ala Lys Gly Ala Lys Val Ile
                675                 680                 685

Gly Thr Ser Gly Asp Phe Glu Gln Ala Lys Lys Ile Phe Asp Gly Glu
            690                 695                 700

Lys Ser Asp Arg Phe Phe Thr Trp Gly Gln Thr Asn Trp Ile Ala Phe
705                 710                 715                 720

Asp Leu Gly Glu Ile Asn Leu Ala Lys Glu Trp Arg Leu Phe Asn Ala
                725                 730                 735

Glu Thr Asn Thr Glu Ile Lys Thr Asp Ser Ser Leu Asn Val Ala Lys
                740                 745                 750

Gly Arg Leu Gln Ile Leu Lys Asp Thr Thr Ile Asp Leu Glu Lys Met
            755                 760                 765

Asp Ile Lys Asn Arg Lys Glu Tyr Leu Ser Asn Asp Glu Asn Trp Thr
770                 775                 780

Asp Val Ala Gln Met Asp Asp Ala Lys Ala Ile Phe Asn Ser Lys Leu
785                 790                 795                 800

Ser Asn Val Leu Ser Arg Tyr Trp Arg Phe Cys Val Asp Gly Gly Ala
                805                 810                 815

Ser Ser Tyr Tyr Pro Gln Tyr Thr Glu Leu Gln Ile Leu Gly Gln Arg
            820                 825                 830

Leu Ser Asn Asp Val Ala Asn Thr Leu Asp
            835                 840

<210> SEQ ID NO 5
<211> LENGTH: 842
<212> TYPE: PRT
<213> ORGANISM: Artificial Sequence
<220> FEATURE:
<223> OTHER INFORMATION: Synthetic

<400> SEQUENCE: 5

Met Asp Lys His Leu Leu Val Lys Arg Thr Leu Gly Cys Val Cys Ala
1               5                   10                  15

Ala Thr Leu Met Gly Ala Ala Leu Ala Thr His His Asp Ser Leu Asn
                20                  25                  30

Thr Val Lys Ala Glu Glu Lys Thr Val Gln Thr Gly Lys Thr Asp Gln
            35                  40                  45

Gln Val Gly Ala Lys Leu Val Gln Glu Ile Arg Glu Gly Lys Arg Gly
        50                  55                  60

Pro Leu Tyr Ala Gly Tyr Phe Arg Thr Trp His Asp Arg Ala Ser Thr
65                  70                  75                  80

Gly Ile Asp Gly Lys Gln Gln His Pro Glu Asn Thr Met Ala Glu Val
                85                  90                  95

Pro Lys Glu Val Asp Ile Leu Phe Val Phe His Asp His Thr Ala Ser
                100                 105                 110

Asp Ser Pro Phe Trp Ser Glu Leu Lys Asp Ser Tyr Val His Lys Leu
            115                 120                 125

His Gln Gln Gly Thr Ala Leu Val Gln Thr Ile Gly Val Asn Glu Leu
```

-continued

```
            130                 135                 140
Asn Gly Arg Thr Gly Leu Ser Lys Asp Tyr Pro Asp Thr Pro Glu Gly
145                 150                 155                 160

Asn Lys Ala Leu Ala Ala Ile Val Lys Ala Phe Val Thr Asp Arg
            165                 170                 175

Gly Val Asp Gly Leu Asp Ile Asp Ile Glu His Glu Phe Thr Asn Lys
            180                 185                 190

Arg Thr Pro Glu Glu Asp Ala Arg Ala Leu Asn Val Phe Lys Glu Ile
            195                 200                 205

Ala Gln Leu Ile Gly Lys Asn Gly Ser Asp Lys Ser Lys Leu Leu Ile
            210                 215                 220

Met Asp Thr Gln Leu Ser Val Glu Asn Asn Pro Ile Phe Lys Gly Ile
225                 230                 235                 240

Ala Glu Asp Leu Asp Tyr Leu Leu Arg Gln Tyr Tyr Gly Ser Gln Gly
            245                 250                 255

Gly Glu Ala Glu Val Asp Thr Ile Asn Ser Asp Trp Asn Gln Tyr Gln
            260                 265                 270

Asn Tyr Ile Asp Ala Ser Gln Phe Met Ile Gly Phe Ser Phe Phe Glu
            275                 280                 285

Glu Ser Ala Ser Lys Gly Asn Leu Trp Phe Asp Val Asn Glu Tyr Asp
            290                 295                 300

Pro Asn Asn Pro Glu Lys Gly Lys Asp Ile Glu Gly Thr Arg Ala Lys
305                 310                 315                 320

Lys Tyr Ala Glu Trp Gln Pro Ser Thr Gly Gly Leu Lys Ala Gly Ile
            325                 330                 335

Phe Ser Tyr Ala Ile Asp Arg Asp Gly Val Ala His Val Pro Ser Thr
            340                 345                 350

Tyr Lys Asn Arg Thr Ser Thr Asn Leu Gln Arg His Glu Val Asp Asn
            355                 360                 365

Ile Ser His Thr Asp Tyr Thr Val Ser Arg Lys Leu Lys Thr Leu Met
            370                 375                 380

Thr Glu Asp Lys Arg Tyr Asp Val Ile Asp Gln Lys Asp Ile Pro Asp
385                 390                 395                 400

Pro Ala Leu Arg Glu Gln Ile Ile Gln Gln Val Gly Gln Tyr Lys Gly
            405                 410                 415

Asp Leu Glu Arg Tyr Asn Lys Thr Leu Val Leu Thr Gly Asp Lys Ile
            420                 425                 430

Gln Asn Leu Lys Gly Leu Glu Lys Leu Ser Lys Leu Gln Lys Leu Glu
            435                 440                 445

Leu Arg Gln Leu Ser Asn Val Lys Glu Ile Thr Pro Glu Leu Leu Pro
            450                 455                 460

Glu Ser Met Lys Lys Asp Ala Glu Leu Val Met Val Gly Met Thr Gly
465                 470                 475                 480

Leu Glu Lys Leu Asn Leu Ser Gly Leu Asn Arg Gln Thr Leu Asp Gly
            485                 490                 495

Ile Asp Val Asn Ser Ile Thr His Leu Thr Ser Phe Asp Ile Ser His
            500                 505                 510

Asn Ser Leu Asp Leu Ser Glu Lys Ser Glu Asp Arg Lys Leu Leu Met
            515                 520                 525

Thr Leu Met Glu Gln Val Ser Asn His Gln Lys Ile Thr Val Lys Asn
            530                 535                 540

Thr Ala Phe Glu Asn Gln Lys Pro Lys Gly Tyr Tyr Pro Gln Thr Tyr
545                 550                 555                 560
```

Asp Thr Lys Glu Gly His Tyr Asp Val Asp Asn Ala Glu His Asp Ile
                565                 570                 575

Leu Thr Asp Phe Val Phe Gly Thr Val Thr Lys Arg Asn Thr Phe Ile
            580                 585                 590

Gly Asp Glu Glu Ala Phe Ala Ile Tyr Lys Glu Gly Ala Val Asp Gly
        595                 600                 605

Arg Gln Tyr Val Ser Lys Asp Tyr Thr Tyr Glu Ala Phe Arg Lys Asp
    610                 615                 620

Tyr Lys Gly Tyr Lys Val His Leu Thr Ala Ser Asn Leu Gly Glu Thr
625                 630                 635                 640

Val Thr Ser Lys Val Thr Ala Thr Asp Glu Thr Tyr Leu Val Asp
                645                 650                 655

Val Ser Asp Gly Glu Lys Val Val His His Met Lys Leu Asn Ile Gly
                660                 665                 670

Ser Gly Ala Ile Met Met Glu Asn Leu Ala Lys Gly Ala Lys Val Ile
                675                 680                 685

Gly Thr Ser Gly Asp Phe Glu Gln Ala Lys Lys Ile Phe Asp Gly Glu
            690                 695                 700

Lys Ser Asp Arg Phe Phe Thr Trp Gly Gln Thr Asn Trp Ile Ala Phe
705                 710                 715                 720

Asp Leu Gly Glu Ile Asn Leu Ala Lys Glu Trp Arg Leu Phe Asn Ala
                725                 730                 735

Glu Thr Asn Thr Glu Ile Lys Thr Asp Ser Ser Leu Asn Val Ala Lys
            740                 745                 750

Gly Arg Leu Gln Ile Leu Lys Asp Thr Thr Ile Asp Leu Glu Lys Met
        755                 760                 765

Asp Ile Lys Asn Arg Lys Glu Tyr Leu Ser Asn Asp Glu Asn Trp Thr
770                 775                 780

Asp Val Ala Gln Met Asp Asp Ala Lys Ala Ile Phe Asn Ser Lys Leu
785                 790                 795                 800

Ser Asn Val Leu Ser Arg Tyr Trp Arg Phe Cys Val Asp Gly Gly Ala
                805                 810                 815

Ser Ser Tyr Tyr Pro Gln Tyr Thr Glu Leu Gln Ile Leu Gly Gln Arg
            820                 825                 830

Leu Ser Asn Asp Val Ala Asn Thr Leu Asp
        835                 840

<210> SEQ ID NO 6
<211> LENGTH: 842
<212> TYPE: PRT
<213> ORGANISM: Artificial Sequence
<220> FEATURE:
<223> OTHER INFORMATION: Synthetic

<400> SEQUENCE: 6

Met Asp Lys His Leu Leu Val Lys Arg Thr Leu Gly Cys Val Cys Ala
1               5                   10                  15

Ala Thr Leu Met Gly Ala Ala Leu Ala Thr His His Asp Ser Leu Asn
                20                  25                  30

Thr Val Lys Ala Glu Glu Lys Val Gln Thr Gly Lys Thr Asp Gln
            35                  40                  45

Gln Val Gly Ala Lys Leu Val Gln Glu Ile Arg Glu Gly Lys Arg Gly
        50                  55                  60

Pro Leu Tyr Ala Gly Tyr Phe Arg Thr Trp His Asp Arg Ala Ser Thr
65                  70                  75                  80

```
Gly Ile Asp Gly Lys Gln Gln His Pro Glu Asn Thr Met Ala Glu Val
                85                  90                  95

Pro Lys Glu Val Asp Ile Leu Phe Val Phe His Asp His Thr Ala Ser
            100                 105                 110

Asp Ser Pro Phe Trp Ser Glu Leu Lys Asp Ser Tyr Val His Lys Leu
        115                 120                 125

His Gln Gln Gly Thr Ala Leu Val Gln Asp Ile Gly Val Asn Glu Leu
    130                 135                 140

Asn Gly Arg Thr Gly Leu Ser Lys Asp Tyr Pro Asp Thr Pro Glu Gly
145                 150                 155                 160

Asn Lys Ala Leu Ala Ala Ile Val Lys Ala Phe Val Thr Asp Arg
                165                 170                 175

Gly Val Asp Gly Leu Asp Ile Asp Ile Glu His Glu Phe Thr Asn Lys
            180                 185                 190

Arg Thr Pro Glu Glu Asp Ala Arg Ala Leu Asn Val Phe Lys Glu Ile
        195                 200                 205

Ala Gln Leu Ile Gly Lys Asn Gly Ser Asp Lys Ser Lys Leu Leu Ile
    210                 215                 220

Met Asp Thr Thr Leu Ser Val Glu Asn Pro Ile Phe Lys Gly Ile
225                 230                 235                 240

Ala Glu Asp Leu Asp Tyr Leu Leu Arg Gln Tyr Tyr Gly Ser Gln Gly
            245                 250                 255

Gly Glu Ala Glu Val Asp Thr Ile Asn Ser Asp Trp Asn Gln Tyr Gln
        260                 265                 270

Asn Tyr Ile Asp Ala Ser Gln Phe Met Ile Gly Phe Ser Phe Glu
    275                 280                 285

Glu Ser Ala Ser Lys Gly Asn Leu Trp Phe Asp Val Asn Glu Tyr Asp
290                 295                 300

Pro Asn Asn Pro Glu Lys Gly Lys Asp Ile Glu Gly Thr Arg Ala Lys
305                 310                 315                 320

Lys Tyr Ala Glu Trp Gln Pro Ser Thr Gly Gly Leu Lys Ala Gly Ile
            325                 330                 335

Phe Ser Tyr Ala Ile Asp Arg Asp Gly Val Ala His Val Pro Ser Thr
        340                 345                 350

Tyr Lys Asn Arg Thr Ser Thr Asn Leu Gln Arg His Glu Val Asp Asn
    355                 360                 365

Ile Ser His Thr Asp Tyr Thr Val Ser Arg Lys Leu Lys Thr Leu Met
    370                 375                 380

Thr Glu Asp Lys Arg Tyr Asp Val Ile Asp Gln Lys Asp Ile Pro Asp
385                 390                 395                 400

Pro Ala Leu Arg Glu Gln Ile Ile Gln Gln Val Gly Gln Tyr Lys Gly
            405                 410                 415

Asp Leu Glu Arg Tyr Asn Lys Thr Leu Val Leu Thr Gly Asp Lys Ile
        420                 425                 430

Gln Asn Leu Lys Gly Leu Glu Lys Leu Ser Lys Leu Gln Lys Leu Glu
    435                 440                 445

Leu Arg Gln Leu Ser Asn Val Lys Glu Ile Thr Pro Glu Leu Leu Pro
    450                 455                 460

Glu Ser Met Lys Lys Asp Ala Glu Leu Val Met Val Gly Met Thr Gly
465                 470                 475                 480

Leu Glu Lys Leu Asn Leu Ser Gly Leu Asn Arg Gln Thr Leu Asp Gly
            485                 490                 495
```

Ile Asp Val Asn Ser Ile Thr His Leu Thr Ser Phe Asp Ile Ser His
            500                 505                 510

Asn Ser Leu Asp Leu Ser Glu Lys Ser Glu Asp Arg Lys Leu Leu Met
        515                 520                 525

Thr Leu Met Glu Gln Val Ser Asn His Gln Lys Ile Thr Val Lys Asn
    530                 535                 540

Thr Ala Phe Glu Asn Gln Lys Pro Lys Gly Tyr Tyr Pro Gln Thr Tyr
545                 550                 555                 560

Asp Thr Lys Glu Gly His Tyr Asp Val Asp Asn Ala Glu His Asp Ile
                565                 570                 575

Leu Thr Asp Phe Val Phe Gly Thr Val Thr Lys Arg Asn Thr Phe Ile
            580                 585                 590

Gly Asp Glu Glu Ala Phe Ala Ile Tyr Lys Glu Gly Ala Val Asp Gly
        595                 600                 605

Arg Gln Tyr Val Ser Lys Asp Tyr Thr Tyr Glu Ala Phe Arg Lys Asp
    610                 615                 620

Tyr Lys Gly Tyr Lys Val His Leu Thr Ala Ser Asn Leu Gly Glu Thr
625                 630                 635                 640

Val Thr Ser Lys Val Thr Ala Thr Thr Asp Glu Thr Tyr Leu Val Asp
                645                 650                 655

Val Ser Asp Gly Glu Lys Val Val His His Met Lys Leu Asn Ile Gly
            660                 665                 670

Ser Gly Ala Ile Met Met Glu Asn Leu Ala Lys Gly Ala Lys Val Ile
        675                 680                 685

Gly Thr Ser Gly Asp Phe Glu Gln Ala Lys Lys Ile Phe Asp Gly Glu
    690                 695                 700

Lys Ser Asp Arg Phe Phe Thr Trp Gly Gln Thr Asn Trp Ile Ala Phe
705                 710                 715                 720

Asp Leu Gly Glu Ile Asn Leu Ala Lys Glu Trp Arg Leu Phe Asn Ala
                725                 730                 735

Glu Thr Asn Thr Glu Ile Lys Thr Asp Ser Ser Leu Asn Val Ala Lys
            740                 745                 750

Gly Arg Leu Gln Ile Leu Lys Asp Thr Thr Ile Asp Leu Glu Lys Met
        755                 760                 765

Asp Ile Lys Asn Arg Lys Glu Tyr Leu Ser Asp Glu Asn Trp Thr
    770                 775                 780

Asp Val Ala Gln Met Asp Asp Ala Lys Ala Ile Phe Asn Ser Lys Leu
785                 790                 795                 800

Ser Asn Val Leu Ser Arg Tyr Trp Arg Phe Cys Val Asp Gly Gly Ala
                805                 810                 815

Ser Ser Tyr Tyr Pro Gln Tyr Thr Glu Leu Gln Ile Leu Gly Gln Arg
            820                 825                 830

Leu Ser Asn Asp Val Ala Asn Thr Leu Asp
        835                 840

<210> SEQ ID NO 7
<211> LENGTH: 842
<212> TYPE: PRT
<213> ORGANISM: Artificial Sequence
<220> FEATURE:
<223> OTHER INFORMATION: Synthetic

<400> SEQUENCE: 7

Met Asp Lys His Leu Leu Val Lys Arg Thr Leu Gly Cys Val Cys Ala
1               5                   10                  15

-continued

```
Ala Thr Leu Met Gly Ala Ala Leu Ala Thr His His Asp Ser Leu Asn
             20                  25                  30
Thr Val Lys Ala Glu Glu Lys Thr Val Gln Thr Gly Lys Thr Asp Gln
         35                  40                  45
Gln Val Gly Ala Lys Leu Val Gln Glu Ile Arg Glu Gly Lys Arg Gly
     50                  55                  60
Pro Leu Tyr Ala Gly Tyr Phe Arg Thr Trp His Asp Arg Ala Ser Thr
 65                  70                  75                  80
Gly Ile Asp Gly Lys Gln Gln His Pro Glu Asn Thr Met Ala Glu Val
                 85                  90                  95
Pro Lys Glu Val Asp Ile Leu Phe Val Phe His Asp His Thr Ala Ser
            100                 105                 110
Asp Ser Pro Phe Trp Ser Glu Leu Lys Asp Ser Tyr Val His Lys Leu
        115                 120                 125
His Gln Gln Gly Thr Ala Leu Val Gln Glu Ile Gly Val Asn Glu Leu
    130                 135                 140
Asn Gly Arg Thr Gly Leu Ser Lys Asp Tyr Pro Asp Thr Pro Glu Gly
145                 150                 155                 160
Asn Lys Ala Leu Ala Ala Ile Val Lys Ala Phe Val Thr Asp Arg
                165                 170                 175
Gly Val Asp Gly Leu Asp Ile Asp Ile Glu His Glu Phe Thr Asn Lys
            180                 185                 190
Arg Thr Pro Glu Glu Asp Ala Arg Ala Leu Asn Val Phe Lys Glu Ile
        195                 200                 205
Ala Gln Leu Ile Gly Lys Asn Gly Ser Asp Lys Ser Lys Leu Leu Ile
    210                 215                 220
Met Asp Thr Thr Leu Ser Val Glu Asn Asn Pro Ile Phe Lys Gly Ile
225                 230                 235                 240
Ala Glu Asp Leu Asp Tyr Leu Leu Arg Gln Tyr Tyr Gly Ser Gln Gly
                245                 250                 255
Gly Glu Ala Glu Val Asp Thr Ile Asn Ser Asp Trp Asn Gln Tyr Gln
            260                 265                 270
Asn Tyr Ile Asp Ala Ser Gln Phe Met Ile Gly Phe Ser Phe Phe Glu
        275                 280                 285
Glu Ser Ala Ser Lys Gly Asn Leu Trp Phe Asp Val Asn Glu Tyr Asp
    290                 295                 300
Pro Asn Asn Pro Glu Lys Gly Lys Asp Ile Glu Gly Thr Arg Ala Lys
305                 310                 315                 320
Lys Tyr Ala Glu Trp Gln Pro Ser Thr Gly Gly Leu Lys Ala Gly Ile
                325                 330                 335
Phe Ser Tyr Ala Ile Asp Arg Asp Gly Val Ala His Val Pro Ser Thr
            340                 345                 350
Tyr Lys Asn Arg Thr Ser Thr Asn Leu Gln Arg His Glu Val Asp Asn
        355                 360                 365
Ile Ser His Thr Asp Tyr Thr Val Ser Arg Lys Leu Lys Thr Leu Met
    370                 375                 380
Thr Glu Asp Lys Arg Tyr Asp Val Ile Asp Gln Lys Asp Ile Pro Asp
385                 390                 395                 400
Pro Ala Leu Arg Glu Gln Ile Ile Gln Gln Val Gly Gln Tyr Lys Gly
                405                 410                 415
Asp Leu Glu Arg Tyr Asn Lys Thr Leu Val Leu Thr Gly Asp Lys Ile
            420                 425                 430
Gln Asn Leu Lys Gly Leu Glu Lys Leu Ser Lys Leu Gln Lys Leu Glu
```

```
                    435                 440                 445
Leu Arg Gln Leu Ser Asn Val Lys Glu Ile Thr Pro Glu Leu Leu Pro
450                 455                 460

Glu Ser Met Lys Lys Asp Ala Glu Leu Val Met Val Gly Met Thr Gly
465                 470                 475                 480

Leu Glu Lys Leu Asn Leu Ser Gly Leu Asn Arg Gln Thr Leu Asp Gly
                485                 490                 495

Ile Asp Val Asn Ser Ile Thr His Leu Thr Ser Phe Asp Ile Ser His
                500                 505                 510

Asn Ser Leu Asp Leu Ser Glu Lys Ser Glu Asp Arg Lys Leu Leu Met
                515                 520                 525

Thr Leu Met Glu Gln Val Ser Asn His Gln Lys Ile Thr Val Lys Asn
530                 535                 540

Thr Ala Phe Glu Asn Gln Lys Pro Lys Gly Tyr Tyr Pro Gln Thr Tyr
545                 550                 555                 560

Asp Thr Lys Glu Gly His Tyr Asp Val Asp Asn Ala Glu His Asp Ile
                565                 570                 575

Leu Thr Asp Phe Val Phe Gly Thr Val Thr Lys Arg Asn Thr Phe Ile
                580                 585                 590

Gly Asp Glu Glu Ala Phe Ala Ile Tyr Lys Glu Gly Ala Val Asp Gly
                595                 600                 605

Arg Gln Tyr Val Ser Lys Asp Tyr Thr Tyr Glu Ala Phe Arg Lys Asp
610                 615                 620

Tyr Lys Gly Tyr Lys Val His Leu Thr Ala Ser Asn Leu Gly Glu Thr
625                 630                 635                 640

Val Thr Ser Lys Val Thr Ala Thr Thr Asp Glu Thr Tyr Leu Val Asp
                645                 650                 655

Val Ser Asp Gly Glu Lys Val Val His His Met Lys Leu Asn Ile Gly
                660                 665                 670

Ser Gly Ala Ile Met Met Glu Asn Leu Ala Lys Gly Ala Lys Val Ile
                675                 680                 685

Gly Thr Ser Gly Asp Phe Glu Gln Ala Lys Lys Ile Phe Asp Gly Glu
                690                 695                 700

Lys Ser Asp Arg Phe Phe Thr Trp Gly Gln Thr Asn Trp Ile Ala Phe
705                 710                 715                 720

Asp Leu Gly Glu Ile Asn Leu Ala Lys Glu Trp Arg Leu Phe Asn Ala
                725                 730                 735

Glu Thr Asn Thr Glu Ile Lys Thr Asp Ser Ser Leu Asn Val Ala Lys
                740                 745                 750

Gly Arg Leu Gln Ile Leu Lys Asp Thr Thr Ile Asp Leu Glu Lys Met
                755                 760                 765

Asp Ile Lys Asn Arg Lys Glu Tyr Leu Ser Asn Asp Glu Asn Trp Thr
770                 775                 780

Asp Val Ala Gln Met Asp Asp Ala Lys Ala Ile Phe Asn Ser Lys Leu
785                 790                 795                 800

Ser Asn Val Leu Ser Arg Tyr Trp Arg Phe Cys Val Asp Gly Gly Ala
                805                 810                 815

Ser Ser Tyr Tyr Pro Gln Tyr Thr Glu Leu Gln Ile Leu Gly Gln Arg
                820                 825                 830

Leu Ser Asn Asp Val Ala Asn Thr Leu Asp
                835                 840

<210> SEQ ID NO 8
```

<211> LENGTH: 842
<212> TYPE: PRT
<213> ORGANISM: Artificial Sequence
<220> FEATURE:
<223> OTHER INFORMATION: Synthetic

<400> SEQUENCE: 8

```
Met Asp Lys His Leu Leu Val Lys Arg Thr Leu Gly Cys Val Cys Ala
1               5                   10                  15

Ala Thr Leu Met Gly Ala Ala Leu Ala Thr His His Asp Ser Leu Asn
            20                  25                  30

Thr Val Lys Ala Glu Glu Lys Thr Val Gln Thr Gly Lys Thr Asp Gln
        35                  40                  45

Gln Val Gly Ala Lys Leu Val Gln Glu Ile Arg Glu Gly Lys Arg Gly
    50                  55                  60

Pro Leu Tyr Ala Gly Tyr Phe Arg Thr Trp His Asp Arg Ala Ser Thr
65                  70                  75                  80

Gly Ile Asp Gly Lys Gln Gln His Pro Glu Asn Thr Met Ala Glu Val
                85                  90                  95

Pro Lys Glu Val Asp Ile Leu Phe Val Phe His Asp His Thr Ala Ser
            100                 105                 110

Asp Ser Pro Phe Trp Ser Glu Leu Lys Asp Ser Tyr Val His Lys Leu
        115                 120                 125

His Gln Gln Gly Thr Ala Leu Val Gln Phe Ile Gly Val Asn Glu Leu
    130                 135                 140

Asn Gly Arg Thr Gly Leu Ser Lys Asp Tyr Pro Asp Thr Pro Glu Gly
145                 150                 155                 160

Asn Lys Ala Leu Ala Ala Ile Val Lys Ala Phe Val Thr Asp Arg
                165                 170                 175

Gly Val Asp Gly Leu Asp Ile Asp Ile Glu His Glu Phe Thr Asn Lys
            180                 185                 190

Arg Thr Pro Glu Glu Asp Ala Arg Ala Leu Asn Val Phe Lys Glu Ile
        195                 200                 205

Ala Gln Leu Ile Gly Lys Asn Gly Ser Asp Lys Ser Lys Leu Leu Ile
    210                 215                 220

Met Asp Thr Thr Leu Ser Val Glu Asn Asn Pro Ile Phe Lys Gly Ile
225                 230                 235                 240

Ala Glu Asp Leu Asp Tyr Leu Leu Arg Gln Tyr Tyr Gly Ser Gln Gly
                245                 250                 255

Gly Glu Ala Glu Val Asp Thr Ile Asn Ser Asp Trp Asn Gln Tyr Gln
            260                 265                 270

Asn Tyr Ile Asp Ala Ser Gln Phe Met Ile Gly Phe Ser Phe Phe Glu
        275                 280                 285

Glu Ser Ala Ser Lys Gly Asn Leu Trp Phe Asp Val Asn Glu Tyr Asp
    290                 295                 300

Pro Asn Asn Pro Glu Lys Gly Lys Asp Ile Glu Gly Thr Arg Ala Lys
305                 310                 315                 320

Lys Tyr Ala Glu Trp Gln Pro Ser Thr Gly Gly Leu Lys Ala Gly Ile
                325                 330                 335

Phe Ser Tyr Ala Ile Asp Arg Asp Gly Val Ala His Val Pro Ser Thr
            340                 345                 350

Tyr Lys Asn Arg Thr Ser Thr Asn Leu Gln Arg His Glu Val Asp Asn
        355                 360                 365

Ile Ser His Thr Asp Tyr Thr Val Ser Arg Lys Leu Lys Thr Leu Met
    370                 375                 380
```

-continued

```
Thr Glu Asp Lys Arg Tyr Asp Val Ile Asp Gln Lys Asp Ile Pro Asp
385                 390                 395                 400

Pro Ala Leu Arg Glu Gln Ile Ile Gln Gln Val Gly Gln Tyr Lys Gly
            405                 410                 415

Asp Leu Glu Arg Tyr Asn Lys Thr Leu Val Leu Thr Gly Asp Lys Ile
            420                 425                 430

Gln Asn Leu Lys Gly Leu Glu Lys Leu Ser Lys Leu Gln Lys Leu Glu
            435                 440                 445

Leu Arg Gln Leu Ser Asn Val Lys Glu Ile Thr Pro Glu Leu Leu Pro
450                 455                 460

Glu Ser Met Lys Lys Asp Ala Glu Leu Val Met Val Gly Met Thr Gly
465                 470                 475                 480

Leu Glu Lys Leu Asn Leu Ser Gly Leu Asn Arg Gln Thr Leu Asp Gly
            485                 490                 495

Ile Asp Val Asn Ser Ile Thr His Leu Thr Ser Phe Asp Ile Ser His
            500                 505                 510

Asn Ser Leu Asp Leu Ser Glu Lys Ser Glu Asp Arg Lys Leu Leu Met
            515                 520                 525

Thr Leu Met Glu Gln Val Ser Asn His Gln Lys Ile Thr Val Lys Asn
530                 535                 540

Thr Ala Phe Glu Asn Gln Lys Pro Lys Gly Tyr Tyr Pro Gln Thr Tyr
545                 550                 555                 560

Asp Thr Lys Glu Gly His Tyr Asp Val Asp Asn Ala Glu His Asp Ile
            565                 570                 575

Leu Thr Asp Phe Val Phe Gly Thr Val Thr Lys Arg Asn Thr Phe Ile
            580                 585                 590

Gly Asp Glu Glu Ala Phe Ala Ile Tyr Lys Glu Gly Ala Val Asp Gly
            595                 600                 605

Arg Gln Tyr Val Ser Lys Asp Tyr Thr Tyr Glu Ala Phe Arg Lys Asp
610                 615                 620

Tyr Lys Gly Tyr Lys Val His Leu Thr Ala Ser Asn Leu Gly Glu Thr
625                 630                 635                 640

Val Thr Ser Lys Val Thr Ala Thr Asp Glu Thr Tyr Leu Val Asp
            645                 650                 655

Val Ser Asp Gly Glu Lys Val Val His His Met Lys Leu Asn Ile Gly
            660                 665                 670

Ser Gly Ala Ile Met Met Glu Asn Leu Ala Lys Gly Ala Lys Val Ile
            675                 680                 685

Gly Thr Ser Gly Asp Phe Glu Gln Ala Lys Lys Ile Phe Asp Gly Glu
            690                 695                 700

Lys Ser Asp Arg Phe Phe Thr Trp Gly Gln Thr Asn Trp Ile Ala Phe
705                 710                 715                 720

Asp Leu Gly Glu Ile Asn Leu Ala Lys Glu Trp Arg Leu Phe Asn Ala
            725                 730                 735

Glu Thr Asn Thr Glu Ile Lys Thr Asp Ser Ser Leu Asn Val Ala Lys
            740                 745                 750

Gly Arg Leu Gln Ile Leu Lys Asp Thr Thr Ile Asp Leu Glu Lys Met
            755                 760                 765

Asp Ile Lys Asn Arg Lys Glu Tyr Leu Ser Asn Asp Glu Asn Trp Thr
            770                 775                 780

Asp Val Ala Gln Met Asp Asp Ala Lys Ala Ile Phe Asn Ser Lys Leu
785                 790                 795                 800
```

```
Ser Asn Val Leu Ser Arg Tyr Trp Arg Phe Cys Val Asp Gly Gly Ala
            805                 810                 815

Ser Ser Tyr Tyr Pro Gln Tyr Thr Glu Leu Gln Ile Leu Gly Gln Arg
            820                 825                 830

Leu Ser Asn Asp Val Ala Asn Thr Leu Asp
            835                 840

<210> SEQ ID NO 9
<211> LENGTH: 842
<212> TYPE: PRT
<213> ORGANISM: Artificial Sequence
<220> FEATURE:
<223> OTHER INFORMATION: Synthetic

<400> SEQUENCE: 9

Met Asp Lys His Leu Leu Val Lys Arg Thr Leu Gly Cys Val Cys Ala
1               5                   10                  15

Ala Thr Leu Met Gly Ala Ala Leu Ala Thr His His Asp Ser Leu Asn
                20                  25                  30

Thr Val Lys Ala Glu Glu Lys Thr Val Gln Thr Gly Lys Thr Asp Gln
            35                  40                  45

Gln Val Gly Ala Lys Leu Val Gln Glu Ile Arg Glu Gly Lys Arg Gly
        50                  55                  60

Pro Leu Tyr Ala Gly Tyr Phe Arg Thr Trp His Asp Arg Ala Ser Thr
65                  70                  75                  80

Gly Ile Asp Gly Lys Gln Gln His Pro Glu Asn Thr Met Ala Glu Val
                85                  90                  95

Pro Lys Glu Val Asp Ile Leu Phe Val Phe His Asp His Thr Ala Ser
            100                 105                 110

Asp Ser Pro Phe Trp Ser Glu Leu Lys Asp Ser Tyr Val His Lys Leu
        115                 120                 125

His Gln Gln Gly Thr Ala Leu Val Gln His Ile Gly Val Asn Glu Leu
    130                 135                 140

Asn Gly Arg Thr Gly Leu Ser Lys Asp Tyr Pro Asp Thr Pro Glu Gly
145                 150                 155                 160

Asn Lys Ala Leu Ala Ala Ile Val Lys Ala Phe Val Thr Asp Arg
                165                 170                 175

Gly Val Asp Gly Leu Asp Ile Asp Ile Glu His Glu Phe Thr Asn Lys
            180                 185                 190

Arg Thr Pro Glu Glu Asp Ala Arg Ala Leu Asn Val Phe Lys Glu Ile
        195                 200                 205

Ala Gln Leu Ile Gly Lys Asn Gly Ser Asp Lys Ser Lys Leu Leu Ile
    210                 215                 220

Met Asp Thr Thr Leu Ser Val Glu Asn Asn Pro Ile Phe Lys Gly Ile
225                 230                 235                 240

Ala Glu Asp Leu Asp Tyr Leu Leu Arg Gln Tyr Tyr Gly Ser Gln Gly
                245                 250                 255

Gly Glu Ala Glu Val Asp Thr Ile Asn Ser Asp Trp Asn Gln Tyr Gln
            260                 265                 270

Asn Tyr Ile Asp Ala Ser Gln Phe Met Ile Gly Phe Ser Phe Phe Glu
        275                 280                 285

Glu Ser Ala Ser Lys Gly Asn Leu Trp Phe Asp Val Asn Glu Tyr Asp
    290                 295                 300

Pro Asn Asn Pro Glu Lys Gly Lys Asp Ile Glu Gly Thr Arg Ala Lys
305                 310                 315                 320
```

```
Lys Tyr Ala Glu Trp Gln Pro Ser Thr Gly Leu Lys Ala Gly Ile
            325                 330                 335
Phe Ser Tyr Ala Ile Asp Arg Asp Gly Val Ala His Val Pro Ser Thr
            340                 345                 350
Tyr Lys Asn Arg Thr Ser Thr Asn Leu Gln Arg His Glu Val Asp Asn
            355                 360                 365
Ile Ser His Thr Asp Tyr Thr Val Ser Arg Lys Leu Lys Thr Leu Met
            370                 375                 380
Thr Glu Asp Lys Arg Tyr Asp Val Ile Asp Gln Lys Asp Ile Pro Asp
385                 390                 395                 400
Pro Ala Leu Arg Glu Gln Ile Ile Gln Gln Val Gly Gln Tyr Lys Gly
            405                 410                 415
Asp Leu Glu Arg Tyr Asn Lys Thr Leu Val Leu Thr Gly Asp Lys Ile
            420                 425                 430
Gln Asn Leu Lys Gly Leu Glu Lys Leu Ser Lys Leu Gln Lys Leu Glu
            435                 440                 445
Leu Arg Gln Leu Ser Asn Val Lys Glu Ile Thr Pro Glu Leu Leu Pro
            450                 455                 460
Glu Ser Met Lys Lys Asp Ala Glu Leu Val Met Val Gly Met Thr Gly
465                 470                 475                 480
Leu Glu Lys Leu Asn Leu Ser Gly Leu Asn Arg Gln Thr Leu Asp Gly
            485                 490                 495
Ile Asp Val Asn Ser Ile Thr His Leu Thr Ser Phe Asp Ile Ser His
            500                 505                 510
Asn Ser Leu Asp Leu Ser Glu Lys Ser Glu Asp Arg Lys Leu Leu Met
            515                 520                 525
Thr Leu Met Glu Gln Val Ser Asn His Gln Lys Ile Thr Val Lys Asn
            530                 535                 540
Thr Ala Phe Glu Asn Gln Lys Pro Lys Gly Tyr Tyr Pro Gln Thr Tyr
545                 550                 555                 560
Asp Thr Lys Glu Gly His Tyr Asp Val Asp Asn Ala Glu His Asp Ile
            565                 570                 575
Leu Thr Asp Phe Val Phe Gly Thr Val Thr Lys Arg Asn Thr Phe Ile
            580                 585                 590
Gly Asp Glu Glu Ala Phe Ala Ile Tyr Lys Glu Gly Ala Val Asp Gly
            595                 600                 605
Arg Gln Tyr Val Ser Lys Asp Tyr Thr Tyr Glu Ala Phe Arg Lys Asp
            610                 615                 620
Tyr Lys Gly Tyr Lys Val His Leu Thr Ala Ser Asn Leu Gly Glu Thr
625                 630                 635                 640
Val Thr Ser Lys Val Thr Ala Thr Thr Asp Glu Thr Tyr Leu Val Asp
            645                 650                 655
Val Ser Asp Gly Glu Lys Val Val His His Met Lys Leu Asn Ile Gly
            660                 665                 670
Ser Gly Ala Ile Met Met Glu Asn Leu Ala Lys Gly Ala Lys Val Ile
            675                 680                 685
Gly Thr Ser Gly Asp Phe Glu Gln Ala Lys Lys Ile Phe Asp Gly Glu
            690                 695                 700
Lys Ser Asp Arg Phe Phe Thr Trp Gly Gln Thr Asn Trp Ile Ala Phe
705                 710                 715                 720
Asp Leu Gly Glu Ile Asn Leu Ala Lys Glu Trp Arg Leu Phe Asn Ala
            725                 730                 735
Glu Thr Asn Thr Glu Ile Lys Thr Asp Ser Ser Leu Asn Val Ala Lys
```

```
                    740                 745                 750
Gly Arg Leu Gln Ile Leu Lys Asp Thr Thr Ile Asp Leu Glu Lys Met
        755                 760                 765
Asp Ile Lys Asn Arg Lys Glu Tyr Leu Ser Asn Asp Glu Asn Trp Thr
        770                 775                 780
Asp Val Ala Gln Met Asp Asp Ala Lys Ala Ile Phe Asn Ser Lys Leu
785                 790                 795                 800
Ser Asn Val Leu Ser Arg Tyr Trp Arg Phe Cys Val Asp Gly Gly Ala
                805                 810                 815
Ser Ser Tyr Tyr Pro Gln Tyr Thr Glu Leu Gln Ile Leu Gly Gln Arg
                820                 825                 830
Leu Ser Asn Asp Val Ala Asn Thr Leu Asp
        835                 840

<210> SEQ ID NO 10
<211> LENGTH: 842
<212> TYPE: PRT
<213> ORGANISM: Artificial Sequence
<220> FEATURE:
<223> OTHER INFORMATION: Synthetic

<400> SEQUENCE: 10

Met Asp Lys His Leu Leu Val Lys Arg Thr Leu Gly Cys Val Cys Ala
1               5                   10                  15
Ala Thr Leu Met Gly Ala Ala Leu Ala Thr His His Asp Ser Leu Asn
                20                  25                  30
Thr Val Lys Ala Glu Glu Lys Thr Val Gln Thr Gly Lys Thr Asp Gln
        35                  40                  45
Gln Val Gly Ala Lys Leu Val Gln Glu Ile Arg Glu Gly Lys Arg Gly
    50                  55                  60
Pro Leu Tyr Ala Gly Tyr Phe Arg Thr Trp His Asp Arg Ala Ser Thr
65                  70                  75                  80
Gly Ile Asp Gly Lys Gln Gln His Pro Glu Asn Thr Met Ala Glu Val
                85                  90                  95
Pro Lys Glu Val Asp Ile Leu Phe Val Phe His Asp His Thr Ala Ser
                100                 105                 110
Asp Ser Pro Phe Trp Ser Glu Leu Lys Asp Ser Tyr Val His Lys Leu
        115                 120                 125
His Gln Gln Gly Thr Ala Leu Val Gln Lys Ile Gly Val Asn Glu Leu
    130                 135                 140
Asn Gly Arg Thr Gly Leu Ser Lys Asp Tyr Pro Asp Thr Pro Glu Gly
145                 150                 155                 160
Asn Lys Ala Leu Ala Ala Ala Ile Val Lys Ala Phe Val Thr Asp Arg
                165                 170                 175
Gly Val Asp Gly Leu Asp Ile Asp Ile Glu His Glu Phe Thr Asn Lys
                180                 185                 190
Arg Thr Pro Glu Glu Asp Ala Arg Ala Leu Asn Val Phe Lys Glu Ile
        195                 200                 205
Ala Gln Leu Ile Gly Lys Asn Gly Ser Asp Lys Ser Lys Leu Leu Ile
    210                 215                 220
Met Asp Thr Thr Leu Ser Val Glu Asn Asn Pro Ile Phe Lys Gly Ile
225                 230                 235                 240
Ala Glu Asp Leu Asp Tyr Leu Leu Arg Gln Tyr Tyr Gly Ser Gln Gly
                245                 250                 255
Gly Glu Ala Glu Val Asp Thr Ile Asn Ser Asp Trp Asn Gln Tyr Gln
```

```
              260                 265                 270
Asn Tyr Ile Asp Ala Ser Gln Phe Met Ile Gly Phe Ser Phe Phe Glu
            275                 280                 285
Glu Ser Ala Ser Lys Gly Asn Leu Trp Phe Asp Val Asn Glu Tyr Asp
290                 295                 300
Pro Asn Asn Pro Glu Lys Gly Lys Asp Ile Glu Gly Thr Arg Ala Lys
305                 310                 315                 320
Lys Tyr Ala Glu Trp Gln Pro Ser Thr Gly Gly Leu Lys Ala Gly Ile
                325                 330                 335
Phe Ser Tyr Ala Ile Asp Arg Asp Gly Val Ala His Val Pro Ser Thr
            340                 345                 350
Tyr Lys Asn Arg Thr Ser Thr Asn Leu Gln Arg His Glu Val Asp Asn
        355                 360                 365
Ile Ser His Thr Asp Tyr Thr Val Ser Arg Lys Leu Lys Thr Leu Met
    370                 375                 380
Thr Glu Asp Lys Arg Tyr Asp Val Ile Asp Gln Lys Asp Ile Pro Asp
385                 390                 395                 400
Pro Ala Leu Arg Glu Gln Ile Ile Gln Gln Val Gly Gln Tyr Lys Gly
                405                 410                 415
Asp Leu Glu Arg Tyr Asn Lys Thr Leu Val Leu Thr Gly Asp Lys Ile
            420                 425                 430
Gln Asn Leu Lys Gly Leu Glu Lys Leu Ser Lys Leu Gln Lys Leu Glu
        435                 440                 445
Leu Arg Gln Leu Ser Asn Val Lys Glu Ile Thr Pro Glu Leu Leu Pro
    450                 455                 460
Glu Ser Met Lys Lys Asp Ala Glu Leu Val Met Val Gly Met Thr Gly
465                 470                 475                 480
Leu Glu Lys Leu Asn Leu Ser Gly Leu Asn Arg Gln Thr Leu Asp Gly
                485                 490                 495
Ile Asp Val Asn Ser Ile Thr His Leu Thr Ser Phe Asp Ile Ser His
            500                 505                 510
Asn Ser Leu Asp Leu Ser Glu Lys Ser Glu Asp Arg Lys Leu Leu Met
        515                 520                 525
Thr Leu Met Glu Gln Val Ser Asn His Gln Lys Ile Thr Val Lys Asn
    530                 535                 540
Thr Ala Phe Glu Asn Gln Lys Pro Lys Gly Tyr Tyr Pro Gln Thr Tyr
545                 550                 555                 560
Asp Thr Lys Glu Gly His Tyr Asp Val Asp Asn Ala Glu His Asp Ile
                565                 570                 575
Leu Thr Asp Phe Val Phe Gly Thr Val Thr Lys Arg Asn Thr Phe Ile
            580                 585                 590
Gly Asp Glu Glu Ala Phe Ala Ile Tyr Lys Glu Gly Ala Val Asp Gly
        595                 600                 605
Arg Gln Tyr Val Ser Lys Asp Tyr Thr Tyr Glu Ala Phe Arg Lys Asp
    610                 615                 620
Tyr Lys Gly Tyr Lys Val His Leu Thr Ala Ser Asn Leu Gly Glu Thr
625                 630                 635                 640
Val Thr Ser Lys Val Thr Ala Thr Asp Glu Thr Tyr Leu Val Asp
                645                 650                 655
Val Ser Asp Gly Glu Lys Val Val His His Met Lys Leu Asn Ile Gly
            660                 665                 670
Ser Gly Ala Ile Met Met Glu Asn Leu Ala Lys Gly Ala Lys Val Ile
        675                 680                 685
```

-continued

```
Gly Thr Ser Gly Asp Phe Glu Gln Ala Lys Lys Ile Phe Asp Gly Glu
        690                 695                 700
Lys Ser Asp Arg Phe Phe Thr Trp Gly Gln Thr Asn Trp Ile Ala Phe
705                 710                 715                 720
Asp Leu Gly Glu Ile Asn Leu Ala Lys Glu Trp Arg Leu Phe Asn Ala
                725                 730                 735
Glu Thr Asn Thr Glu Ile Lys Thr Asp Ser Ser Leu Asn Val Ala Lys
            740                 745                 750
Gly Arg Leu Gln Ile Leu Lys Asp Thr Thr Ile Asp Leu Glu Lys Met
        755                 760                 765
Asp Ile Lys Asn Arg Lys Glu Tyr Leu Ser Asn Asp Glu Asn Trp Thr
770                 775                 780
Asp Val Ala Gln Met Asp Asp Ala Lys Ala Ile Phe Asn Ser Lys Leu
785                 790                 795                 800
Ser Asn Val Leu Ser Arg Tyr Trp Arg Phe Cys Val Asp Gly Gly Ala
                805                 810                 815
Ser Ser Tyr Tyr Pro Gln Tyr Thr Glu Leu Gln Ile Leu Gly Gln Arg
            820                 825                 830
Leu Ser Asn Asp Val Ala Asn Thr Leu Asp
        835                 840
```

<210> SEQ ID NO 11
<211> LENGTH: 842
<212> TYPE: PRT
<213> ORGANISM: Artificial Sequence
<220> FEATURE:
<223> OTHER INFORMATION: Synthetic

<400> SEQUENCE: 11

```
Met Asp Lys His Leu Leu Val Lys Arg Thr Leu Gly Cys Val Cys Ala
1               5                   10                  15
Ala Thr Leu Met Gly Ala Ala Leu Ala Thr His His Asp Ser Leu Asn
            20                  25                  30
Thr Val Lys Ala Glu Glu Lys Thr Val Gln Thr Gly Lys Thr Asp Gln
        35                  40                  45
Gln Val Gly Ala Lys Leu Val Gln Glu Ile Arg Glu Gly Lys Arg Gly
    50                  55                  60
Pro Leu Tyr Ala Gly Tyr Phe Arg Thr Trp His Asp Arg Ala Ser Thr
65                  70                  75                  80
Gly Ile Asp Gly Lys Gln Gln His Pro Glu Asn Thr Met Ala Glu Val
                85                  90                  95
Pro Lys Glu Val Asp Ile Leu Phe Val Phe His Asp His Thr Ala Ser
            100                 105                 110
Asp Ser Pro Phe Trp Ser Glu Leu Lys Asp Ser Tyr Val His Lys Leu
        115                 120                 125
His Gln Gln Gly Thr Ala Leu Val Gln Leu Ile Gly Val Asn Glu Leu
    130                 135                 140
Asn Gly Arg Thr Gly Leu Ser Lys Asp Tyr Pro Asp Thr Pro Glu Gly
145                 150                 155                 160
Asn Lys Ala Leu Ala Ala Ile Val Lys Ala Phe Val Thr Asp Arg
                165                 170                 175
Gly Val Asp Gly Leu Asp Ile Asp Ile Glu His Glu Phe Thr Asn Lys
            180                 185                 190
Arg Thr Pro Glu Glu Asp Ala Arg Ala Leu Asn Val Phe Lys Glu Ile
        195                 200                 205
```

```
Ala Gln Leu Ile Gly Lys Asn Gly Ser Asp Lys Ser Lys Leu Leu Ile
    210                 215                 220
Met Asp Thr Thr Leu Ser Val Glu Asn Asn Pro Ile Phe Lys Gly Ile
225                 230                 235                 240
Ala Glu Asp Leu Asp Tyr Leu Leu Arg Gln Tyr Tyr Gly Ser Gln Gly
                245                 250                 255
Gly Glu Ala Glu Val Asp Thr Ile Asn Ser Asp Trp Asn Gln Tyr Gln
                260                 265                 270
Asn Tyr Ile Asp Ala Ser Gln Phe Met Ile Gly Phe Ser Phe Phe Glu
        275                 280                 285
Glu Ser Ala Ser Lys Gly Asn Leu Trp Phe Asp Val Asn Glu Tyr Asp
    290                 295                 300
Pro Asn Asn Pro Glu Lys Gly Lys Asp Ile Glu Gly Thr Arg Ala Lys
305                 310                 315                 320
Lys Tyr Ala Glu Trp Gln Pro Ser Thr Gly Gly Leu Lys Ala Gly Ile
                325                 330                 335
Phe Ser Tyr Ala Ile Asp Arg Asp Gly Val Ala His Val Pro Ser Thr
                340                 345                 350
Tyr Lys Asn Arg Thr Ser Thr Asn Leu Gln Arg His Glu Val Asp Asn
        355                 360                 365
Ile Ser His Thr Asp Tyr Thr Val Ser Arg Lys Leu Lys Thr Leu Met
    370                 375                 380
Thr Glu Asp Lys Arg Tyr Asp Val Ile Asp Gln Lys Asp Ile Pro Asp
385                 390                 395                 400
Pro Ala Leu Arg Glu Gln Ile Ile Gln Gln Val Gly Gln Tyr Lys Gly
                405                 410                 415
Asp Leu Glu Arg Tyr Asn Lys Thr Leu Val Leu Thr Gly Asp Lys Ile
                420                 425                 430
Gln Asn Leu Lys Gly Leu Glu Lys Leu Ser Leu Gln Lys Leu Glu
        435                 440                 445
Leu Arg Gln Leu Ser Asn Val Lys Glu Ile Thr Pro Glu Leu Leu Pro
    450                 455                 460
Glu Ser Met Lys Lys Asp Ala Glu Leu Val Met Val Gly Met Thr Gly
465                 470                 475                 480
Leu Glu Lys Leu Asn Leu Ser Gly Leu Asn Arg Gln Thr Leu Asp Gly
                485                 490                 495
Ile Asp Val Asn Ser Ile Thr His Leu Thr Ser Phe Asp Ile Ser His
                500                 505                 510
Asn Ser Leu Asp Leu Ser Glu Lys Ser Glu Asp Arg Lys Leu Leu Met
        515                 520                 525
Thr Leu Met Glu Gln Val Ser Asn His Gln Lys Ile Thr Val Lys Asn
    530                 535                 540
Thr Ala Phe Glu Asn Gln Lys Pro Lys Gly Tyr Tyr Pro Gln Thr Tyr
545                 550                 555                 560
Asp Thr Lys Glu Gly His Tyr Asp Val Asp Asn Ala Glu His Asp Ile
                565                 570                 575
Leu Thr Asp Phe Val Phe Gly Thr Val Thr Lys Arg Asn Thr Phe Ile
                580                 585                 590
Gly Asp Glu Glu Ala Phe Ala Ile Tyr Lys Glu Gly Ala Val Asp Gly
        595                 600                 605
Arg Gln Tyr Val Ser Lys Asp Tyr Thr Tyr Glu Ala Phe Arg Lys Asp
    610                 615                 620
```

Tyr Lys Gly Tyr Lys Val His Leu Thr Ala Ser Asn Leu Gly Glu Thr
625                 630                 635                 640

Val Thr Ser Lys Val Thr Ala Thr Thr Asp Glu Thr Tyr Leu Val Asp
            645                 650                 655

Val Ser Asp Gly Glu Lys Val Val His His Met Lys Leu Asn Ile Gly
        660                 665                 670

Ser Gly Ala Ile Met Met Glu Asn Leu Ala Lys Gly Ala Lys Val Ile
    675                 680                 685

Gly Thr Ser Gly Asp Phe Glu Gln Ala Lys Lys Ile Phe Asp Gly Glu
690                 695                 700

Lys Ser Asp Arg Phe Phe Thr Trp Gly Gln Thr Asn Trp Ile Ala Phe
705                 710                 715                 720

Asp Leu Gly Glu Ile Asn Leu Ala Lys Glu Trp Arg Leu Phe Asn Ala
            725                 730                 735

Glu Thr Asn Thr Glu Ile Lys Thr Asp Ser Ser Leu Asn Val Ala Lys
        740                 745                 750

Gly Arg Leu Gln Ile Leu Lys Asp Thr Thr Ile Asp Leu Glu Lys Met
    755                 760                 765

Asp Ile Lys Asn Arg Lys Glu Tyr Leu Ser Asn Asp Glu Asn Trp Thr
770                 775                 780

Asp Val Ala Gln Met Asp Asp Ala Lys Ala Ile Phe Asn Ser Lys Leu
785                 790                 795                 800

Ser Asn Val Leu Ser Arg Tyr Trp Arg Phe Cys Val Asp Gly Gly Ala
            805                 810                 815

Ser Ser Tyr Tyr Pro Gln Tyr Thr Glu Leu Gln Ile Leu Gly Gln Arg
        820                 825                 830

Leu Ser Asn Asp Val Ala Asn Thr Leu Asp
        835                 840

<210> SEQ ID NO 12
<211> LENGTH: 842
<212> TYPE: PRT
<213> ORGANISM: Artificial Sequence
<220> FEATURE:
<223> OTHER INFORMATION: Synthetic

<400> SEQUENCE: 12

Met Asp Lys His Leu Leu Val Lys Arg Thr Leu Gly Cys Val Cys Ala
1               5                   10                  15

Ala Thr Leu Met Gly Ala Ala Leu Ala Thr His His Asp Ser Leu Asn
            20                  25                  30

Thr Val Lys Ala Glu Glu Lys Thr Val Gln Thr Gly Lys Thr Asp Gln
        35                  40                  45

Gln Val Gly Ala Lys Leu Val Gln Glu Ile Arg Glu Gly Lys Arg Gly
    50                  55                  60

Pro Leu Tyr Ala Gly Tyr Phe Arg Thr Trp His Asp Arg Ala Ser Thr
65                  70                  75                  80

Gly Ile Asp Gly Lys Gln Gln His Pro Glu Asn Thr Met Ala Glu Val
            85                  90                  95

Pro Lys Glu Val Asp Ile Leu Phe Val Phe His Asp His Thr Ala Ser
        100                 105                 110

Asp Ser Pro Phe Trp Ser Glu Leu Lys Asp Ser Tyr Val His Lys Leu
    115                 120                 125

His Gln Gln Gly Thr Ala Leu Val Gln Met Ile Gly Val Asn Glu Leu
130                 135                 140

```
Asn Gly Arg Thr Gly Leu Ser Lys Asp Tyr Pro Asp Thr Pro Glu Gly
145                 150                 155                 160

Asn Lys Ala Leu Ala Ala Ile Val Lys Ala Phe Val Thr Asp Arg
                165                 170                 175

Gly Val Asp Gly Leu Asp Ile Asp Ile Glu His Glu Phe Thr Asn Lys
                180                 185                 190

Arg Thr Pro Glu Glu Asp Ala Arg Ala Leu Asn Val Phe Lys Glu Ile
            195                 200                 205

Ala Gln Leu Ile Gly Lys Asn Gly Ser Asp Lys Ser Lys Leu Leu Ile
    210                 215                 220

Met Asp Thr Thr Leu Ser Val Glu Asn Asn Pro Ile Phe Lys Gly Ile
225                 230                 235                 240

Ala Glu Asp Leu Asp Tyr Leu Leu Arg Gln Tyr Tyr Gly Ser Gln Gly
                245                 250                 255

Gly Glu Ala Glu Val Asp Thr Ile Asn Ser Asp Trp Asn Gln Tyr Gln
                260                 265                 270

Asn Tyr Ile Asp Ala Ser Gln Phe Met Ile Gly Phe Ser Phe Phe Glu
            275                 280                 285

Glu Ser Ala Ser Lys Gly Asn Leu Trp Phe Asp Val Asn Glu Tyr Asp
    290                 295                 300

Pro Asn Asn Pro Glu Lys Gly Lys Asp Ile Glu Gly Thr Arg Ala Lys
305                 310                 315                 320

Lys Tyr Ala Glu Trp Gln Pro Ser Thr Gly Gly Leu Lys Ala Gly Ile
                325                 330                 335

Phe Ser Tyr Ala Ile Asp Arg Asp Gly Val Ala His Val Pro Ser Thr
                340                 345                 350

Tyr Lys Asn Arg Thr Ser Thr Asn Leu Gln Arg His Glu Val Asp Asn
            355                 360                 365

Ile Ser His Thr Asp Tyr Thr Val Ser Arg Lys Leu Lys Thr Leu Met
    370                 375                 380

Thr Glu Asp Lys Arg Tyr Asp Val Ile Asp Gln Lys Asp Ile Pro Asp
385                 390                 395                 400

Pro Ala Leu Arg Glu Gln Ile Ile Gln Gln Val Gly Gln Tyr Lys Gly
                405                 410                 415

Asp Leu Glu Arg Tyr Asn Lys Thr Leu Val Leu Thr Gly Asp Lys Ile
            420                 425                 430

Gln Asn Leu Lys Gly Leu Glu Lys Leu Ser Lys Leu Gln Lys Leu Glu
    435                 440                 445

Leu Arg Gln Leu Ser Asn Val Lys Glu Ile Thr Pro Glu Leu Leu Pro
    450                 455                 460

Glu Ser Met Lys Lys Asp Ala Glu Leu Val Met Val Gly Met Thr Gly
465                 470                 475                 480

Leu Glu Lys Leu Asn Leu Ser Gly Leu Asn Arg Gln Thr Leu Asp Gly
                485                 490                 495

Ile Asp Val Asn Ser Ile Thr His Leu Thr Ser Phe Asp Ile Ser His
                500                 505                 510

Asn Ser Leu Asp Leu Ser Glu Lys Ser Glu Asp Arg Lys Leu Leu Met
            515                 520                 525

Thr Leu Met Glu Gln Val Ser Asn His Gln Lys Ile Thr Val Lys Asn
    530                 535                 540

Thr Ala Phe Glu Asn Gln Lys Pro Lys Gly Tyr Tyr Pro Gln Thr Tyr
545                 550                 555                 560

Asp Thr Lys Glu Gly His Tyr Asp Val Asp Asn Ala Glu His Asp Ile
```

```
            565                 570                 575
Leu Thr Asp Phe Val Phe Gly Thr Val Thr Lys Arg Asn Thr Phe Ile
            580                 585                 590

Gly Asp Glu Glu Ala Phe Ala Ile Tyr Lys Glu Gly Ala Val Asp Gly
            595                 600                 605

Arg Gln Tyr Val Ser Lys Asp Tyr Thr Tyr Glu Ala Phe Arg Lys Asp
            610                 615                 620

Tyr Lys Gly Tyr Lys Val His Leu Thr Ala Ser Asn Leu Gly Glu Thr
625                 630                 635                 640

Val Thr Ser Lys Val Thr Ala Thr Thr Asp Glu Thr Tyr Leu Val Asp
                    645                 650                 655

Val Ser Asp Gly Glu Lys Val Val His His Met Lys Leu Asn Ile Gly
                    660                 665                 670

Ser Gly Ala Ile Met Met Glu Asn Leu Ala Lys Gly Ala Lys Val Ile
                    675                 680                 685

Gly Thr Ser Gly Asp Phe Glu Gln Ala Lys Lys Ile Phe Asp Gly Glu
                    690                 695                 700

Lys Ser Asp Arg Phe Phe Thr Trp Gly Gln Thr Asn Trp Ile Ala Phe
705                 710                 715                 720

Asp Leu Gly Glu Ile Asn Leu Ala Lys Glu Trp Arg Leu Phe Asn Ala
                    725                 730                 735

Glu Thr Asn Thr Glu Ile Lys Thr Asp Ser Ser Leu Asn Val Ala Lys
                    740                 745                 750

Gly Arg Leu Gln Ile Leu Lys Asp Thr Thr Ile Asp Leu Glu Lys Met
                    755                 760                 765

Asp Ile Lys Asn Arg Lys Glu Tyr Leu Ser Asn Asp Glu Asn Trp Thr
770                 775                 780

Asp Val Ala Gln Met Asp Asp Ala Lys Ala Ile Phe Asn Ser Lys Leu
785                 790                 795                 800

Ser Asn Val Leu Ser Arg Tyr Trp Arg Phe Cys Val Asp Gly Gly Ala
                    805                 810                 815

Ser Ser Tyr Tyr Pro Gln Tyr Thr Glu Leu Gln Ile Leu Gly Gln Arg
                    820                 825                 830

Leu Ser Asn Asp Val Ala Asn Thr Leu Asp
                    835                 840
```

<210> SEQ ID NO 13
<211> LENGTH: 842
<212> TYPE: PRT
<213> ORGANISM: Artificial Sequence
<220> FEATURE:
<223> OTHER INFORMATION: Synthetic

<400> SEQUENCE: 13

```
Met Asp Lys His Leu Leu Val Lys Arg Thr Leu Gly Cys Val Cys Ala
1               5                   10                  15

Ala Thr Leu Met Gly Ala Ala Leu Ala Thr His His Asp Ser Leu Asn
                20                  25                  30

Thr Val Lys Ala Glu Glu Lys Thr Val Gln Thr Gly Lys Thr Asp Gln
                35                  40                  45

Gln Val Gly Ala Lys Leu Val Gln Glu Ile Arg Glu Gly Lys Arg Gly
            50                  55                  60

Pro Leu Tyr Ala Gly Tyr Phe Arg Thr Trp His Asp Arg Ala Ser Thr
65                  70                  75                  80

Gly Ile Asp Gly Lys Gln Gln His Pro Glu Asn Thr Met Ala Glu Val
```

```
            85                  90                  95
Pro Lys Glu Val Asp Ile Leu Phe Val Phe His Asp His Thr Ala Ser
            100                 105                 110

Asp Ser Pro Phe Trp Ser Glu Leu Lys Asp Ser Tyr Val His Lys Leu
            115                 120                 125

His Gln Gln Gly Thr Ala Leu Val Gln Asn Ile Gly Val Asn Glu Leu
            130                 135                 140

Asn Gly Arg Thr Gly Leu Ser Lys Asp Tyr Pro Asp Thr Pro Glu Gly
145                 150                 155                 160

Asn Lys Ala Leu Ala Ala Ile Val Lys Ala Phe Val Thr Asp Arg
            165                 170                 175

Gly Val Asp Gly Leu Asp Ile Asp Ile Glu His Glu Phe Thr Asn Lys
            180                 185                 190

Arg Thr Pro Glu Glu Asp Ala Arg Ala Leu Asn Val Phe Lys Glu Ile
            195                 200                 205

Ala Gln Leu Ile Gly Lys Asn Gly Ser Asp Lys Ser Lys Leu Leu Ile
            210                 215                 220

Met Asp Thr Thr Leu Ser Val Glu Asn Asn Pro Ile Phe Lys Gly Ile
225                 230                 235                 240

Ala Glu Asp Leu Asp Tyr Leu Leu Arg Gln Tyr Tyr Gly Ser Gln Gly
            245                 250                 255

Gly Glu Ala Glu Val Asp Thr Ile Asn Ser Asp Trp Asn Gln Tyr Gln
            260                 265                 270

Asn Tyr Ile Asp Ala Ser Gln Phe Met Ile Gly Phe Ser Phe Phe Glu
            275                 280                 285

Glu Ser Ala Ser Lys Gly Asn Leu Trp Phe Asp Val Asn Glu Tyr Asp
            290                 295                 300

Pro Asn Asn Pro Glu Lys Gly Lys Asp Ile Glu Gly Thr Arg Ala Lys
305                 310                 315                 320

Lys Tyr Ala Glu Trp Gln Pro Ser Thr Gly Gly Leu Lys Ala Gly Ile
            325                 330                 335

Phe Ser Tyr Ala Ile Asp Arg Asp Gly Val Ala His Val Pro Ser Thr
            340                 345                 350

Tyr Lys Asn Arg Thr Ser Thr Asn Leu Gln Arg His Glu Val Asp Asn
            355                 360                 365

Ile Ser His Thr Asp Tyr Thr Val Ser Arg Lys Leu Lys Thr Leu Met
            370                 375                 380

Thr Glu Asp Lys Arg Tyr Asp Val Ile Asp Gln Lys Asp Ile Pro Asp
385                 390                 395                 400

Pro Ala Leu Arg Glu Gln Ile Ile Gln Val Gly Gln Tyr Lys Gly
            405                 410                 415

Asp Leu Glu Arg Tyr Asn Lys Thr Leu Val Leu Thr Gly Asp Lys Ile
            420                 425                 430

Gln Asn Leu Lys Gly Leu Glu Lys Leu Ser Lys Leu Gln Lys Leu Glu
            435                 440                 445

Leu Arg Gln Leu Ser Asn Val Lys Glu Ile Thr Pro Glu Leu Leu Pro
            450                 455                 460

Glu Ser Met Lys Lys Asp Ala Glu Leu Val Met Val Gly Met Thr Gly
465                 470                 475                 480

Leu Glu Lys Leu Asn Leu Ser Gly Leu Asn Arg Gln Thr Leu Asp Gly
            485                 490                 495

Ile Asp Val Asn Ser Ile Thr His Leu Thr Ser Phe Asp Ile Ser His
            500                 505                 510
```

Asn Ser Leu Asp Leu Ser Glu Lys Ser Glu Asp Arg Lys Leu Leu Met
             515                 520                 525

Thr Leu Met Glu Gln Val Ser Asn His Gln Lys Ile Thr Val Lys Asn
        530                 535                 540

Thr Ala Phe Glu Asn Gln Lys Pro Lys Gly Tyr Tyr Pro Gln Thr Tyr
545                 550                 555                 560

Asp Thr Lys Glu Gly His Tyr Asp Val Asp Asn Ala Glu His Asp Ile
             565                 570                 575

Leu Thr Asp Phe Val Phe Gly Thr Val Thr Lys Arg Asn Thr Phe Ile
             580                 585                 590

Gly Asp Glu Glu Ala Phe Ala Ile Tyr Lys Glu Gly Ala Val Asp Gly
             595                 600                 605

Arg Gln Tyr Val Ser Lys Asp Tyr Thr Tyr Glu Ala Phe Arg Lys Asp
        610                 615                 620

Tyr Lys Gly Tyr Lys Val His Leu Thr Ala Ser Asn Leu Gly Glu Thr
625                 630                 635                 640

Val Thr Ser Lys Val Thr Ala Thr Asp Glu Thr Tyr Leu Val Asp
             645                 650                 655

Val Ser Asp Gly Glu Lys Val Val His His Met Lys Leu Asn Ile Gly
             660                 665                 670

Ser Gly Ala Ile Met Met Glu Asn Leu Ala Lys Gly Ala Lys Val Ile
        675                 680                 685

Gly Thr Ser Gly Asp Phe Glu Gln Ala Lys Lys Ile Phe Asp Gly Glu
        690                 695                 700

Lys Ser Asp Arg Phe Phe Thr Trp Gly Gln Thr Asn Trp Ile Ala Phe
705                 710                 715                 720

Asp Leu Gly Glu Ile Asn Leu Ala Lys Glu Trp Arg Leu Phe Asn Ala
             725                 730                 735

Glu Thr Asn Thr Glu Ile Lys Thr Asp Ser Ser Leu Asn Val Ala Lys
             740                 745                 750

Gly Arg Leu Gln Ile Leu Lys Asp Thr Thr Ile Asp Leu Glu Lys Met
        755                 760                 765

Asp Ile Lys Asn Arg Lys Glu Tyr Leu Ser Asn Asp Glu Asn Trp Thr
770                 775                 780

Asp Val Ala Gln Met Asp Asp Ala Lys Ala Ile Phe Asn Ser Lys Leu
785                 790                 795                 800

Ser Asn Val Leu Ser Arg Tyr Trp Arg Phe Cys Val Asp Gly Gly Ala
             805                 810                 815

Ser Ser Tyr Tyr Pro Gln Tyr Thr Glu Leu Gln Ile Leu Gly Gln Arg
             820                 825                 830

Leu Ser Asn Asp Val Ala Asn Thr Leu Asp
        835                 840

<210> SEQ ID NO 14
<211> LENGTH: 842
<212> TYPE: PRT
<213> ORGANISM: Artificial Sequence
<220> FEATURE:
<223> OTHER INFORMATION: Synthetic

<400> SEQUENCE: 14

Met Asp Lys His Leu Leu Val Lys Arg Thr Leu Gly Cys Val Cys Ala
1               5                   10                  15

Ala Thr Leu Met Gly Ala Ala Leu Ala Thr His His Asp Ser Leu Asn
            20                  25                  30

-continued

```
Thr Val Lys Ala Glu Lys Thr Val Gln Thr Gly Lys Thr Asp Gln
         35                  40                  45

Gln Val Gly Ala Lys Leu Val Gln Glu Ile Arg Glu Gly Lys Arg Gly
     50                  55                  60

Pro Leu Tyr Ala Gly Tyr Phe Arg Thr Trp His Asp Arg Ala Ser Thr
 65                  70                  75                  80

Gly Ile Asp Gly Lys Gln Gln His Pro Glu Asn Thr Met Ala Glu Val
                 85                  90                  95

Pro Lys Glu Val Asp Ile Leu Phe Val Phe His Asp His Thr Ala Ser
                100                 105                 110

Asp Ser Pro Phe Trp Ser Glu Leu Lys Asp Ser Tyr Val His Lys Leu
            115                 120                 125

His Gln Gln Gly Thr Ala Leu Val Gln Ile Gly Val Asn Glu Leu
        130                 135                 140

Asn Gly Arg Thr Gly Leu Ser Lys Asp Tyr Pro Asp Thr Pro Glu Gly
145                 150                 155                 160

Asn Lys Ala Leu Ala Ala Ile Val Lys Ala Phe Val Thr Asp Arg
                165                 170                 175

Gly Val Asp Gly Leu Asp Ile Asp Ile Glu His Glu Phe Thr Asn Lys
                180                 185                 190

Arg Thr Pro Glu Glu Asp Ala Arg Ala Leu Asn Val Phe Lys Glu Ile
            195                 200                 205

Ala Gln Leu Ile Gly Lys Asn Gly Ser Asp Lys Ser Lys Leu Leu Ile
        210                 215                 220

Met Asp Thr Thr Leu Ser Val Glu Asn Asn Pro Ile Phe Lys Gly Ile
225                 230                 235                 240

Ala Glu Asp Leu Asp Tyr Leu Leu Arg Gln Tyr Tyr Gly Ser Gln Gly
                245                 250                 255

Gly Glu Ala Glu Val Asp Thr Ile Asn Ser Asp Trp Asn Gln Tyr Gln
            260                 265                 270

Asn Tyr Ile Asp Ala Ser Gln Phe Met Ile Gly Phe Ser Phe Glu
        275                 280                 285

Glu Ser Ala Ser Lys Gly Asn Leu Trp Phe Asp Val Asn Glu Tyr Asp
        290                 295                 300

Pro Asn Asn Pro Glu Lys Gly Lys Asp Ile Glu Gly Thr Arg Ala Lys
305                 310                 315                 320

Lys Tyr Ala Glu Trp Gln Pro Ser Thr Gly Gly Leu Lys Ala Gly Ile
                325                 330                 335

Phe Ser Tyr Ala Ile Asp Arg Asp Gly Val Ala His Val Pro Ser Thr
            340                 345                 350

Tyr Lys Asn Arg Thr Ser Thr Asn Leu Gln Arg His Glu Val Asp Asn
        355                 360                 365

Ile Ser His Thr Asp Tyr Thr Val Ser Arg Lys Leu Lys Thr Leu Met
    370                 375                 380

Thr Glu Asp Lys Arg Tyr Asp Val Ile Asp Gln Lys Asp Ile Pro Asp
385                 390                 395                 400

Pro Ala Leu Arg Glu Gln Ile Ile Gln Val Gly Gln Tyr Lys Gly
                405                 410                 415

Asp Leu Glu Arg Tyr Asn Lys Thr Leu Val Leu Thr Gly Asp Lys Ile
            420                 425                 430

Gln Asn Leu Lys Gly Leu Glu Lys Leu Ser Lys Leu Gln Lys Leu Glu
        435                 440                 445
```

```
Leu Arg Gln Leu Ser Asn Val Lys Glu Ile Thr Pro Glu Leu Leu Pro
450                 455                 460

Glu Ser Met Lys Lys Asp Ala Glu Leu Val Met Val Gly Met Thr Gly
465                 470                 475                 480

Leu Glu Lys Leu Asn Leu Ser Gly Leu Asn Arg Gln Thr Leu Asp Gly
                485                 490                 495

Ile Asp Val Asn Ser Ile Thr His Leu Thr Ser Phe Asp Ile Ser His
                500                 505                 510

Asn Ser Leu Asp Leu Ser Glu Lys Ser Glu Asp Arg Lys Leu Leu Met
                515                 520                 525

Thr Leu Met Glu Gln Val Ser Asn His Gln Lys Ile Thr Val Lys Asn
530                 535                 540

Thr Ala Phe Glu Asn Gln Lys Pro Lys Gly Tyr Tyr Pro Gln Thr Tyr
545                 550                 555                 560

Asp Thr Lys Glu Gly His Tyr Asp Val Asp Asn Ala Glu His Asp Ile
                565                 570                 575

Leu Thr Asp Phe Val Phe Gly Thr Val Thr Lys Arg Asn Thr Phe Ile
                580                 585                 590

Gly Asp Glu Glu Ala Phe Ala Ile Tyr Lys Glu Gly Ala Val Asp Gly
                595                 600                 605

Arg Gln Tyr Val Ser Lys Asp Tyr Thr Tyr Glu Ala Phe Arg Lys Asp
                610                 615                 620

Tyr Lys Gly Tyr Lys Val His Leu Thr Ala Ser Asn Leu Gly Glu Thr
625                 630                 635                 640

Val Thr Ser Lys Val Thr Ala Thr Thr Asp Glu Thr Tyr Leu Val Asp
                645                 650                 655

Val Ser Asp Gly Glu Lys Val Val His His Met Lys Leu Asn Ile Gly
                660                 665                 670

Ser Gly Ala Ile Met Met Glu Asn Leu Ala Lys Gly Ala Lys Val Ile
                675                 680                 685

Gly Thr Ser Gly Asp Phe Glu Gln Ala Lys Lys Ile Phe Asp Gly Glu
                690                 695                 700

Lys Ser Asp Arg Phe Phe Thr Trp Gly Gln Thr Asn Trp Ile Ala Phe
705                 710                 715                 720

Asp Leu Gly Glu Ile Asn Leu Ala Lys Glu Trp Arg Leu Phe Asn Ala
                725                 730                 735

Glu Thr Asn Thr Glu Ile Lys Thr Asp Ser Ser Leu Asn Val Ala Lys
                740                 745                 750

Gly Arg Leu Gln Ile Leu Lys Asp Thr Thr Ile Asp Leu Glu Lys Met
                755                 760                 765

Asp Ile Lys Asn Arg Lys Glu Tyr Leu Ser Asn Asp Glu Asn Trp Thr
770                 775                 780

Asp Val Ala Gln Met Asp Asp Ala Lys Ala Ile Phe Asn Ser Lys Leu
785                 790                 795                 800

Ser Asn Val Leu Ser Arg Tyr Trp Arg Phe Cys Val Asp Gly Gly Ala
                805                 810                 815

Ser Ser Tyr Tyr Pro Gln Tyr Thr Glu Leu Gln Ile Leu Gly Gln Arg
                820                 825                 830

Leu Ser Asn Asp Val Ala Asn Thr Leu Asp
                835                 840

<210> SEQ ID NO 15
<211> LENGTH: 842
<212> TYPE: PRT
```

<213> ORGANISM: Artificial Sequence
<220> FEATURE:
<223> OTHER INFORMATION: Synthetic

<400> SEQUENCE: 15

```
Met Asp Lys His Leu Leu Val Lys Arg Thr Leu Gly Cys Val Cys Ala
1               5                   10                  15

Ala Thr Leu Met Gly Ala Ala Leu Ala Thr His His Asp Ser Leu Asn
            20                  25                  30

Thr Val Lys Ala Glu Glu Lys Thr Val Gln Thr Gly Lys Thr Asp Gln
        35                  40                  45

Gln Val Gly Ala Lys Leu Val Gln Glu Ile Arg Glu Gly Lys Arg Gly
    50                  55                  60

Pro Leu Tyr Ala Gly Tyr Phe Arg Thr Trp His Asp Arg Ala Ser Thr
65                  70                  75                  80

Gly Ile Asp Gly Lys Gln Gln His Pro Glu Asn Thr Met Ala Glu Val
                85                  90                  95

Pro Lys Glu Val Asp Ile Leu Phe Val Phe His Asp Thr Ala Ser
            100                 105                 110

Asp Ser Pro Phe Trp Ser Glu Leu Lys Asp Ser Tyr Val His Lys Leu
        115                 120                 125

His Gln Gln Gly Thr Ala Leu Val Gln Arg Ile Gly Val Asn Glu Leu
    130                 135                 140

Asn Gly Arg Thr Gly Leu Ser Lys Asp Tyr Pro Asp Thr Pro Glu Gly
145                 150                 155                 160

Asn Lys Ala Leu Ala Ala Ile Val Lys Ala Phe Val Thr Asp Arg
                165                 170                 175

Gly Val Asp Gly Leu Asp Ile Asp Ile Glu His Glu Phe Thr Asn Lys
        180                 185                 190

Arg Thr Pro Glu Glu Asp Ala Arg Ala Leu Asn Val Phe Lys Glu Ile
    195                 200                 205

Ala Gln Leu Ile Gly Lys Asn Gly Ser Asp Lys Ser Lys Leu Leu Ile
210                 215                 220

Met Asp Thr Thr Leu Ser Val Glu Asn Asn Pro Ile Phe Lys Gly Ile
225                 230                 235                 240

Ala Glu Asp Leu Asp Tyr Leu Leu Arg Gln Tyr Tyr Gly Ser Gln Gly
                245                 250                 255

Gly Glu Ala Glu Val Asp Thr Ile Asn Ser Asp Trp Asn Gln Tyr Gln
        260                 265                 270

Asn Tyr Ile Asp Ala Ser Gln Phe Met Ile Gly Phe Ser Phe Phe Glu
    275                 280                 285

Glu Ser Ala Ser Lys Gly Asn Leu Trp Phe Asp Val Asn Glu Tyr Asp
290                 295                 300

Pro Asn Asn Pro Glu Lys Gly Lys Asp Ile Glu Gly Thr Arg Ala Lys
305                 310                 315                 320

Lys Tyr Ala Glu Trp Gln Pro Ser Thr Gly Gly Leu Lys Ala Gly Ile
                325                 330                 335

Phe Ser Tyr Ala Ile Asp Arg Asp Gly Val Ala His Val Pro Ser Thr
        340                 345                 350

Tyr Lys Asn Arg Thr Ser Thr Asn Leu Gln Arg His Glu Val Asp Asn
    355                 360                 365

Ile Ser His Thr Asp Tyr Thr Val Ser Arg Lys Leu Lys Thr Leu Met
370                 375                 380

Thr Glu Asp Lys Arg Tyr Asp Val Ile Asp Gln Lys Asp Ile Pro Asp
```

```
                    385                 390                 395                 400
Pro Ala Leu Arg Glu Gln Ile Ile Gln Gln Val Gly Gln Tyr Lys Gly
                405                 410                 415

Asp Leu Glu Arg Tyr Asn Lys Thr Leu Val Leu Thr Gly Asp Lys Ile
                420                 425                 430

Gln Asn Leu Lys Gly Leu Glu Lys Leu Ser Lys Leu Gln Lys Leu Glu
                435                 440                 445

Leu Arg Gln Leu Ser Asn Val Lys Glu Ile Thr Pro Glu Leu Leu Pro
            450                 455                 460

Glu Ser Met Lys Lys Asp Ala Glu Leu Val Met Val Gly Met Thr Gly
465                 470                 475                 480

Leu Glu Lys Leu Asn Leu Ser Gly Leu Asn Arg Gln Thr Leu Asp Gly
                485                 490                 495

Ile Asp Val Asn Ser Ile Thr His Leu Thr Ser Phe Asp Ile Ser His
                500                 505                 510

Asn Ser Leu Asp Leu Ser Glu Lys Ser Glu Asp Arg Lys Leu Leu Met
            515                 520                 525

Thr Leu Met Glu Gln Val Ser Asn His Gln Lys Ile Thr Val Lys Asn
            530                 535                 540

Thr Ala Phe Glu Asn Gln Lys Pro Lys Gly Tyr Tyr Pro Gln Thr Tyr
545                 550                 555                 560

Asp Thr Lys Glu Gly His Tyr Asp Val Asp Asn Ala Glu His Asp Ile
                565                 570                 575

Leu Thr Asp Phe Val Phe Gly Thr Val Thr Lys Arg Asn Thr Phe Ile
                580                 585                 590

Gly Asp Glu Glu Ala Phe Ala Ile Tyr Lys Glu Gly Ala Val Asp Gly
            595                 600                 605

Arg Gln Tyr Val Ser Lys Asp Tyr Thr Tyr Glu Ala Phe Arg Lys Asp
            610                 615                 620

Tyr Lys Gly Tyr Lys Val His Leu Thr Ala Ser Asn Leu Gly Glu Thr
625                 630                 635                 640

Val Thr Ser Lys Val Thr Ala Thr Thr Asp Glu Thr Tyr Leu Val Asp
                645                 650                 655

Val Ser Asp Gly Glu Lys Val Val His His Met Lys Leu Asn Ile Gly
                660                 665                 670

Ser Gly Ala Ile Met Met Glu Asn Leu Ala Lys Gly Ala Lys Val Ile
            675                 680                 685

Gly Thr Ser Gly Asp Phe Glu Gln Ala Lys Lys Ile Phe Asp Gly Glu
            690                 695                 700

Lys Ser Asp Arg Phe Phe Thr Trp Gly Gln Thr Asn Trp Ile Ala Phe
705                 710                 715                 720

Asp Leu Gly Glu Ile Asn Leu Ala Lys Glu Trp Arg Leu Phe Asn Ala
                725                 730                 735

Glu Thr Asn Thr Glu Ile Lys Thr Asp Ser Ser Leu Asn Val Ala Lys
                740                 745                 750

Gly Arg Leu Gln Ile Leu Lys Asp Thr Thr Ile Asp Leu Glu Lys Met
            755                 760                 765

Asp Ile Lys Asn Arg Lys Glu Tyr Leu Ser Asp Glu Asn Trp Thr
            770                 775                 780

Asp Val Ala Gln Met Asp Asp Ala Lys Ala Ile Phe Asn Ser Lys Leu
785                 790                 795                 800

Ser Asn Val Leu Ser Arg Tyr Trp Arg Phe Cys Val Asp Gly Gly Ala
                805                 810                 815
```

```
Ser Ser Tyr Tyr Pro Gln Tyr Thr Glu Leu Gln Ile Leu Gly Gln Arg
            820                 825                 830

Leu Ser Asn Asp Val Ala Asn Thr Leu Asp
835                 840

<210> SEQ ID NO 16
<211> LENGTH: 842
<212> TYPE: PRT
<213> ORGANISM: Artificial Sequence
<220> FEATURE:
<223> OTHER INFORMATION: Synthetic

<400> SEQUENCE: 16

Met Asp Lys His Leu Leu Val Lys Arg Thr Leu Gly Cys Val Cys Ala
1               5                   10                  15

Ala Thr Leu Met Gly Ala Ala Leu Ala Thr His His Asp Ser Leu Asn
            20                  25                  30

Thr Val Lys Ala Glu Glu Lys Thr Val Gln Thr Gly Lys Thr Asp Gln
        35                  40                  45

Gln Val Gly Ala Lys Leu Val Gln Glu Ile Arg Glu Gly Lys Arg Gly
    50                  55                  60

Pro Leu Tyr Ala Gly Tyr Phe Arg Thr Trp His Asp Arg Ala Ser Thr
65                  70                  75                  80

Gly Ile Asp Gly Lys Gln Gln His Pro Glu Asn Thr Met Ala Glu Val
                85                  90                  95

Pro Lys Glu Val Asp Ile Leu Phe Val Phe His Asp His Thr Ala Ser
            100                 105                 110

Asp Ser Pro Phe Trp Ser Glu Leu Lys Asp Ser Tyr Val His Lys Leu
        115                 120                 125

His Gln Gln Gly Thr Ala Leu Val Gln Val Ile Gly Val Asn Glu Leu
    130                 135                 140

Asn Gly Arg Thr Gly Leu Ser Lys Asp Tyr Pro Asp Thr Pro Glu Gly
145                 150                 155                 160

Asn Lys Ala Leu Ala Ala Ala Ile Val Lys Ala Phe Val Thr Asp Arg
                165                 170                 175

Gly Val Asp Gly Leu Asp Ile Asp Ile Glu His Glu Phe Thr Asn Lys
            180                 185                 190

Arg Thr Pro Glu Glu Asp Ala Arg Ala Leu Asn Val Phe Lys Glu Ile
        195                 200                 205

Ala Gln Leu Ile Gly Lys Asn Gly Ser Asp Lys Ser Lys Leu Leu Ile
    210                 215                 220

Met Asp Thr Thr Leu Ser Val Glu Asn Asn Pro Ile Phe Lys Gly Ile
225                 230                 235                 240

Ala Glu Asp Leu Asp Tyr Leu Leu Arg Gln Tyr Tyr Gly Ser Gln Gly
                245                 250                 255

Gly Glu Ala Glu Val Asp Thr Ile Asn Ser Asp Trp Asn Gln Tyr Gln
            260                 265                 270

Asn Tyr Ile Asp Ala Ser Gln Phe Met Ile Gly Phe Ser Phe Phe Glu
        275                 280                 285

Glu Ser Ala Ser Lys Gly Asn Leu Trp Phe Asp Val Asn Glu Tyr Asp
    290                 295                 300

Pro Asn Asn Pro Glu Lys Gly Lys Asp Ile Glu Gly Thr Arg Ala Lys
305                 310                 315                 320

Lys Tyr Ala Glu Trp Gln Pro Ser Thr Gly Gly Leu Lys Ala Gly Ile
                325                 330                 335
```

```
Phe Ser Tyr Ala Ile Asp Arg Asp Gly Val Ala His Val Pro Ser Thr
                340                 345                 350

Tyr Lys Asn Arg Thr Ser Thr Asn Leu Gln Arg His Glu Val Asp Asn
                355                 360                 365

Ile Ser His Thr Asp Tyr Thr Val Ser Arg Lys Leu Lys Thr Leu Met
            370                 375                 380

Thr Glu Asp Lys Arg Tyr Asp Val Ile Asp Gln Lys Asp Ile Pro Asp
385                 390                 395                 400

Pro Ala Leu Arg Glu Gln Ile Ile Gln Gln Val Gly Gln Tyr Lys Gly
                405                 410                 415

Asp Leu Glu Arg Tyr Asn Lys Thr Leu Val Leu Thr Gly Asp Lys Ile
                420                 425                 430

Gln Asn Leu Lys Gly Leu Glu Lys Leu Ser Lys Leu Gln Lys Leu Glu
            435                 440                 445

Leu Arg Gln Leu Ser Asn Val Lys Glu Ile Thr Pro Glu Leu Leu Pro
        450                 455                 460

Glu Ser Met Lys Lys Asp Ala Glu Leu Val Met Val Gly Met Thr Gly
465                 470                 475                 480

Leu Glu Lys Leu Asn Leu Ser Gly Leu Asn Arg Gln Thr Leu Asp Gly
                485                 490                 495

Ile Asp Val Asn Ser Ile Thr His Leu Thr Ser Phe Asp Ile Ser His
                500                 505                 510

Asn Ser Leu Asp Leu Ser Glu Lys Ser Glu Asp Arg Lys Leu Leu Met
            515                 520                 525

Thr Leu Met Glu Gln Val Ser Asn His Gln Lys Ile Thr Val Lys Asn
        530                 535                 540

Thr Ala Phe Glu Asn Gln Lys Pro Lys Gly Tyr Tyr Pro Gln Thr Tyr
545                 550                 555                 560

Asp Thr Lys Glu Gly His Tyr Asp Val Asp Asn Ala Glu His Asp Ile
                565                 570                 575

Leu Thr Asp Phe Val Phe Gly Thr Val Thr Lys Arg Asn Thr Phe Ile
            580                 585                 590

Gly Asp Glu Glu Ala Phe Ala Ile Tyr Lys Glu Gly Ala Val Asp Gly
        595                 600                 605

Arg Gln Tyr Val Ser Lys Asp Tyr Thr Tyr Glu Ala Phe Arg Lys Asp
        610                 615                 620

Tyr Lys Gly Tyr Lys Val His Leu Thr Ala Ser Asn Leu Gly Glu Thr
625                 630                 635                 640

Val Thr Ser Lys Val Thr Ala Thr Asp Glu Thr Tyr Leu Val Asp
                645                 650                 655

Val Ser Asp Gly Glu Lys Val His His Met Lys Leu Asn Ile Gly
            660                 665                 670

Ser Gly Ala Ile Met Met Glu Asn Leu Ala Lys Gly Ala Lys Val Ile
        675                 680                 685

Gly Thr Ser Gly Asp Phe Glu Gln Ala Lys Lys Ile Phe Asp Gly Glu
        690                 695                 700

Lys Ser Asp Arg Phe Phe Thr Trp Gly Gln Thr Asn Trp Ile Ala Phe
705                 710                 715                 720

Asp Leu Gly Glu Ile Asn Leu Ala Lys Glu Trp Arg Leu Phe Asn Ala
                725                 730                 735

Glu Thr Asn Thr Glu Ile Lys Thr Asp Ser Ser Leu Asn Val Ala Lys
                740                 745                 750
```

```
Gly Arg Leu Gln Ile Leu Lys Asp Thr Thr Ile Asp Leu Glu Lys Met
        755                 760                 765

Asp Ile Lys Asn Arg Lys Glu Tyr Leu Ser Asn Asp Glu Asn Trp Thr
770                 775                 780

Asp Val Ala Gln Met Asp Asp Ala Lys Ala Ile Phe Asn Ser Lys Leu
785                 790                 795                 800

Ser Asn Val Leu Ser Arg Tyr Trp Arg Phe Cys Val Asp Gly Gly Ala
                805                 810                 815

Ser Ser Tyr Tyr Pro Gln Tyr Thr Glu Leu Gln Ile Leu Gly Gln Arg
            820                 825                 830

Leu Ser Asn Asp Val Ala Asn Thr Leu Asp
        835                 840

<210> SEQ ID NO 17
<211> LENGTH: 842
<212> TYPE: PRT
<213> ORGANISM: Artificial Sequence
<220> FEATURE:
<223> OTHER INFORMATION: Synthetic

<400> SEQUENCE: 17

Met Asp Lys His Leu Leu Val Lys Arg Thr Leu Gly Cys Val Cys Ala
1               5                   10                  15

Ala Thr Leu Met Gly Ala Ala Leu Ala Thr His His Asp Ser Leu Asn
            20                  25                  30

Thr Val Lys Ala Glu Glu Lys Thr Val Gln Thr Gly Lys Thr Asp Gln
        35                  40                  45

Gln Val Gly Ala Lys Leu Val Gln Glu Ile Arg Glu Gly Lys Arg Gly
    50                  55                  60

Pro Leu Tyr Ala Gly Tyr Phe Arg Thr Trp His Asp Arg Ala Ser Thr
65                  70                  75                  80

Gly Ile Asp Gly Lys Gln Gln His Pro Glu Asn Thr Met Ala Glu Val
                85                  90                  95

Pro Lys Glu Val Asp Ile Leu Phe Val Phe His Asp His Thr Ala Ser
            100                 105                 110

Asp Ser Pro Phe Trp Ser Glu Leu Lys Asp Ser Tyr Val His Lys Leu
        115                 120                 125

His Gln Gln Gly Thr Ala Leu Val Gln Trp Ile Gly Val Asn Glu Leu
    130                 135                 140

Asn Gly Arg Thr Gly Leu Ser Lys Asp Tyr Pro Asp Thr Pro Glu Gly
145                 150                 155                 160

Asn Lys Ala Leu Ala Ala Ile Val Lys Ala Phe Val Thr Asp Arg
                165                 170                 175

Gly Val Asp Gly Leu Asp Ile Asp Ile Glu His Glu Phe Thr Asn Lys
            180                 185                 190

Arg Thr Pro Glu Glu Asp Ala Arg Ala Leu Asn Val Phe Lys Glu Ile
        195                 200                 205

Ala Gln Leu Ile Gly Lys Asn Gly Ser Asp Lys Ser Lys Leu Leu Ile
    210                 215                 220

Met Asp Thr Thr Leu Ser Val Glu Asn Pro Ile Phe Lys Gly Ile
225                 230                 235                 240

Ala Glu Asp Leu Asp Tyr Leu Leu Arg Gln Tyr Tyr Gly Ser Gln Gly
                245                 250                 255

Gly Glu Ala Glu Val Asp Thr Ile Asn Ser Asp Trp Asn Gln Tyr Gln
            260                 265                 270
```

```
Asn Tyr Ile Asp Ala Ser Gln Phe Met Ile Gly Phe Ser Phe Glu
        275                 280                 285
Glu Ser Ala Ser Lys Gly Asn Leu Trp Phe Asp Val Asn Glu Tyr Asp
290                 295                 300
Pro Asn Asn Pro Glu Lys Gly Lys Asp Ile Glu Gly Thr Arg Ala Lys
305                 310                 315                 320
Lys Tyr Ala Glu Trp Gln Pro Ser Thr Gly Gly Leu Lys Ala Gly Ile
                325                 330                 335
Phe Ser Tyr Ala Ile Asp Arg Asp Gly Val Ala His Val Pro Ser Thr
            340                 345                 350
Tyr Lys Asn Arg Thr Ser Thr Asn Leu Gln Arg His Glu Val Asp Asn
        355                 360                 365
Ile Ser His Thr Asp Tyr Thr Val Ser Arg Lys Leu Lys Thr Leu Met
    370                 375                 380
Thr Glu Asp Lys Arg Tyr Asp Val Ile Asp Gln Lys Asp Ile Pro Asp
385                 390                 395                 400
Pro Ala Leu Arg Glu Gln Ile Ile Gln Gln Val Gly Gln Tyr Lys Gly
                405                 410                 415
Asp Leu Glu Arg Tyr Asn Lys Thr Leu Val Leu Thr Gly Asp Lys Ile
            420                 425                 430
Gln Asn Leu Lys Gly Leu Glu Lys Leu Ser Lys Leu Gln Lys Leu Glu
        435                 440                 445
Leu Arg Gln Leu Ser Asn Val Lys Glu Ile Thr Pro Glu Leu Leu Pro
    450                 455                 460
Glu Ser Met Lys Lys Asp Ala Glu Leu Val Met Val Gly Met Thr Gly
465                 470                 475                 480
Leu Glu Lys Leu Asn Leu Ser Gly Leu Asn Arg Gln Thr Leu Asp Gly
                485                 490                 495
Ile Asp Val Asn Ser Ile Thr His Leu Thr Ser Phe Asp Ile Ser His
            500                 505                 510
Asn Ser Leu Asp Leu Ser Glu Lys Ser Glu Asp Arg Lys Leu Leu Met
        515                 520                 525
Thr Leu Met Glu Gln Val Ser Asn His Gln Lys Ile Thr Val Lys Asn
    530                 535                 540
Thr Ala Phe Glu Asn Gln Lys Pro Lys Gly Tyr Tyr Pro Gln Thr Tyr
545                 550                 555                 560
Asp Thr Lys Glu Gly His Tyr Asp Val Asp Asn Ala Glu His Asp Ile
                565                 570                 575
Leu Thr Asp Phe Val Phe Gly Thr Val Thr Lys Arg Asn Thr Phe Ile
            580                 585                 590
Gly Asp Glu Glu Ala Phe Ala Ile Tyr Lys Glu Gly Ala Val Asp Gly
        595                 600                 605
Arg Gln Tyr Val Ser Lys Asp Tyr Thr Tyr Glu Ala Phe Arg Lys Asp
    610                 615                 620
Tyr Lys Gly Tyr Lys Val His Leu Thr Ala Ser Asn Leu Gly Glu Thr
625                 630                 635                 640
Val Thr Ser Lys Val Thr Ala Thr Thr Asp Glu Thr Tyr Leu Val Asp
                645                 650                 655
Val Ser Asp Gly Glu Lys Val His His Met Lys Leu Asn Ile Gly
            660                 665                 670
Ser Gly Ala Ile Met Met Glu Asn Leu Ala Lys Gly Ala Lys Val Ile
        675                 680                 685
Gly Thr Ser Gly Asp Phe Glu Gln Ala Lys Lys Ile Phe Asp Gly Glu
```

```
              690                 695                 700
Lys Ser Asp Arg Phe Phe Thr Trp Gly Gln Thr Asn Trp Ile Ala Phe
705                 710                 715                 720

Asp Leu Gly Glu Ile Asn Leu Ala Lys Glu Trp Arg Leu Phe Asn Ala
                725                 730                 735

Glu Thr Asn Thr Glu Ile Lys Thr Asp Ser Ser Leu Asn Val Ala Lys
                740                 745                 750

Gly Arg Leu Gln Ile Leu Lys Asp Thr Thr Ile Asp Leu Glu Lys Met
                755                 760                 765

Asp Ile Lys Asn Arg Lys Glu Tyr Leu Ser Asn Asp Glu Asn Trp Thr
770                 775                 780

Asp Val Ala Gln Met Asp Asp Ala Lys Ala Ile Phe Asn Ser Lys Leu
785                 790                 795                 800

Ser Asn Val Leu Ser Arg Tyr Trp Arg Phe Cys Val Asp Gly Gly Ala
                805                 810                 815

Ser Ser Tyr Tyr Pro Gln Tyr Thr Glu Leu Gln Ile Leu Gly Gln Arg
                820                 825                 830

Leu Ser Asn Asp Val Ala Asn Thr Leu Asp
                835                 840

<210> SEQ ID NO 18
<211> LENGTH: 451
<212> TYPE: PRT
<213> ORGANISM: Artificial Sequence
<220> FEATURE:
<223> OTHER INFORMATION: Synthetic

<400> SEQUENCE: 18

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
                20                  25                  30

Asn Met His Trp Val Lys Gln Thr Pro Gly Arg Gly Leu Glu Trp Ile
            35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
                100                 105                 110

Ala Gly Thr Thr Val Thr Val Ser Ala Ala Ser Thr Lys Gly Pro Ser
            115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
```

```
Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
        260                 265                 270

Glu Asp Pro Glu Val Lys Phe Asn Trp Tyr Val Asp Gly Val Glu Val
    275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 19
<211> LENGTH: 212
<212> TYPE: PRT
<213> ORGANISM: Artificial Sequence
<220> FEATURE:
<223> OTHER INFORMATION: Synthetic

<400> SEQUENCE: 19

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Asn Leu Ala Ser Gly Val Pro Val Arg Phe Ser Gly Ser Gly
    50                  55                  60

Ser Gly Thr Ser Tyr Ser Leu Thr Ile Ser Arg Val Glu Ala Glu Asp
65                  70                  75                  80

Ala Ala Thr Tyr Tyr Cys Gln Gln Trp Thr Ser Asn Pro Pro Thr Phe
                85                  90                  95

Gly Gly Gly Thr Lys Leu Glu Ile Lys Arg Thr Val Ala Ala Pro Ser
            100                 105                 110

Val Phe Ile Phe Pro Pro Ser Asp Glu Gln Leu Lys Ser Gly Thr Ala
```

-continued

```
            115                 120                 125
Ser Val Val Cys Leu Leu Asn Asn Phe Tyr Pro Arg Glu Ala Lys Val
        130                 135                 140

Gln Trp Lys Val Asp Asn Ala Leu Gln Ser Gly Asn Ser Gln Glu Ser
145                 150                 155                 160

Val Thr Glu Gln Asp Ser Lys Asp Ser Thr Tyr Ser Leu Ser Ser Thr
                165                 170                 175

Leu Thr Leu Ser Lys Ala Asp Tyr Glu Lys His Lys Val Tyr Ala Cys
                180                 185                 190

Glu Val Thr His Gln Gly Leu Ser Ser Pro Val Thr Lys Ser Phe Asn
        195                 200                 205

Arg Gly Glu Cys
    210
```

METHODS FOR GLYCOPROTEIN REMODELING USING ENDOGLYCOSIDASE MUTANTS

CROSS REFERENCE TO RELATED APPLICATIONS

This claims the priority of U.S. Patent Application No. 62/378,806, filed on Aug. 24, 2016, the disclosure of which is incorporated by reference in its entirety.

BACKGROUND OF INVENTION

Field of the Invention

The present invention relates to selected mutants of endoglycosidase S2 (EndoS2) from *Streptococcus Pyogenes* that display improved transglycosylation activities and reduced hydrolyzing activities for the synthesis of glycoproteins or glycopeptides carrying a broad range of well-defined N-glycans of high mannose, hybrid and complex types. In particular, one or more embodiments of present invention also relate to use of EndoS2 mutants for efficient glycan remodeling of therapeutic antibodies to form homogenous glycan compositions at Fc-domain for improvement of their effector functions.

Background Art

Since the approval of the first therapeutic monoclonal antibody therapy in 1986, the commercial pipeline of this class of biopharmaceutical products have become most robust and dynamic (1). As of early 2015, a total of forty-seven monoclonal antibody products have been approved in the U.S. or Europe for the treatments of a variety of diseases, including cancer, autoimmune and infectious diseases. If it continues at the current approval rate, approximately 70 monoclonal antibody products will hit the market by 2020, and account for worldwide sales of nearly $125 billion (2). For monoclonal antibody therapeutics that depend on Fc-mediated effector functions for their clinical activities, the compositions of N-glycans at the Fc domains have been shown to be critical for safety or efficacy (3). Diverse glycosylation states have also been implicated to influence the pharmacodynamic and pharmacokinetic properties, while other Fc glycan structural elements may be involved in adverse immune reactions. However, the way to control the Fc-glycosylation remains challenging.

A typical IgG consists of two antigen-binding fragments (Fabs), which are connected via a flexible region to a constant region (Fc). The Fab domains are responsible for antigen recognition while the N-glycan at Asn297 of Fc domain interact with respective Fcγ receptors (such as FcγRIIIa and FcγRIIb) on effector cells and Clq component of the complements that activate the effector functions, including antibody-dependent cellular cytotoxicity (ADCC) and complement-dependent cytotoxicity (CDC) (5-7). Almost all therapeutic antibodies are N-glycosylated on each of the homodimeric Fc domains at the conserved asparagine residue (N297). These N-linked glycans result in more than 30 different glycoforms, and are typical bientennary complex type with considerable structural heterogeneity, in which the core heptasaccharide can be differentially decorated with core fucose (Fuc), bisecting N-acetylglucosamine (GlcNAc), terminal galactose (Gal), and terminal sialic acid (Sia) (8-9). The composition of N-glycans could influence the Fc domain conformation, therefore, modulating the antibody's stability, pharmacokinetic profile, immunogenicity, effector functions, antibody-mediated inflammation, and complement activation (10). For example, the absence of the core fucose, as well as the attachment of a bisecting GlcNAc moiety, dramatically enhances the affinity of antibody for the FcγIIIa receptor (FcγRIIIa) on effector cells, resulting in better elimination of the target (10-11). In addition, the terminal a-2,6-sialylated glycan, which is a minor component of antibodies and the intravenous immunoglobulin (IVIG), is an optimized structure that enhances the anti-inflammatory properties (12-13).

N-glycosylation is one of the most complex post-translational modifications that often result in a remarkable heterogeneity of glycan structures including high mannose, hybrid and complex types, depending on the recombinant expression system (14-15). Commercially available therapeutic antibodies typically exist as mixtures of glycoforms that are not optimal for their respective therapeutic activities. Recently, glycoengineering has gathered a huge attention to control Fc glycosylation for improving efficacy. One of the most common methods is the in vivo engineering of synthetic pathways on the expression host. However, the glycoforms generated by this method are limited, and total control over the desired glycoform cannot be achieved. An alternative way to address the glycosylation heterogeneity is endoglycosidases [endo-N-acetyl glucosaminidase (ENGase)] with or without fucosidase mediated trimming off all the heterogeneous N-glycans to leave only the first GlcNAc or Fuc-GlcNAc at the glycosylation site of IgGs and then a well-defined activated glycan in the form of oxazoline can be transferred back on GlcNAc acceptor to form a natural β-1,4 linkage (16).

Endoglycosidases, EndoS and EndoS2, are a family 18 glycoside hydrolase (GH) from the human pathogen *Streptococcus pyogenes* and have recently become the point of attention for glycoengineering of therapeutic antibodies (17-18). Despite their mere 37% sequence identity, both EndoS and EndoS2 catalyze the hydrolysis of the β-1, 4 linkage between the two N-acetylglucosamines (GlcNAcs) in the core of the N-linked glycan of human IgG. Additionally, both enzymes remove complex type glycans at IgG Fc domain. However, EndoS2 can hydrolyze hybrid and oligomannose structures to a greater extent, as compared with EndoS (19). Moreover, in the presence of sugar-oxazolines as substrates, some endoglycosidases of GH18 and GH85 turn into glycosynthases to catalyze chitobiose linkage. However, the intrinsic hydrolyitic activity of these glycosynthase enzymes reduces the overall yields.

Further improvement on enzyme activity leads to the development of endoglycosidase mutants, including EndoS mutants D233Q and D233A (16). This revelaed important motifs in the active site of ENGase: D-X-E in GH18. This motif supports the catalysis mechanism of ENGase, which uses a double-displacement reaction with neighboring group participation. In this mechanism, the 2-acetamide group of the GlcNAc acts as a nucleophile to replace the leaving group at the anomeric center, with the formation of an oxazolinium ion intermediate promoted by the carboxylate of Asp. The catalytic residue, glutamate, acted as a general acid/base that protonates the leaving aglycan group and deprotonates the nucleophilic $H_2O$ leading to the hydrolysis of the oxazolinium ion intermediate to form a hydrolytic product. The carboxylate of aspartate, second residues on the N-terminal sides of E, was proposed to promote and stabilize the formation of the oxazolinium ion intermediate. The D233Q mutation of EndoS was demonstrated to improve transglycosylation and diminish hydrolysis activity.

The above-described EndoS mutants are the best glycosynthase known so far. They have a great potential for the synthesis of homogeneous antibodies. However, a large amount of enzymes is usually require to achieve complete conversion of the starting material into a product. Therefore, the large scale production of enzymes and the downstream purification to remove residual enzyme content after reaction become tedious and labor intensive, which further attribute to the high cost of the overall glycoenginnering process. In addition, the transglycosylation activity of EndoS mutants is limited particularly to symmetric bi-antennary complex types glycoforms, but not towards a wide range of high mannose, hybrid and tri- and tetra-antennary complex type glycans having additional native modifications such as α-1,3-fucose on GlcNAc, α-1,2-fucose on Gal, extended poly LacNAc motifs, and asymmetric sialylated antennae at the termini.

Because of its potential to hydrolyze a broad range of IgG glycans, EndoS2 generated a huge interest in the IgG glycoengineering field. Based on the sequence alignment results of EndoS and EndoS2, it has been speculated that the site D184 of EndoS2 is identical to the site D233 of EndoS. Therefore, it is expected that the mutants format this site D184 of Endo S2 might enhance transglycosylation activity and diminish hydrolytic activity of EndoS2. In light of above-mentioned prior art, it would be advantageous to improve the glycosynthase activity of EndoS2 by site directed mutagenesis near the active site of the wild-type EndoS2. Provided herein are EndoS2 mutants having excellent glycosynthase activity and decreased hydrolyitic activity. More importantly, novel EndoS2 mutants of this invention offered broad substrate range, and able to transfer high mannose, hybrid and bi- and tri-antennary complex type N-glycans in the form activated glycan oxazolines. EndoS2 mutants of this invention facilitate production of diversely glycosylated homogeneous antibodies, particularly of those fully sialylated multi-antennary glycoforms that expected to gain anti-inflammatory activities, for biophysical and structural studies.

SUMMARY OF INVENTION

Embodiments of the present invention relates to selected mutants of EndoS2 that show reduced hydrolyzing activities and excellent transglycosylation activities against a broad range of N-glycans of high mannose, hybrid and complex types. These EndoS2 mutants may be used to prepare homogeneously glycosylated glycopeptides, glycoproteins, and therapeutic antibodies or Fc fragments thereof. Embodiments of the present invention allow for efficient glycan remodeling of therapeutic antibodies and Fc fragments thereof with high mannose, hybrid and complex type glycoforms at antibody-Fc regions. The glyco-engineered antibodies may result in enhancement of their effector functions, such as FcγIIIA bindings and antibody dependent cell mediated cytotoxicity (ADCC) etc., as well as pharmacological properties. In addition, embodiments of the present invention enable rapid investigation of effects of diverse Fc glycosylations of therapeutic antibodies, particularly of those highly sialylated complex type glycoforms that are expected to gain anti-inflammatory activities, on their effector functions.

In one aspect, the present invention provides the EndoS2 mutants, wherein the mutants have at least 80% homology thereto and exhibit improved tranglycosylation activity on both fucosylated and non-fucosylated GlcNAc acceptors against broad range of N-glycans of high mannose, hybrid and complex types, wherein the said mutants enable efficient transfer of an activated oligosaccharide donors on fucosylated and non-fucosylated GlcNAc acceptors to form new homogenous glycoform of glycopeptide or glycoprotein or therapeutic antibodies.

In another aspect, the present invention provides EndoS2 mutants that show remarkable transglycosylation activity but diminished hydrolytic activity, wherein the mutants preferably includes site specific mutations including mutations at T138, D182, D226, T227, and T228, but are not limited to T138D (SEQ ID NO.6), T138E (SEQ ID NO.7), T138F (SEQ ID NO.8), T138H (SEQ ID NO.9), T138K (SEQ ID NO.10), T138L (SEQ ID NO.11), T138M (SEQ ID NO.12), T138N (SEQ ID NO.13), T138Q (SEQ ID NO.14), T138R (SEQ ID NO.15), T138V (SEQ ID NO.16), T138W (SEQ ID NO.17), D182Q (SEQ ID NO. 2), D226Q (SEQ ID NO. 3), T227Q (SEQ ID NO. 4), and T228Q (SEQ ID NO. 5).

In a further aspects, the present invention provides for remarkable transglycosylation activity of EndoS2 mutants but diminished hydrolytic activity to transfer activated oligosaccharide donors to fucosylated or non-fucosylated GlcNAc acceptors, wherein the activated oligosaccharides donors comprising synthetic glycan oxazolines. In one embodiment, the synthetic glycan oxazoline comprising diverse N-glycans of high mannose, hybrid and complex types having the formula:

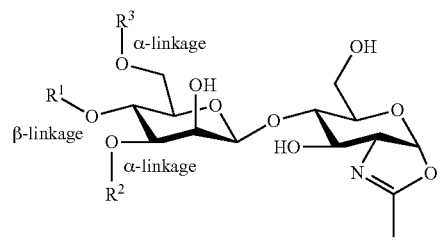

Wherein, $R^1$ is —H or N-acetyl glucosamine attached via β-1, 4 linkage and $R^2$ and $R^3$ are same or different and are independently selected from the glycosyl groups shown in FIG. 13.

In another aspect, the present invention provides EndoS2 mutants for transglycosylation at core fucosylated or non-fucosylated GlcNAc-acceptor, wherein the core fucosylated or non-fucosylated GlcNAc-acceptor comprising core fucosylated or non-fucosylated GlcNAc-peptides, proteins and IgG Fc domain or fragment thereof.

In a further aspects, the present invention provides EndoS2 mutants for transglycosylation at core fucosylated or non-fucosylated GlcNAc-IgG, wherein the IgG is a monoclonal antibody and is selected from the group consisting of cetuximab, rituximab, muromonab-CD3, abciximab, daclizumab, basiliximab, palivizumab, infliximab, trastuzumab, gemtuzumab ozogamicin, alemtuzumab, ibritumomab tiuxetan, adalimumab, omalizumab, tositumomab, I-131 tositumomab, efalizumab, bevacizumab, panitumumab, pertuzumab, natalizumab, etanercept, IGN101, voloiximab, Anti-CD80 mAb, Anti-CD23 mAb, CAT-3888, CDP-791, eraptuzumab, MDX-010, MDX-060, MDX-070, matuzumab, CP-675,206, CAL, SGN-30, zanolimumab, adecatumumab, oregovomab, nimotuzumab, ABT-874, denosumab, AM 108, AMG 714, fontolizumab, daclizumab, golimumab, CNTO 1275, ocrelizumab, HuMax-CD20, belimumab, epratuzumab, MLN1202, visilizumab, tocilizumab, ocrerlizumab, certolizumab pegol, eculizumab, pexelizumab, abciximab, and ranibizimumab.

In a separate aspect, the present invention provides a remodeling method of core fucosylated or non-fucosylated GlcNAc-peptide, protein, and IgG or IgG-Fc fragment, wherein the method comprising: providing peptide/protein/antibody-GlcNAc acceptor or Fc fragment and reacting with an activated oligosaccharide donors under the catalysis of *Streptococcus Pyogenes* EndoS2 mutants, and thereby preparing substantially pure glycoform of pre-existing peptides, proteins and monoclonal antibodies having heterogeneous glycosylation states.

In further aspect, the present invention provides method of using EndoS2 mutants for glycan remodeling of therapeutic IgG or Fc fragment thereof, wherein the method comprising:
A. Treating natural or recombinant core fucosylated or non-fucosylated therapeutic IgG or IgG-Fc fragment carrying heterogeneous N-glycans with Endoglycosidase (wild type EndoS2) together with or without bacterial alpha fucosidases to hydrolyze bond between two reducing end GlcNAc residues to form core fucosylated or non-fucosylated GlcNAc-IgG acceptor;
B. Transferring the wide range of predefined oligosaccharide building units in the form of activated oligosaccharide donors to core fucosylated or non-fucosylated GlcNAc-IgG to reconstitute natural beta 1, 4 linkage through transglycosylation using *Streptococcus Pyogenes* EndoS2 mutants, thereby attaching the predefined oligosaccharide to remodel core fucosylated or non-fucosylated IgG or Fc fragment thereof.

In further aspect, the present invention provides a composition of fucosylated or non-fucosylated glyco-engineered antibodies or antigen binding fragments comprising of IgG molecules having the same N-glycan structure at each site of the Fc region, wherein the N-glycan is of high mannose, hybrid, and complex types and is selected from the group consisting of:

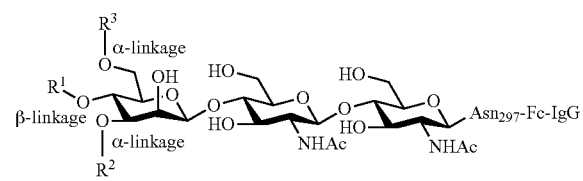

Wherein, $R^1$ is —H or N-acetyl glucosamine attached via β-1, 4 linkage and $R^2$ and $R^3$ are same or different and are independently selected from the glycosyl groups shown in FIG. 13.

In another aspect, the present invention provide the glycoengineered antibodies with improved effector functions such as bindings to FcγIIIA and ADCC, as compared to non-modified antibodies.

Another aspect of the present disclosure features a pharmaceutical composition comprising a composition of glycoengineered antibodies described herein and a pharmaceutically acceptable carrier for the treatment of cancer in a patient.

Examples of cancers include, but not limited to, B cell lymphomas, NHL, precursor B cell lymphoblastic leukemia/lymphoma and mature B cell neoplasms, B cell chronic lymphocytic leukemia (CLL)/small lymphocytic lymphoma (SLL), B cell prolymphocytic leukemia, lymphoplasmacytic lymphoma, mantle cell lymphoma (MCL), follicular lymphoma (FL), low-grade, intermediate-grade and high-grade (FL), cutaneous follicle center lymphoma, marginal zone B cell lymphoma, MALT type marginal zone B cell lymphoma, nodal marginal zone B cell lymphoma, splenic type marginal zone B cell lymphoma, hairy cell leukemia, diffuse large B cell lymphoma, Burkitt's lymphoma, plasmacytoma, plasma cell myeloma, post-transplant lymphoproliferative disorder, Waldenstrom's macroglobulinemia, and anaplastic large-cell lymphoma (ALCL).

The present invention envisioned glycoengineering of antibodies selected from the group consisting of cetuximab, rituximab, muromonab-CD3, abciximab, daclizumab, basiliximab, palivizumab, infliximab, trastuzumab, gemtuzumab ozogamicin, alemtuzumab, ibritumomab tiuxetan, adalimumab, omalizumab, tositumomab, I-131 tositumomab, efalizumab, bevacizumab, panitumumab, pertuzumab, natalizumab, etanercept, IGN101, volociximab, Anti-CD80 mAb, Anti-CD23 mAb, CAT-3888, CDP-791, eraptuzumab, MDX-010, MDX-060, MDX-070, matuzumab, CP-675, 206, CAL, SGN-30, zanolimumab, adecatumumab, oregovomab, nimotuzumab, ABT-874, denosumab, AM 108, AMG 714, fontolizumab, daclizumab, golimumab, CNTO 1275, ocrelizumab, HuMax-CD20, belimumab, epratuzumab, MLN1202, visilizumab, tocilizumab, ocrerlizumab, certolizumab pegol, eculizumab, pexelizumab, abciximab, and ranibizimumab.

Other aspects and advantages of the invention will be apparent from the following description and the appended claims.

BRIEF DESCRIPTION OF THE DRAWINGS

FIG. 1 shows sequence of wild type EndoS2 and potential amino acid residues selected for site directed mutagenesis (SEQ ID NO:1).

FIG. 2 shows amino acid sequence of EndoS2 mutants T138D (SEQ ID NO.6), T138E (SEQ ID NO.7), T138F (SEQ ID NO.8), T138H (SEQ ID NO.9), T138K (SEQ ID NO.10), T138L (SEQ ID NO.11), T138M (SEQ ID NO.12), T138N (SEQ ID NO.13), T138Q (SEQ ID NO.14), T138R (SEQ ID NO.15), T138V (SEQ ID NO.16), T138W (SEQ ID NO.17), D182Q (SEQ ID NO. 2), D226Q (SEQ ID NO. 3), T227Q (SEQ ID NO. 4), and T228Q (SEQ ID NO. 5) in accordance with one embodiment of the invention.

DETAILED DESCRIPTION OF THE INVENTION

Figure 3:
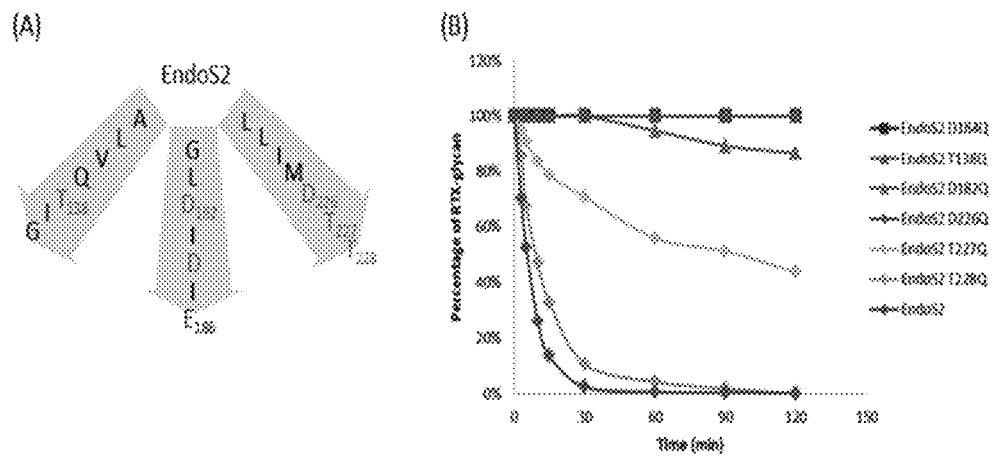
FIG. 3 shows (A) The carton represents the putative $3^{rd}$, $4^{th}$ and $5^{th}$ β-sheets of the catalytic domain of Endo S2 based on the alignment with EndoS. The catalytic residue E186, colored in red, served as a general acid/base while the mutated amino acids sites surrounding E186 are colored in blue. (B) The glycan hydrolytic activity of wild type EndoS2 and selected mutants at each site using commercial Rituximab as a substrate. The reactions of EndoS2 mutants (52 nM) with commercial Rituximab (52 incubated for 120 min and analyzed by SDS-PAGE. The relative percentage of original Rituximab (Rtx-glycan) is shown. Mutant D184Q was used for comparison.

Embodiments of the invention relate to selected mutants of EndoS2 that show remarkable transglycosylation activities to transfer a broad range of N-glycans of high mannose, hybrid or complex types, from activated oligosaccharide oxazolines to fucosylated or non-fucosylated GlcNAc-peptides, proteins or IgGs with little or negligible product hydrolysis. The novel EndoS2 mutants acted efficiently to provide homogeneously glycosylated glycopeptides, glycoproteins and therapeutic antibodies and Fc fragments thereof, having various defined glycoforms. Still further, embodiments of the present invention may provide glycoengineered antibodies with enhancement of their effector functions, such as FcγIIIA bindings and antibody dependent cell mediated cytotoxicity (ADCC) etc., as well as pharmacological properties. Embodiments of the present invention also allow for rapid investigation of effects of diverse Fc glycosylations of therapeutic antibodies on their effector functions.

In the following description, reference is made to the accompanying drawings that form a part hereof, and embodiments of the invention are shown by way of specific examples which may be practiced. These embodiments are described in detail to enable those skilled in the art to practice the invention, and it is to be understood that other embodiments may be devised and that structural, logical and electrical changes may be made without departing from the scope of the present invention. The following description of example embodiments is, therefore, not to be taken in a limited sense, and the scope of the present invention is defined by the appended claims.

Unless defined otherwise, all technical and scientific terms used herein have the same meanings as commonly understood by one of ordinary skills in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, cell lines, vectors, animals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

Before the present materials and methods are described, it is understood that this invention is not limited to the particular methodology, protocols, materials, and reagents described, as these may vary. It is also to be under stood that the terminology used herein is for the purpose of describing particular embodiments only, and is not intended to limit the scope of the present invention which will be limited only by the appended claims.

Definitions

It must be noted that as used herein and in the appended claims, the singular forms "a", "an", and "the" include plural reference unless the context clearly dictates otherwise.

As used herein, the term "glycan" refers to a polysaccharide, oligosaccharide or monosaccharide. Glycans can be monomers or polymers of sugar residues and can be linear or branched. A glycan may include natural sugar residues (e.g., glucose, N-acetylglucosamine, N-acetyl neuraminic acid, galactose, mannose, fucose, hexose, arabinose, ribose, xylose, etc.) and/or modified sugars (e.g., 2'-fluororibose, 2'-deoxyribose, phosphomannose, 6' sulfo N-acetylglucosamine, etc).

As used herein, the terms "fucose," "core fucose," and "core fucose residue" are used interchangeably and refer to a fucose in α-1,6-position linked to the N-acetylglucosamine.

As used herein, the terms "N-glycan", "N-linked glycan", "N-linked glycosylation", "Fc glycan" and "Fc glycosylation" are used interchangeably and refer to an N-linked oligosaccharide attached by an N-acetylglucosamine (GlcNAc) linked to the amide nitrogen of an asparagine residue in a Fc-containing polypeptide. The term "Fc-containing polypeptide" refers to a polypeptide, such as an antibody, which comprises an Fc region.

As used herein, the term "glycosylation pattern" and "glycosylation profile" are used interchangeably and refer to the characteristic "fingerprint" of the N-glycan species that have been released from a glycoprotein or antibody, either enzymatically or chemically, and then analyzed for their carbohydrate structure, for example, using LC-HPLC, or MALDI-TOF MS, and the like. See, for example, the review in Current Analytical Chemistry, Vol. 1, No. 1 (2005), pp. 28-57; herein incorporated by reference in its entirety.

As used herein, the term "glycoengineered Fc" when used herein refers to N-glycan on the Fc region has been altered or engineered either enzymatically or chemically. The term "Fc glycoengineering" as used herein refers to the enzymatic or chemical process used to make the glycoengineered Fc.

The terms "homogeneous", "uniform", "uniformly" and "homogeneity" in the context of a glycosylation profile of Fc region are used interchangeably and are intended to mean a single glycosylation pattern represented by one desired N-glycan species, with no trace amount of precursor N-glycan As used herein, the terms "IgG", "IgG molecule", "monoclonal antibody", "immunoglobulin", and "immunoglobulin molecule" are used interchangeably.

As used herein, the term "Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see review M. in Daëron, *Annu. Rev. Immunol.* 15:203-234 (1997)). FcRs are reviewed in Ravetch and Kinet, *Annu. Rev. Immunol* 9:457-92 (1991); Capel et al., Immunomethods 4:25-34 (1994); and de Haas et al., *J. Lab. Clin. Med.* 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)).

The term "effector function" as used herein refers to a biochemical event that results from the interaction of an antibody Fc region with an Fc receptor or ligand. Exemplary "effector functions" include Clq binding; complement dependent cytotoxicity; Fc receptor binding; antibody-dependent cell-mediated cytotoxicity (ADCC); phagocytosis; down regulation of cell surface receptors (e.g. B cell receptor; BCR), etc. Such effector functions can be assessed using various assays known in the art.

As used herein, the term "Antibody-dependent cell-mediated cytotoxicity" or "ADCC" refers to a form of cytotoxicity in which secreted Ig bound onto Fc receptors (FcRs) present on certain cytotoxic cells (e.g. Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *PNAS (USA)* 95:652-656 (1998).

Approximately two-thirds of therapeutic proteins, available in the market and/or currently in various stages of clinical trials are monoclonal antibodies, of which there are 30 antibodies and their derivatives have been approved for treatment of different conditions mainly neoplastic diseases, inflammatory and auto immunological diseases. However, the glycan microheterogeneity of natural and recombinant glycoproteins presents a major barrier in developing glycoprotein-based drugs. Controlling glycosylation states is extremely difficult during protein or antibody expression that are typically produced as a mixture of glycoforms that differ only in the structure of the pendent oligosaccharides, which may have different biological activities. Two enzymes that recently have attracted great attention for glycoengineering of therapeutic antibodies are EndoS and EndoS2 from the human pathogen *Streptococcus pyogenes* (Collin and Olsen 2001; Sjögren et al. 2013). The enzymes were first discovered as bacterial immune evasion factors that abolish the effector functions of immunoglobulin G (IgG) by hydrolyzing N-linked glycans on the antibody.

The complex N-linked oligosaccharide on each CH2 domain of IgGs is crucial for the structure of the Fc region and thus the interaction with the Fc receptors (Krapp et al. 2003; Woof and Burton 2004). The oligosaccharide chain at IgG-Fc domain contains several N-Acetyl-Glucosamine (GlcNAc) and mannose (Man) residues, and eventually galactose (Gal) and fucose (Fuc) residues as well as sialic acid (Sia or NANA for N-acetylneuraminic acid). A GlcNAc, with or without al-6 Fuc, is attached to the Asn297. A GlcNAcβ1-4 is attached to this first GlcNAc. A manβ1-4 is then found, to which two Manα1-6 and Manα1-3 arms are attached. Both arms contain an additional GlcNAcβ1-2 to which a Galβ1-4 can be attached or not. Thus, the carbohydrate chain can contain 0, 1 or 2 galactose residues, defining G0, G1, and G2 glycoforms, respectively. Further variations occur, including the presence of a bisecting GlcNAcβ1-4 and the capping of one or both of the terminal galactose residues with a sialic acid or even a Galα1-3 residue. The enzymatic cleavage of the Fc-glycan with Endoglycosidases causes the Fc region to deform, and thus, dramatically decrease in IgGs binding to Fcγ receptors (Allhorn et al. 2008). Despite of their 37% sequence identity, both EndoS and EndoS2 catalyze the hydrolysis of the β-1,4 linkage between the two N-acetylglucosamines (GlcNAcs) in the core of the N-linked glycan of human IgG. However, in addition to complex type glycans, EndoS2 hydrolyze hybrid and oligomannose structures to a greater extent compared with EndoS (Sjögren et al. 2015).

Since the first antibody therapy was introduced in the 1980s, there are more than 240 therapeutic antibodies in clinical trials and the field is steadily expanding (Chan and Carter 2010). The role of the IgG-Fc glycans on antibody functions has gained a huge attention in the growing field of monoclonal therapeutic antibodies. Therefore, to improve the efficacy of the therapeutic antibodies, the major focus is turning towards the engineering the Fc-glycan that specifically interact with selected Fcγ receptors. (Sondermann et al. 2013; Bournazos et al. 2014; Monnet et al. 2014; Quast and Lünemann 2014). Some of the important glycan modifications that dramatically affect the effector functions includes, i) the lack of a core fucose residue attached to the reducing end GlcNAc residue leads to increased affinity for FcγRIIIa and thus increased antibody-dependent cytotoxicity (Iida et al. 2006); ii) sialic acid rich glycans on IgG that have been claimed to increase the anti-inflammatory response of IgGs through increased interaction with DC-SIGN receptors on dendritic cells and macrophages (Anthony et al. 2008; Anthony and Ravetch 2010; Pincetic et al. 2014); iii) having bisecting GlcNAc induces a strong ADCC as compared to its parental counterpart. The recent improvements in biotechnology tools to control the Fc-glycosylation states of IgG facilitates development of therapeutic antibodies with pre-defined glycoforms. Accordingly, the EndoS2 mutants of present invention is a great advancement in the field for glyco-engineering of peptides, proteins, and antibodies of interest to attach broad range of N-glycans of high mannose, hybrid and complex types for functional and structural studies.

The features and advantages of the present invention are more fully shown by the following non-limiting examples. One skilled in the art would appreciate that these examples are for illustration only and that other modifications and variations are possible without departing from the scope of the invention.

Examples

Generation of EndoS2 Mutants for Glycoengineering of Peptides, Therapeutic Proteins and Intact IgGs or Fc Fragment Thereof Until now, examples of glycosynthases have been produced from some GH85 endoglycosidases (ENGases), including EndoA, EndoM, and EndoD, by site-directed mutagenesis of a key asparagine (Asn) residue responsible for promoting oxazolinium ion intermediate formation during hydrolysis.

EndoS from *Streptococcus pyogenes* belongs to the glycoside hydrolase family 18 (GH18), which also includes EndoF1, EndoF2, and EndoF3. These GH18 enzymes are known for their efficient hydrolytic activities that cleave asparagine-linked bi-antennary glycans on human IgGs to produce mono-GlcNAc antibodies. Even though EndoS can also function as glycosynthases to synthesize chitobiose linkages using glycan oxazolines as substrates, the intrinsic hydrolysis activities of these enzymes present a major hurdle, which leads to significantly reduced yields of synthetic glycoproteins. Further improvement in enzymatic activities leads to the development of endoglycosidase mutants, including EndoS D233Q. This gives important motifs on the active site of ENGase: D-X-E in GH18. This motif supports the catalysis mechanism on ENGase, which uses a double-displacement reaction with neighboring group participation. In this mechanism, the 2-acetamide group of the GlcNAc acts as a nucleophile to substitute the leaving group at the anomeric center, with the formation of an oxazolinium ion intermediate promoted by the carboxylate of Asp. The catalytic residue, glutamate, acts as a general acid/base that protonates the leaving aglycan group and deprotonates the nucleophilic $H_2O$ causing the hydrolysis of the oxazolinium ion intermediate to form the hydrolytic product. The carboxylate of aspartate, 2 residues on the N-terminal side of E, was proposed to promote and stabilize the formation of the oxazolinium ion intermediate. The mutation on this D of EndoS to Q was demonstrated to improve transglycosylation and diminish hydrolysis activity.

Although the mutants EndoS D233Q and D233A demonstrated a great potential for the synthesis of homogeneous antibody, the addition of large amount of enzymes is required to achieve efficient reaction. The preparation of enzymes and the following steps to remove enzymes after reaction became tedious and labor intensive. Recently, a new enzyme, EndoS2, was identified from another serotype of *Streptococcus pyogenes*. In addition to the endo-β-N-acetyl-glucosaminidase activity on complex type of N-glycan as in EndoS-catalyzed possess, EndoS2 can cleave hybrid and oligomannose structures to a greater extent than EndoS (Jonathan et al., 2013 and 2015).

EndoS2 shares only 37% sequence identity with EndoS, the structure of which adopts a common $((β/α)_8$ barrel conformation in the catalytic domain. Based on alignment of these two enzymes, residue E186 located on the fourth β-sheet of EndoS2 corresponds to the general acid/base D235 of EndoS.

In order to explore the catalytic efficiency of transglycosylation of EndoS2, we set out to test whether conversion of amino acids near catalytic site would modulate the trasglycosylation activity. A few residues in the proximity of catalytic domain were chosen and mutated by site-directed mutagenesis. The mutated residues include T138 on the third β-sheet, D182 on the fourth β-sheet, and D226, T227 and T228 on the fifth β-sheet (FIG. 3A). The EndoS2 mutants tested include T138D (SEQ ID NO.6), T138E (SEQ ID NO.7), T138F (SEQ ID NO.8), T138H (SEQ ID NO.9), T138K (SEQ ID NO.10), T138L (SEQ ID NO.11), T138M (SEQ ID NO.12), T138N (SEQ ID NO.13), T138Q (SEQ ID NO.14), T138R (SEQ ID NO.15), T138V (SEQ ID NO.16), T138W (SEQ ID NO.17), D182Q (SEQ ID NO. 2), D226Q (SEQ ID NO. 3), T227Q (SEQ ID NO. 4), and T228Q (SEQ ID NO. 5) (FIG. 2 and Table 1). These mutants expressed in *E. coli* in high yield as His-tag fusion proteins, which can be purified with a Ni-NTA affinity column. It has been observed that mutations near active sites dramatically improved the transglycosylation activity and decreased the endoglycosidase activity, resulting in remarkable glycosynthase efficiency. In addition, these mutants are capable of transferring complex type N-glycans from activated glycan oxazolines to deglycosylated intact antibodies with negligible product hydrolysis.

TABLE 1 below shows the sequences of various EndoS2 mutants.

SEQ ID NO. 1 (Wild-type)
1 MDKHLLVKRTLGCVCAATLMGAALATHHDSLNTVKAEEKTVQTGKT
DQQVGAKLVQEIREGKRGPLYAGYFRTWHDRASTGIDGKQQHPENTMA
EVPKEVDILFVFHDHTASDSPFWSELKDSYVHKLHQQGTALVQTIGVN
ELNGRTGLSKDYPDTPEGNKALAAAIVKAFVTDRGVDGLDIDIEHEFT
NKRTPEEDARALNVFKEIAQLIGKNGSDKSKLLIMDTTLSVENNPIFK
GIAEDLDYLLRQYYGSQGGEAEVDTINSDWNQYQNYIDASQFMIGFSF
FEESASKGNLWFDVNEYDPNNPEKGKDIEGTRAKKYAEWQPSTGGLKA
GIFSYAIDRDGVAHVPSTYKNRTSTNLQRHEVDNISHTDYTVSRKLKT
LMTEDKRYDVIDQKDIPDPALREQIIQQVGQYKGDLERYNKTLVLTGD
KIQNLKGLEKLSKLQKLELRQLSNVKEITPELLPESMKKDAELVMVGM
TGLEKLNLSGLNRQTLDGIDVNSITHLTSFDISHNSLDLSEKSEDRKL
LMTLMEQVSNHQKITVKNTAFENQKPKGYYPQTYDTKEGHYDVDNAEH
DILTDFVFGTVTKRNTFIGDEEAFAIYKEGAVDGRQYVSKDYTYEAFR
KDYKGYKVHLTASNLGETVTSKVTATTDETYLVDVSDGEKVVHHMKLN
IGSGAIMMENLAKGAKVIGTSGDFEQAKKIFDGEKSDRFFTWGQTNWI
AFDLGEINLAKEWRLFNAETNTEIKTDSSLNVAKGRLQILKDTTIDLE
KMDIKNRKEYLSNDENWTDVAQMDDAKAIFNSKLSNVLSRYWRFCVDG
GASSYYPQYTELQILGQRLSNDVANTLD
843

SEQ ID NO. 6 (T138D)
1 MDKHLLVKRTLGCVCAATLMGAALATHHDSLNTVKAEEKTVQTGKT
DQQVGAKLVQEIREGKRGPLYAGYFRTWHDRASTGIDGKQQHPENTMA
EVPKEVDILFVEHDHTASDSPFWSELKDSYVHKLHQQGTALVQDIGVN
ELNGRTGLSKDYPDTPEGNKALAAAIVKAFVTDRGVDGLDIDIEHEFT
NKRTPEEDARALNVEKEIAQLIGKNGSDKSKLLIMDTTLSVENNPIFK
GIAEDLDYLLRQYYGSQGGEAEVDTINSDWNQYQNYIDASQEMIGESF
FEESASKGNLWFDVNEYDPNNPEKGKDIEGTRAKKYAEWQPSTGGLKA
GIFSYAIDRDGVAHVPSTYKNRTSTNLQRHEVDNISHTDYTVSRKLKT
LMTEDKRYDVIDQKDIPDPALREQIIQQVGQYKGDLERYNKTLVLTGD
KIQNLKGLEKLSKLQKLELRQLSNVKEITPELLPESMKKDAELVMVGM
TGLEKLNLSGLNRQTLDGIDVNSITHLTSFDISHNSLDLSEKSEDRKL
LMTLMEQVSNHQKITVKNTAFENQKPKGYYPQTYDTKEGHYDVDNAEH
DILTDEVEGTVTKRNTFIGDEEAFAIYKEGAVDGRQYVSKDYTYEAFR
KDYKGYKVHLTASNLGETVTSKVTATTDETYLVDVSDGEKVVHHMKLN
IGSGAIMMENLAKGAKVIGTSGDFEQAKKIEDGEKSDRFFTWGQTNWI
AFDLGEINLAKEWRLFNAETNTEIKTDSSLNVAKGRLQILKDTTIDLE
KMDIKNRKEYLSNDENWTDVAQMDDAKAIFNSKLSNVLSRYWRFCVDG
GASSYYPQYTELQILGQRLSNDVANTLD
843

SEQ ID NO. 7 (T138E)
1 MDKHLLVKRTLGCVCAATLMGAALATHHDSLNTVKAEEKTVQTGKT
DQQVGAKLVQEIREGKRGPLYAGYFRTWHDRASTGIDGKQQHPENTMA
EVPKEVDILFVEHDHTASDSPEWSELKDSYVHKLHQQGTALVEIGVN
ELNGRTGLSKDYPDTPEGNKALAAAIVKAFVTDRGVDGLDIDIEHEFT
NKRTPEEDARALNVEKEIAQLIGKNGSDKSKLLIMDTTLSVENNPIFK
GIAEDLDYLLRQYYGSQGGEAEVDTINSDWNQYQNYIDASQEMIGESE
FEESASKGNLWFDVNEYDPNNPEKGKDIEGTRAKKYAEWQPSTGGLKA
GIFSYAIDRDGVAHVPSTYKNRTSTNLQRHEVDNISHTDYTVSRKLKT
LMTEDKRYDVIDQKDIPDPALREQIIQQVGQYKGDLERYNKTLVLTGD
KIQNLKGLEKLSKLQKLELRQLSNVKEITPELLPESMKKDAELVMVGM
TGLEKLNLSGLNRQTLDGIDVNSITHLTSFDISHNSLDLSEKSEDRKL
LMTLMEQVSNHQKITVKNTAFENQKPKGYYPQTYDTKEGHYDVDNAEH
DILTDEVEGTVTKRNTFIGDEEAFAIYKEGAVDGRQYVSKDYTYEAFR
KDYKGYKVHLTASNLGETVTSKVTATTDETYLVDVSDGEKVVHHMKLN
IGSGAIMMENLAKGAKVIGTSGDFEQAKKIEDGEKSDRFFTWGQTNWI
AFDLGEINLAKEWRLENAETNTEIKTDSSLNVAKGRLQILKDTTIDLE
KMDIKNRKEYLSNDENWTDVAQMDDAKAIFNSKLSNVLSRYWRFCVDG
GASSYYPQYTELQILGQRLSNDVANTLD
843

SEQ ID NO. 8 (T138F)
1 MDKHLLVKRTLGCVCAATLMGAALATHHDSLNTVKAEEKTVQTGKT
DQQVGAKLVQEIREGKRGPLYAGYFRTWHDRASTGIDGKQQHPENTMA
EVPKEVDILEVEHDHTASDSPFWSELKDSYVHKLHQQGTALVQFIGVN
ELNGRTGLSKDYPDTPEGNKALAAAIVKAFVTDRGVDGLDIDIEHEFT
NKRTPEEDARALNVEKEIAQLIGKNGSDKSKLLIMDTTLSVENNPIFK
GIAEDLDYLLRQYYGSQGGEAEVDTINSDWNQYQNYIDASQEMIGESE
FEESASKGNLWFDVNEYDPNNPEKGKDIEGTRAKKYAEWQPSTGGLKA
GIFSYAIDRDGVAHVPSTYKNRTSTNLQRHEVDNISHTDYTVSRKLKT
LMTEDKRYDVIDQKDIPDPALREQIIQQVGQYKGDLERYNKTLVLTGD
KIQNLKGLEKLSKLQKLELRQLSNVKEITPELLPESMKKDAELVMVGM
TGLEKLNLSGLNRQTLDGIDVNSITHLTSFDISHNSLDLSEKSEDRKL
LMTLMEQVSNHQKITVKNTAFENQKPKGYYPQTYDTKEGHYDVDNAEH
DILTDEVEGTVTKRNTFIGDEEAFAIYKEGAVDGRQYVSKDYTYEAFR
KDYKGYKVHLTASNLGETVTSKVTATTDETYLVDVSDGEKVVHHMKLN
IGSGAIMMENLAKGAKVIGTSGDFEQAKKIEDGEKSDREFTWGQTNWI
AFDLGEINLAKEWRLENAETNTEIKTDSSLNVAKGRLQILKDTTIDLE
KMDIKNRKEYLSNDENWTDVAQMDDAKAIENSKLSNVLSRYWRFCVDG
GASSYYPQYTELQILGQRLSNDVANTLD
843

SEQ ID NO. 9 (T138H)
1 MDKHLLVKRTLGCVCAATLMGAALATHHDSLNTVKAEEKTVQTGKT
DQQVGAKLVQEIREGKRGPLYAGYFRTWHDRASTGIDGKQQHPENTMA
EVPKEVDILFVEHDHTASDSPEWSELKDSYVHKLHQQGTALVQHIGVN
ELNGRTGLSKDYPDTPEGNKALAAAIVKAFVTDRGVDGLDIDIEHEFT
NKRTPEEDARALNVEKEIAQLIGKNGSDKSKLLIMDTTLSVENNPIFK
GIAEDLDYLLRQYYGSQGGEAEVDTINSDWNQYQNYIDASQEMIGESE
FEESASKGNLWFDVNEYDPNNPEKGKDIEGTRAKKYAEWQPSTGGLKA
GIFSYAIDRDGVAHVPSTYKNRTSTNLQRHEVDNISHTDYTVSRKLKT
LMTEDKRYDVIDQKDIPDPALREQIIQQVGQYKGDLERYNKTLVLTGD
KIQNLKGLEKLSKLQKLELRQLSNVKEITPELLPESMKKDAELVMVGM
TGLEKLNLSGLNRQTLDGIDVNSITHLTSFDISHNSLDLSEKSEDRKL
LMTLMEQVSNHQKITVKNTAFENQKPKGYYPQTYDTKEGHYDVDNAEH
DILTDEVEGTVTKRNTFIGDEEAFAIYKEGAVDGRQYVSKDYTYEAFR
KDYKGYKVHLTASNLGETVTSKVTATTDETYLVDVSDGEKVVHHMKLN
IGSGAIMMENLAKGAKVIGTSGDFEQAKKIEDGEKSDREFTWGQTNWI
AFDLGEINLAKEWRLENAETNTEIKTDSSLNVAKGRLQILKDTTIDLE
KMDIKNRKEYLSNDENWTDVAQMDDAKAIFNSKLSNVLSRYWRFCVDG
GASSYYPQYTELQILGQRLSNDVANTLD
843

SEQ ID NO. 10 (T138K)
1 MDKHLLVKRTLGCVCAATLMGAALATHHDSLNTVKAEEKTVQTGKT
DQQVGAKLVQEIREGKRGPLYAGYFRTWHDRASTGIDGKQQHPENTMA
EVPKEVDILFVEHDHTASDSPEWSELKDSYVHKLHQQGTALVQKIGVN
ELNGRTGLSKDYPDTPEGNKALAAAIVKAFVTDRGVDGLDIDIEHEFT
NKRTPEEDARALNVEKEIAQLIGKNGSDKSKLLIMDTTLSVENNPIFK
GIAEDLDYLLRQYYGSQGGEAEVDTINSDWNQYQNYIDASQEMIGESF
FEESASKGNLWFDVNEYDPNNPEKGKDIEGTRAKKYAEWQPSTGGLKA
GIFSYAIDRDGVAHVPSTYKNRTSTNLQRHEVDNISHTDYTVSRKLKT
LMTEDKRYDVIDQKDIPDPALREQIIQQVGQYKGDLERYNKTLVLTGD
KIQNLKGLEKLSKLQKLELRQLSNVKEITPELLPESMKKDAELVMVGM
TGLEKLNLSGLNRQTLDGIDVNSITHLTSFDISHNSLDLSEKSEDRKL
LMTLMEQVSNHQKITVKNTAFENQKPKGYYPQTYDTKEGHYDVDNAEH
DILTDFVFGTVTKRNTFIGDEEAFAIYKEGAVDGRQYVSKDYTYEAFR
KDYKGYKVHLTASNLGETVTSKVTATTDETYLVDVSDGEKVVHHMKLN
IGSGAIMMENLAKGAKVIGTSGDFEQAKKIEDGEKSDRFFTWGQTNWI
AFDLGEINLAKEWRLFNAETNTEIKTDSSLNVAKGRLQILKDTTIDLE
KMDIKNRKEYLSNDENWTDVAQMDDAKAIFNSKLSNVLSRYWRFCVDG
GASSYYPQYTELQILGQRLSNDVANTLD
843

SEQ ID NO. 11 (T138L)
1 MDKHLLVKRTLGCVCAATLMGAALATHHDSLNTVKAEEKTVQTGKT
DQQVGAKLVQEIREGKRGPLYAGYFRTWHDRASTGIDGKQQHPENTMA
EVPKEVDILFVEHDHTASDSPFWSELKDSYVHKLHQQGTALVQLIGVN
ELNGRTGLSKDYPDTPEGNKALAAAIVKAFVTDRGVDGLDIDIEHEFT
NKRTPEEDARALNVEKEIAQLIGKNGSDKSKLLIMDTTLSVENNPIFK
GIAEDLDYLLRQYYGSQGGEAEVDTINSDWNQYQNYIDASQEMIGESF
FEESASKGNLWFDVNEYDPNNPEKGKDIEGTRAKKYAEWQPSTGGLKA
GIFSYAIDRDGVAHVPSTYKNRTSTNLQRHEVDNISHTDYTVSRKLKT
LMTEDKRYDVIDQKDIPDPALREQIIQQVGQYKGDLERYNKTLVLTGD
KIQNLKGLEKLSKLQKLELRQLSNVKEITPELLPESMKKDAELVMVGM
TGLEKLNLSGLNRQTLDGIDVNSITHLTSFDISHNSLDLSEKSEDRKL
LMTLMEQVSNHQKITVKNTAFENQKPKGYYPQTYDTKEGHYDVDNAEH
DILTDEVEGTVTKRNTFIGDEEAFAIYKEGAVDGRQYVSKDYTYEAFR
KDYKGYKVHLTASNLGETVTSKVTATTDETYLVDVSDGEKVVHHMKLN
IGSGAIMMENLAKGAKVIGTSGDFEQAKKIEDGEKSDRFFTWGQTNWI
AFDLGEINLAKEWRLENAETNTEIKTDSSLNVAKGRLQILKDTTIDLE
KMDIKNRKEYLSNDENWTDVAQMDDAKAIENSKLSNVLSRYWRFCVDG
GASSYYPQYTELQILGQRLSNDVANTLD
843

SEQ ID NO. 12 (T138M)
1 MDKHLLVKRTLGCVCAATLMGAALATHHDSLNTVKAEEKTVQTGKT
DQQVGAKLVQEIREGKRGPLYAGYFRTWHDRASTGIDGKQQHPENTMA
EVPKEVDILFVEHDHTASDSPFWSELKDSYVHKLHQQGTALVQMIGVN
ELNGRTGLSKDYPDTPEGNKALAAAIVKAFVTDRGVDGLDIDIEHEFT
NKRTPEEDARALNVEKEIAQLIGKNGSDKSKLLIMDTTLSVENNPIFK
GIAEDLDYLLRQYYGSQGGEAEVDTINSDWNQYQNYIDASQEMIGESF

TABLE 1-continued below shows the sequences of various EndoS2 mutants.

FEESASKGNLWFDVNEYDPNNPEKGKDIEGTRAKKYAEWQPSTGGLKA
GIFSYAIDRDGVAHVPSTYKNRTSTNLQRHEVDNISHTDYTVSRKLKT
LMTEDKRYDVIDQKDIPDPALREQIIQQVGQYKGDLERYNKTLVLTGD
KIQNLKGLEKLSKLQKLELRQLSNVKEITPELLPESMKKDAELVMVGM
TGLEKLNLSGLNRQTLDGIDVNSITHLTSFDISHNSLDLSEKSEDRKL
LMTLMEQVSNHQKITVKNTAFENQKPKGYYPQTYDTKEGHYDVDNAEH
DILTDEVEGTVTKRNTFIGDEEAFAIYKEGAVDGRQYVSKDYTYEAFR
KDYKGYKVHLTASNLGETVTSKVTATTDETYLVDVSDGEKVVHHMKLN
IGSGAIMMENLAKGAKVIGTSGDFEQAKKIEDGEKSDREFTWGQTNWI
AFDLGEINLAKEWRLENAETNTEIKTDSSLNVAKGRLQILKDTTIDLE
KMDIKNRKEYLSNDENWTDVAQMDDAKAIFNSKLSNVLSRYWRFCVDG
GASSYYPQYTELQILGQRLSNDVANTLD
843

SEQ ID NO. 13 (T138N)
1 MDKHLLVKRTLGCVCAATLMGAALATHHDSLNTVKAEEKTVQTGKT
DQQVGAKLVQEIREGKRGPLYAGYFRTWHDRASTGIDGKQQHPENTMA
EVPKEVDILEVEHDHTASDSPEWSELKDSYVHKLHQQGTALVQNIGVN
ELNGRTGLSKDYPDTPEGNKALAAAIVKAFVTDRGVDGLDIDIEHEFT
NKRTPEEDARALNVEKEIAQLIGKNGSDKSKLLIMDTTLSVENNPIFK
GIAEDLDYLLRQYYGSQGGEAEVDTINSDWNQYQNYIDASQEMIGESE
FEESASKGNLWFDVNEYDPNNPEKGKDIEGTRAKKYAEWQPSTGGLKA
GIFSYAIDRDGVAHVPSTYKNRTSTNLQRHEVDNISHTDYTVSRKLKT
LMTEDKRYDVIDQKDIPDPALREQIIQQVGQYKGDLERYNKTLVLTGD
KIQNLKGLEKLSKLQKLELRQLSNVKEITPELLPESMKKDAELVMVGM
TGLEKLNLSGLNRQTLDGIDVNSITHLTSFDISHNSLDLSEKSEDRKL
LMTLMEQVSNHQKITVKNTAFENQKPKGYYPQTYDTKEGHYDVDNAEH
DILTDEVEGTVTKRNTFIGDEEAFAIYKEGAVDGRQYVSKDYTYEAFR
KDYKGYKVHLTASNLGETVTSKVTATTDETYLVDVSDGEKVVHHMKLN
IGSGAIMMENLAKGAKVIGTSGDFEQAKKIEDGEKSDRFFTWGQTNWI
AFDLGEINLAKEWRLFNAETNTEIKTDSSLNVAKGRLQILKDTTIDLE
KMDIKNRKEYLSNDENWTDVAQMDDAKAIENSKLSNVLSRYWRFCVDG
GASSYYPQYTELQILGQRLSNDVANTLD
843

SEQ ID NO. 14 (T138Q)
1 MDKHLLVKRTLGCVCAATLMGAALATHHDSLNTVKAEEKTVQTGKT
DQQVGAKLVQEIREGKRGPLYAGYFRTWHDRASTGIDGKQQHPENTMA
EVPKEVDILFVEHDHTASDSPEWSELKDSYVHKLHQQGTALVQQIGVN
ELNGRTGLSKDYPDTPEGNKALAAAIVKAFVTDRGVDGLDIDIEHEFT
NKRTPEEDARALNVEKEIAQLIGKNGSDKSKLLIMDTTLSVENNPIFK
GIAEDLDYLLRQYYGSQGGEAEVDTINSDWNQYQNYIDASQEMIGESF
FEESASKGNLWFDVNEYDPNNPEKGKDIEGTRAKKYAEWQPSTGGLKA
GIFSYAIDRDGVAHVPSTYKNRTSTNLQRHEVDNISHTDYTVSRKLKT
LMTEDKRYDVIDQKDIPDPALREQIIQQVGQYKGDLERYNKTLVLTGD
KIQNLKGLEKLSKLQKLELRQLSNVKEITPELLPESMKKDAELVMVGM
TGLEKLNLSGLNRQTLDGIDVNSITHLTSFDISHNSLDLSEKSEDRKL
LMTLMEQVSNHQKITVKNTAFENQKPKGYYPQTYDTKEGHYDVDNAEH
DILTDEVEGTVTKRNTFIGDEEAFAIYKEGAVDGRQYVSKDYTYEAFR
KDYKGYKVHLTASNLGETVTSKVTATTDETYLVDVSDGEKVVHHMKLN
IGSGAIMMENLAKGAKVIGTSGDFEQAKKIEDGEKSDRFFTWGQTNWI
AFDLGEINLAKEWRLFNAETNTEIKTDSSLNVAKGRLQILKDTTIDLE
KMDIKNRKEYLSNDENWTDVAQMDDAKAIFNSKLSNVLSRYWRFCVDG
GASSYYPQYTELQILGQRLSNDVANTLD
843

SEQ ID NO. 15 (T138R)
1 MDKHLLVKRTLGCVCAATLMGAALATHHDSLNTVKAEEKTVQTGKT
DQQVGAKLVQEIREGKRGPLYAGYFRTWHDRASTGIDGKQQHPENTMA
EVPKEVDILFVEHDHTASDSPEWSELKDSYVHKLHQQGTALVQRIGVN
ELNGRTGLSKDYPDTPEGNKALAAAIVKAFVTDRGVDGLDIDIEHEFT
NKRTPEEDARALNVEKEIAQLIGKNGSDKSKLLIMDTTLSVENNPIFK
GIAEDLDYLLRQYYGSQGGEAEVDTINSDWNQYQNYIDASQEMIGESF
FEESASKGNLWFDVNEYDPNNPEKGKDIEGTRAKKYAEWQPSTGGLKA
GIFSYAIDRDGVAHVPSTYKNRTSTNLQRHEVDNISHTDYTVSRKLKT
LMTEDKRYDVIDQKDIPDPALREQIIQQVGQYKGDLERYNKTLVLTGD
KIQNLKGLEKLSKLQKLELRQLSNVKEITPELLPESMKKDAELVMVGM
TGLEKLNLSGLNRQTLDGIDVNSITHLTSFDISHNSLDLSEKSEDRKL
LMTLMEQVSNHQKITVKNTAFENQKPKGYYPQTYDTKEGHYDVDNAEH
DILTDFVFGTVTKRNTFIGDEEAFAIYKEGAVDGRQYVSKDYTYEAFR
KDYKGYKVHLTASNLGETVTSKVTATTDETYLVDVSDGEKVVHHMKLN
IGSGAIMMENLAKGAKVIGTSGDFEQAKKIEDGEKSDRFFTWGQTNWI
AFDLGEINLAKEWRLFNAETNTEIKTDSSLNVAKGRLQILKDTTIDLE
KMDIKNRKEYLSNDENWTDVAQMDDAKAIFNSKLSNVLSRYWRFCVDG
GASSYYPQYTELQILGQRLSNDVANTLD
843

TABLE 1-continued below shows the sequences of various EndoS2 mutants.

SEQ ID NO. 16 (T138V)
1 MDKHLLVKRTLGCVCAATLMGAALATHHDSLNTVKAEEKTVQTGKT
DQQVGAKLVQEIREGKRGPLYAGYFRTWHDRASTGIDGKQQHPENTMA
EVPKEVDILFVEHDHTASDSPEWSELKDSYVHKLHQQGTALVQVIGVN
ELNGRTGLSKDYPDTPEGNKALAAAIVKAFVTDRGVDGLDIDIEHEFT
NKRTPEEDARALNVEKEIAQLIGKNGSDKSKLLIMDTTLSVENNPIFK
GIAEDLDYLLRQYYGSQGGEAEVDTINSDWNQYQNYIDASQEMIGESF
FEESASKGNLWFDVNEYDPNNPEKGKDIEGTRAKKYAEWQPSTGGLKA
GIFSYAIDRDGVAHVPSTYKNRTSTNLQRHEVDNISHTDYTVSRKLKT
LMTEDKRYDVIDQKDIPDPALREQIIQQVGQYKGDLERYNKTLVLTGD
KIQNLKGLEKLSKLQKLELRQLSNVKEITPELLPESMKKDAELVMVGM
TGLEKLNLSGLNRQTLDGIDVNSITHLTSFDISHNSLDLSEKSEDRKL
LMTLMEQVSNHQKITVKNTAFENQKPKGYYPQTYDTKEGHYDVDNAEH
DILTDEVEGTVTKRNTFIGDEEAFAIYKEGAVDGRQYVSKDYTYEAFR
KDYKGYKVHLTASNLGETVTSKVTATTDETYLVDVSDGEKVVHHMKLN
IGSGAIMMENLAKGAKVIGTSGDFEQAKKIEDGEKSDREFTWGQTNWI
AFDLGEINLAKEWRLENAETNTEIKTDSSLNVAKGRLQILKDTTIDLE
KMDIKNRKEYLSNDENWTDVAQMDDAKAIENSKLSNVLSRYWRFCVDG
GASSYYPQYTELQILGQRLSNDVANTLD
843

SEQ ID NO. 17 (T138W)
1 MDKHLLVKRTLGCVCAATLMGAALATHHDSLNTVKAEEKTVQTGKT
DQQVGAKLVQEIREGKRGPLYAGYFRTWHDRASTGIDGKQQHPENTMA
EVPKEVDILFVEHDHTASDSPEWSELKDSYVHKLHQQGTALVQWIGVN
ELNGRTGLSKDYPDTPEGNKALAAAIVKAFVTDRGVDGLDIDIEHEFT
NKRTPEEDARALNVEKEIAQLIGKNGSDKSKLLIMDTTLSVENNPIFK
GIAEDLDYLLRQYYGSQGGEAEVDTINSDWNQYQNYIDASQEMIGESF
FEESASKGNLWFDVNEYDPNNPEKGKDIEGTRAKKYAEWQPSTGGLKA
GIFSYAIDRDGVAHVPSTYKNRTSTNLQRHEVDNISHTDYTVSRKLKT
LMTEDKRYDVIDQKDIPDPALREQIIQQVGQYKGDLERYNKTLVLTGD
KIQNLKGLEKLSKLQKLELRQLSNVKEITPELLPESMKKDAELVMVGM
TGLEKLNLSGLNRQTLDGIDVNSITHLTSFDISHNSLDLSEKSEDRKL
LMTLMEQVSNHQKITVKNTAFENQKPKGYYPQTYDTKEGHYDVDNAEH
DILTDEVEGTVTKRNTFIGDEEAFAIYKEGAVDGRQYVSKDYTYEAFR
KDYKGYKVHLTASNLGETVTSKVTATTDETYLVDVSDGEKVVHHMKLN
IGSGAIMMENLAKGAKVIGTSGDFEQAKKIEDGEKSDREFTWGQTNWI
AFDLGEINLAKEWRLENAETNTEIKTDSSLNVAKGRLQILKDTTIDLE
KMDIKNRKEYLSNDENWTDVAQMDDAKAIENSKLSNVLSRYWRFCVDG
GASSYYPQYTELQILGQRLSNDVANTLD
843

SEQ ID. 2 (D182Q)
1 MDKHLLVKRTLGCVCAATLMGAALATHHDSLNTVKAEEKTVQTGKT
DQQVGAKLVQEIREGKRGPLYAGYFRTWHDRASTGIDGKQQHPENTMA
EVPKEVDILFVEHDHTASDSPEWSELKDSYVHKLHQQGTALVQTIGVN
ELNGRTGLSKDYPDTPEGNKALAAAIVKAFVTDRGVDGLQIDIEHEFT
NKRTPEEDARALNVEKEIAQLIGKNGSDKSKLLIMDTTLSVENNPIFK
GIAEDLDYLLRQYYGSQGGEAEVDTINSDWNQYQNYIDASQEMIGESF
FEESASKGNLWFDVNEYDPNNPEKGKDIEGTRAKKYAEWQPSTGGLKA
GIFSYAIDRDGVAHVPSTYKNRTSTNLQRHEVDNISHTDYTVSRKLKT
LMTEDKRYDVIDQKDIPDPALREQIIQQVGQYKGDLERYNKTLVLTGD
KIQNLKGLEKLSKLQKLELRQLSNVKEITPELLPESMKKDAELVMVGM
TGLEKLNLSGLNRQTLDGIDVNSITHLTSFDISHNSLDLSEKSEDRKL
LMTLMEQVSNHQKITVKNTAFENQKPKGYYPQTYDTKEGHYDVDNAEH
DILTDEVEGTVTKRNTFIGDEEAFAIYKEGAVDGRQYVSKDYTYEAFR
KDYKGYKVHLTASNLGETVTSKVTATTDETYLVDVSDGEKVVHHMKLN
IGSGAIMMENLAKGAKVIGTSGDFEQAKKIFDGEKSDRFFTWGQTNWI
AFDLGEINLAKEWRLFNAETNTEIKTDSSLNVAKGRLQILKDTTIDLE
KMDIKNRKEYLSNDENWTDVAQMDDAKAIFNSKLSNVLSRYWRFCVDG
GASSYYPQYTELQILGQRLSNDVANTLD
843

SEQ ID. 3 (D226Q)
1 MDKHLLVKRTLGCVCAATLMGAALATHHDSLNTVKAEEKTVQTGKT
DQQVGAKLVQEIREGKRGPLYAGYFRTWHDRASTGIDGKQQHPENTMA
EVPKEVDILFVEHDHTASDSPEWSELKDSYVHKLHQQGTALVQTIGVN
ELNGRTGLSKDYPDTPEGNKALAAAIVKAFVTDRGVDGLDIDIEHEFT
NKRTPEEDARALNVEKEIAQLIGKNGSDKSKLLIMQTTLSVENNPIFK
GIAEDLDYLLRQYYGSQGGEAEVDTINSDWNQYQNYIDASQFMIGFSF
FEESASKGNLWFDVNEYDPNNPEKGKDIEGTRAKKYAEWQPSTGGLKA
GIFSYAIDRDGVAHVPSTYKNRTSTNLQRHEVDNISHTDYTVSRKLKT
LMTEDKRYDVIDQKDIPDPALREQIIQQVGQYKGDLERYNKTLVLTGD
KIQNLKGLEKLSKLQKLELRQLSNVKEITPELLPESMKKDAELVMVGM
TGLEKLNLSGLNRQTLDGIDVNSITHLTSFDISHNSLDLSEKSEDRKL
LMTLMEQVSNHQKITVKNTAFENQKPKGYYPQTYDTKEGHYDVDNAEH
DILTDFVFGTVTKRNTFIGDEEAFAIYKEGAVDGRQYVSKDYTYEAFR

TABLE 1-continued below shows the sequences of various EndoS2 mutants.

```
KDYKGYKVHLTASNLGETVTSKVTATTDETYLVDVSDGEKVVHHMKLN
IGSGAIMMENLAKGAKVIGTSGDFEQAKKIFDGEKSDRFFTWGQTNWI
AFDLGEINLAKEWRLFNAETNTEIKTDSSLNVAKGRLQILKDTTIDLE
KMDIKNRKEYLSNDENWTDVAQMDDAKAIFNSKLSNVLSRYWRFCVDG
GASSYYPQYTELQILGQRLSNDVANTLD
843

SEQ ID. 4 (T227Q)
1 MDKHLLVKRTLGCVCAATLMGAALATHHDSLNTVKAEEKTVQTGKT
DQQVGAKLVQEIREGKRGPLYAGYFRTWHDRASTGIDGKQQHPENTMA
EVPKEVDILFVEHDHTASDSPEWSELKDSYVHKLHQQGTALVQTIGVN
ELNGRTGLSKDYPDTPEGNKALAAAIVKAFVTDRGVGLDIDIEHEFT
NKRTPEEDARALNVEKEIAQLIGKNGSDKSKLLIMDQTLSVENNPIFK
GIAEDLDYLLRQYYGSQGGEAEVDTINSDWNQYQNYIDASQFMIGESF
FEESASKGNLWFDVNEYDPNNPEKGKDIEGTRAKKYAEWQPSTGGLKA
GIFSYAIDRDGVAHVPSTYKNRTSTNLQRHEVDNISHTDYTVSRKLKT
LMTEDKRYDVIDQKDIPDPALREQIIQQVGQYKGDLERYNKTLVLTGD
KIQNLKGLEKLSKLQKLELRQLSNVKEITPELLPESMKKDAELVMVGM
TGLEKLNLSGLNRQTLDGIDVNSITHLTSFDISHNSLDLSEKSEDRKL
LMTLMEQVSNHQKITVKNTAFENQKPKGYYPQTYDTKEGHYDVDNAEH
DILTDEVEGTVTKRNTFIGDEEAFAIYKEGAVDGRQYVSKDYTYEAFR
KDYKGYKVHLTASNLGETVTSKVTATTDETYLVDVSDGEKVVHHMKLN
IGSGAIMMENLAKGAKVIGTSGDFEQAKKIEDGEKSDRFFTWGQTNWI
AFDLGEINLAKEWRLFNAETNTEIKTDSSLNVAKGRLQILKDTTIDLE
KMDIKNRKEYLSNDENWTDVAQMDDAKAIFNSKLSNVLSRYWRFCVDG
GASSYYPQYTELQILGQRLSNDVANTLD
843

SEQ ID. 5 (T228Q)
1 MDKHLLVKRTLGCVCAATLMGAALATHHDSLNTVKAEEKTVQTGKT
DQQVGAKLVQEIREGKRGPLYAGYFRTWHDRASTGIDGKQQHPENTMA
EVPKEVDILFVEHDHTASDSPFWSELKDSYVHKLHQQGTALVQTIGVN
ELNGRTGLSKDYPDTPEGNKALAAAIVKAFVTDRGVGLDIDIEHEFT
NKRTPEEDARALNVFKEIAQLIGKNGSDKSKLLIMDTQLSVENNPIFK
GIAEDLDYLLRQYYGSQGGEAEVDTINSDWNQYQNYIDASQFMIGESF
FEESASKGNLWFDVNEYDPNNPEKGKDIEGTRAKKYAEWQPSTGGLKA
GIFSYAIDRDGVAHVPSTYKNRTSTNLQRHEVDNISHTDYTVSRKLKT
LMTEDKRYDVIDQKDIPDPALREQIIQQVGQYKGDLERYNKTLVLTGD
KIQNLKGLEKLSKLQKLELRQLSNVKEITPELLPESMKKDAELVMVGM
TGLEKLNLSGLNRQTLDGIDVNSITHLTSFDISHNSLDLSEKSEDRKL
LMTLMEQVSNHQKITVKNTAFENQKPKGYYPQTYDTKEGHYDVDNAEH
DILTDEVEGTVTKRNTFIGDEEAFAIYKEGAVDGRQYVSKDYTYEAFR
KDYKGYKVHLTASNLGETVTSKVTATTDETYLVDVSDGEKVVHHMKLN
IGSGAIMMENLAKGAKVIGTSGDFEQAKKIEDGEKSDREFTWGQTNWI
AFDLGEINLAKEWRLENAETNTEIKTDSSLNVAKGRLQILKDTTIDLE
KMDIKNRKEYLSNDENWTDVAQMDDAKAIENSKLSNVLSRYWRFCVDG
GASSYYPQYTELQILGQRLSNDVANTLD
843
```

In accordance with embodiments of the invention, a novel EndoS2 mutant comprises a sequence selected from the sequences of SEQ ID NOs. 2-17. These mutants show improved tranglycosylation activities and reduced hydrolyzing activities. Therefore, they can catalyze efficient transfer of activated oligosaccharide donors to core GlcNAc-acceptors, which may be fucosylated or non-fucosylated.

In accordance with some preferred embodiments, an EndoS2 mutant may have a sequence identity of at least 80% (e.g., 80%, 85%, 90%, 95%, or 98%) to a sequence in SEQ ID Nos. 2-17 and have the desired transglycosylation activity, or fragment thereof having the transglycosylation activity.

In other preferred embodiments, the EndoS2 mutants of this invention, wherein the mutation sites are located in a region selected from the group consisting of residues 133-143, residues 177-187, and residues 221-233.

In yet other preferred embodiments, the EndoS2 mutants of this invention include T138D (SEQ ID NO.6), T138E (SEQ ID NO.7), T138F (SEQ ID NO.8), T138H (SEQ ID NO.9), T138K (SEQ ID NO.10), T138L (SEQ ID NO.11), T138M (SEQ ID NO.12), T138N (SEQ ID NO.13), T138Q (SEQ ID NO.14), T138R (SEQ ID NO.15), T138V (SEQ ID NO.16), T138W (SEQ ID NO.17), D182Q (SEQ ID NO. 2), D226Q (SEQ ID NO. 3), T227Q (SEQ ID NO. 4), and T228Q (SEQ ID NO. 5).

The Glycan Hydrolytic Activity of EndoS2 and its Mutants

The glycan hydrolytic activities of EndoS2 mutants were measured by using commercial Rituximab as a substrate. Rituximab, a therapeutic anti-CD20 monoclonal antibody, was used as a model mAb to examine the hydrolytic activity and potential transglycosylation activity of the EndoS2 mutants. The major Fc glycans of commercial Rituximab are core-fucosylated biantennary complex type oligosaccharides carrying 0-2 galactose moieties named G0F, G1F, and G2F glycoforms. Rituximab was treated with the wild type EndoS2 and EndoS2 mutants in a molar ratio of 1:1000 (enzyme: Rituximab). The glycan hydrolysis process was monitored by sodium dodecylsulfate polyacrylamide gel electrophoresis (SDS-PAGE).

The treatment with wild type EndoS2 resulted in a rapid deglycosylation to produce the corresponding GlcNAc-Fc N-glycans at the glycosylation sites (N297). These results confirm the remarkable Fc glycan-hydrolyzing activity of the wild-type EndoS2 on intact IgG, implicating its usefulness in the first step (hydrolysis) for glycosylation remodeling of mAbs. However, treatment with EndoS2 mutants showed reduced hydrolytic activities, as compared to the wild-type (WT) EndoS2. In particular, mutants at T138 and D226 exhibited extremely low or almost no N-glycan hydrolysis abilities during a 2 hour incubation period, and mutation at D182Q showed reduced the reaction rate by more than 60 folds, as compared to the WT EndoS2. These results indicate that residues D182, T138 and D226 are critical for the glycoside hydrolase activity (FIG. 3).

Figure 4:
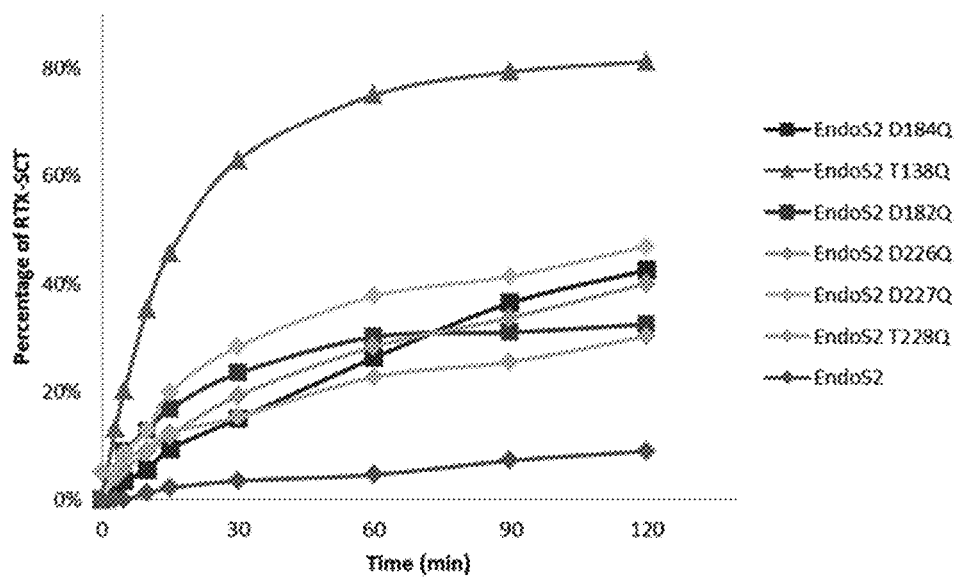
FIG. 4 shows the trans glycosylation activity of wild type EndoS2 and selected mutants (67.5 nM) at each sites using GlcNAc-Rituximab (67.5 μM) as an acceptor and α-2,6 sialylated bi-antennary complex type glycan (SCT)-oxazoline (2.5 mM) as a donor. The reaction was incubated for 2 hours and analyzed by SDS-PAGE. The relative percentages of Rituximab with α-2,6 sialylated bi-antennary complex type glycan at Fc region (Rtx-SCT) is shown. Mutant D184Q was used for comparison.

Transglycosylation Potentials of EndoS2 and its Mutants Using 2,6 Sialylated Bi-Antennary Complex Type (SCT) Oxazolines as the Donor Substrates Transglycosylation abilities of EndoS2 and its mutants were then examined using the GlcNAc-Rituximab as an acceptor and alpha-2,6-sialylated bi-antennary complex type (SCT) oxazolines as a donor substrate, as depicted in FIG. 4. The glycosylation remodeling process was monitored by sodium dodecyl sulfate polyacrylamide gel electrophoresis (SDS-PAGE). Incubation of the GlcNAc-Rituximab and the SCT-oxazoline (donor/acceptor, 1:1, weight ratio) with the wild type EndoS2 and its mutants (enzyme/antibody, 1:1000, molar ratio) showed the transient formation of the corresponding transglycosylation products for the wild type EndoS2 as monitored by SDS-PAGE, probably due to quick in situ hydrolysis of the products by the wild-type enzyme. Despite the loss of hydrolysis ability, all selected mutants (T138Q, D182Q, D226Q, T227Q and T228Q) had significant transglycosylation activity. These results indicate that the EndoS2 mutants are new efficient glycosynthases that enable the glycosylation of deglycosylated intact IgG with complex type N-glycan without product hydrolysis.

Figure 5:
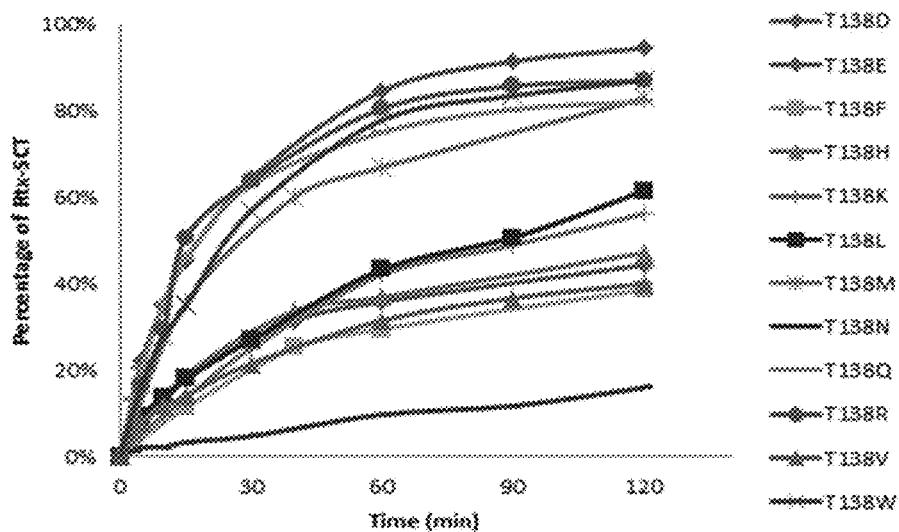
FIG. 5 shows the transglycosylation activity comparison of mutants at T138 using GlcNAc-Rituximab as an acceptor and α-2, 6 sialylated bi-antennary complex type glycan (SCT)-oxazoline as a donor. The reactions containing T138 mutants (67.5 nM), GlcNAc-Rituximab (67.5 µM), and SCT-oxazoline (2.5 mM) were incubated for 2 hours and analyzed by SDS-PAGE. The relative percentages of Rituximab with α-2, 6 sialylated bi-antennary complex type glycan at Fc region (Rtx-SCT) is shown.
Figure 6:
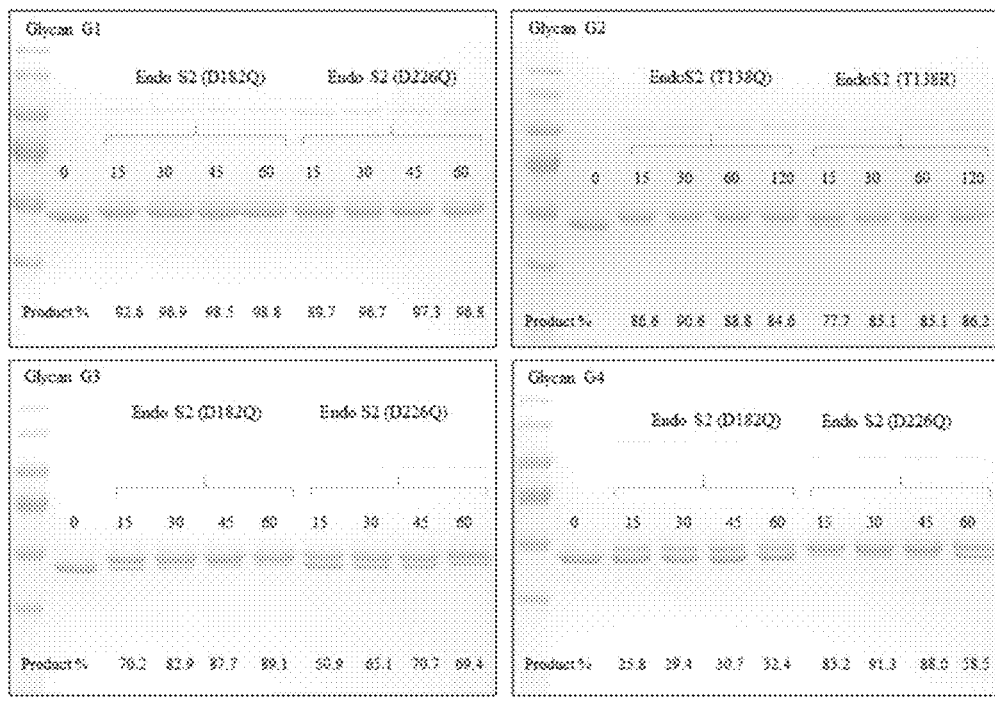
FIG. 6 shows the transglycosylation activity of selected mutants of EndoS2 against high mannose type Man$_5$GlcNAc$_2$ (glycan G1), Man$_9$GlcNAc$_2$ (glycan G2) and hybrid series glycans (G3 and G4), using GlcNAc-Rituximab as an acceptor and glycan-oxazolines (G1-G4) as donor substrates. The reaction progress was monitored by sodium dodecyl sulfate polyacrylamide gel electrophoresis (SD S-PAGE). Lane 1: marker; Lane 2: GlcNAc-Rituximab; time points are in Min.; product % is shown at the bottom.

Effects of Various Amino Acid Residues at T138 on their Transglycosylation Activities To identify the optimum amino acid residue at the site T138 that show potent transglycosylation activity only but devoid of hydrolytic activity, various mutations at this site were performed. The transglycosylation abilities of these mutants were then examined using the GlcNAc-Rituximab as an acceptor and alpha-2,6-sialylated bi-antennary complex type (SCT) oxazolines as a donor substrate (FIG. 5). Various mutants at T138 (67.5 nM) were incubated with 67.5 μM GlcNAc-Rituximab and 2.5 mM SCT-oxazoline for 2 hr. Products were analyzed by SDS-PAGE, and the relative percentages of GlcNAc-Rituximab (IgG) and Rituximab-SCT (IgG-glycan) are shown in FIG. 5. Among the mutants tested, T138E, T138R, T138W, T138M, and T138Q provided maximum tranglycosylation potency.

Transglycosylation Efficiencies of EndoS2 Mutants Using a Broad Range of N-Glycans of High Mannose, Hybrid and Complex Types Human IgGs molecules contain N-glycan on each of their Fc CH2 domains. These glycans include high-mannose, hybrid, and complex types. It has been demonstrated that the compositions Fc N-glycans are important determinants of the pro- and anti-inflammatory activities of antibodies. For example, the lack of the core fucose, as well as the attachment of a bisecting GlcNAc moiety, dramatically enhances the affinity of antibody for the FcγIIIa receptor (FcγRIIIa), which is responsible for the antibody-dependent cellular cytotoxicity (ADCC). The recombinant IgG molecules containing high-mannose glycans have been shown to clear faster in human blood, and exhibit decreased thermal stability. In addition, IgG molecules containing high-mannose and hybrid glycans showed more conformational flexibility in the CH2 domain. The most routine way to produce IgGs with distinct high mannose, hybrid and complex type Fc-glycans is to use various expression systems, including mammalian, plant, and yeast host cells. However, such expression systems often provide a mixture of glycoforms rather than a single glycan structure. Therefore, obtaining the pure glycoforms of therapeutic antibodies for biophysical and structural studies is of great interest in the glycan engineering field. Accordingly, glycosynthases, which enable efficient transfer of distinct high mannose, hybrid and complex type glycan to GlcNAc acceptors of peptide, proteins, and IgGs, are needed.

Next, the transglycosylation abilities of EndoS2 mutants of this invention were accessed using series of high mannose hybrid and complex types glycan oxazolines (Table 2). Results suggest that, in addition to the sialylated complex type N-glycan oxazolines, the EndoS2 mutants were equally efficient at transferring high mannose series Man$_5$GlcNAc-oxazoline (G1), Man$_9$GlcNAc-oxazoline (G2), hybrid series glycan G3 and G4, and bi- and tri-antennary complex series glycans G5-G16 for antibody glycoengineering, leading to the formation of the corresponding homogeneous glycoforms. Rituximab was used as a model antibody for this study. However, one skilled in the art would appreciate that other glycoproteins can also be modified in a similar manner. These results suggest that, in addition to the sialylated complex type N-glycan oxazolines, the EndoS2 mutants were equally efficient at transferring high mannose, hybrid, and triantennary complex type glycans.

Table 2 Lists the Structures of Diverse Glycan Oxazolines Used to Assess Transglycosylation Activity of Selected Mutants of EndoS2

TABLE 2

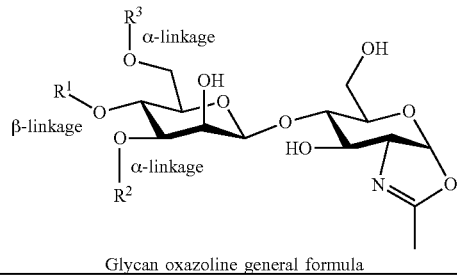

Glycan oxazoline general formula

| Glycan Type | Glycan number |
|---|---|
| High mannose type | G1 |
|  | G2 |
| Hybrid Type | G3 |
|  | G4 |
| Tri-antennary Complex Type | G5 |
|  | G6 |
| Bi-antennary Complex Type | G7 |
|  | G8 |
|  | G9 |
|  | G10 |
|  | G11 |
|  | G12 |
|  | G13 |
|  | G14 |
|  | G15 |
|  | G16 |

Figure 14:
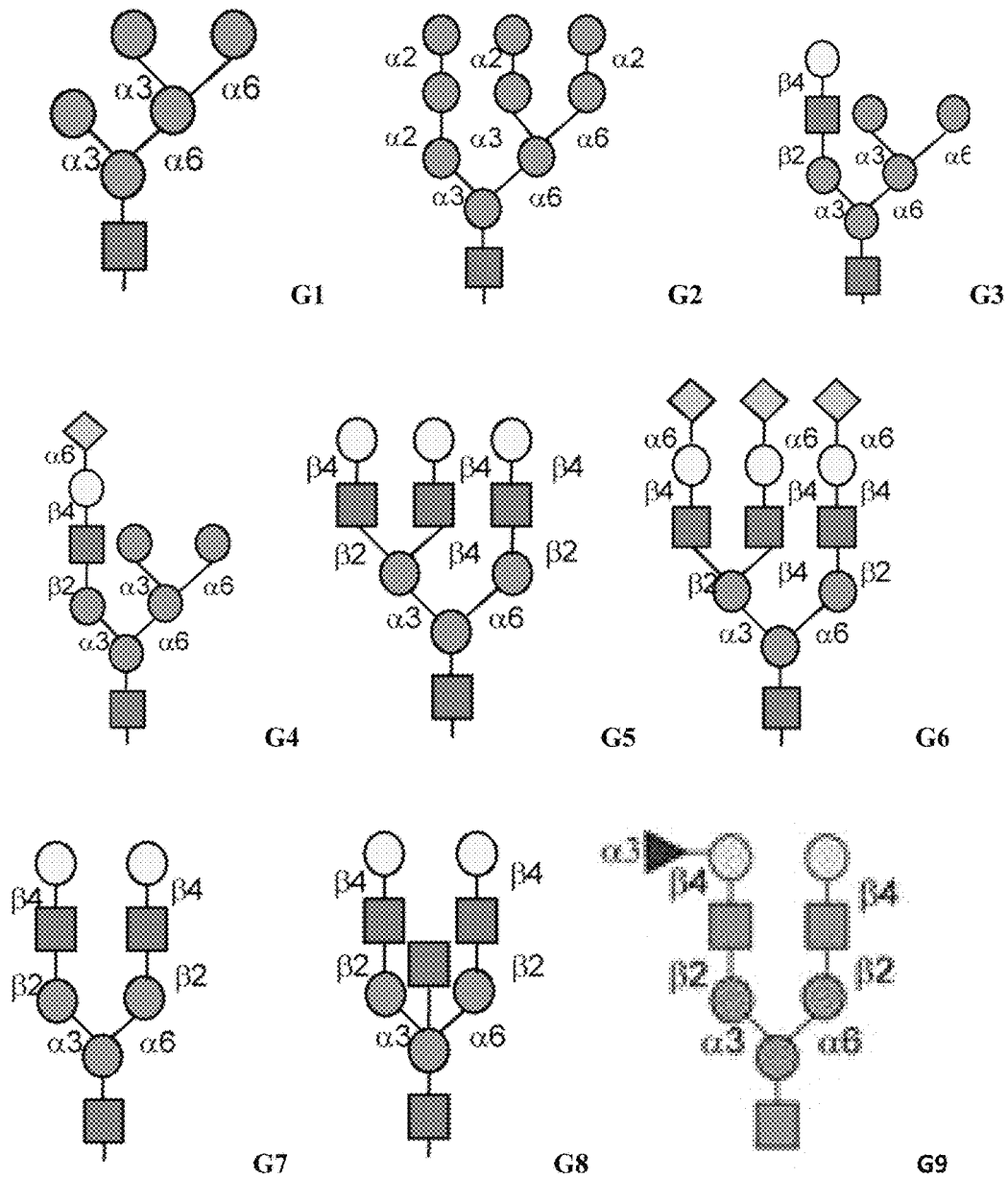
FIG. 14 shows structures of various glycosyl groups in glycan oxazolines in accordance with embodiments of the invention.
Figure 14:
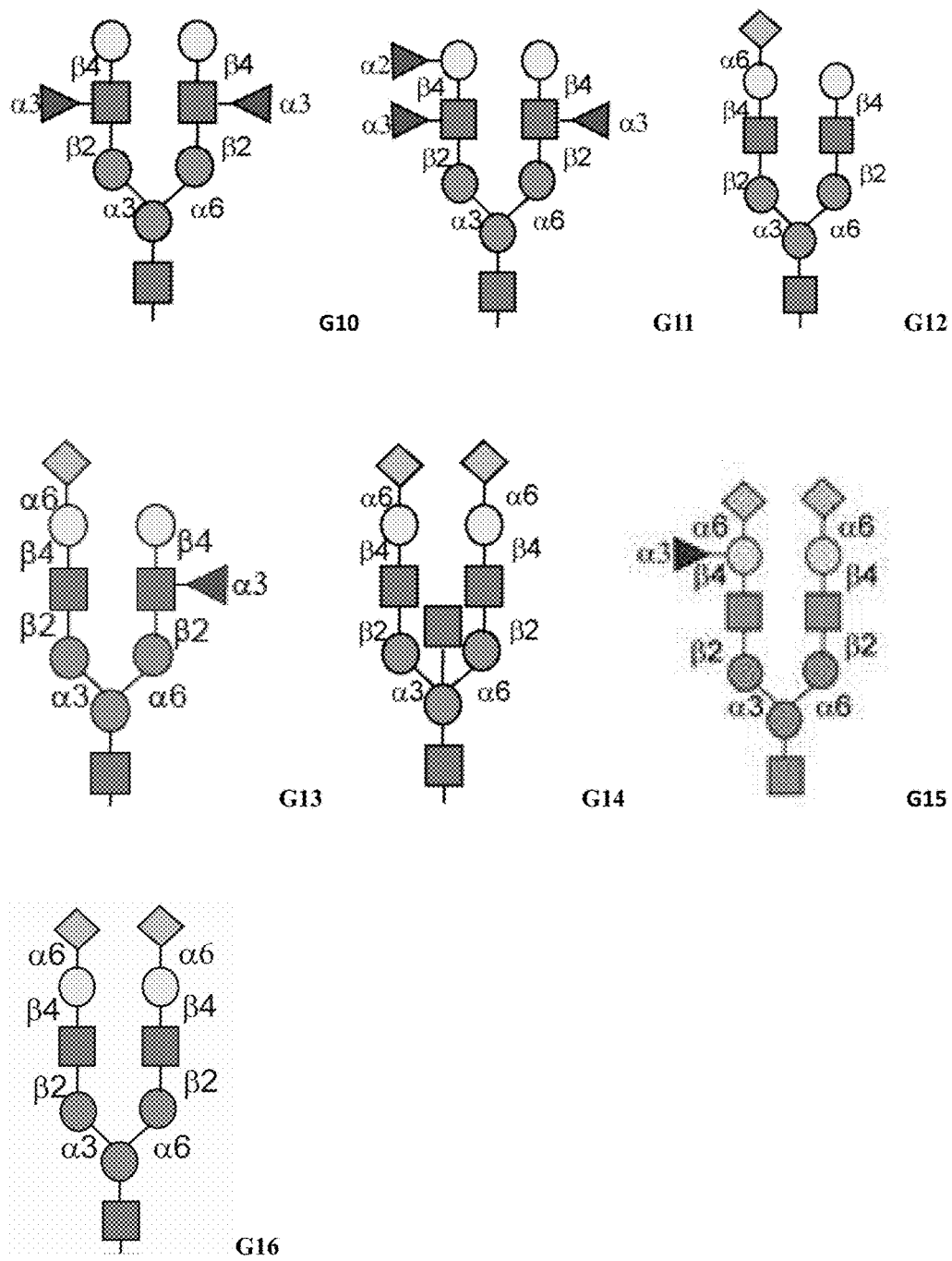

Note: the structures of G1-G16 are shown in FIG. 14.

Figure 7:
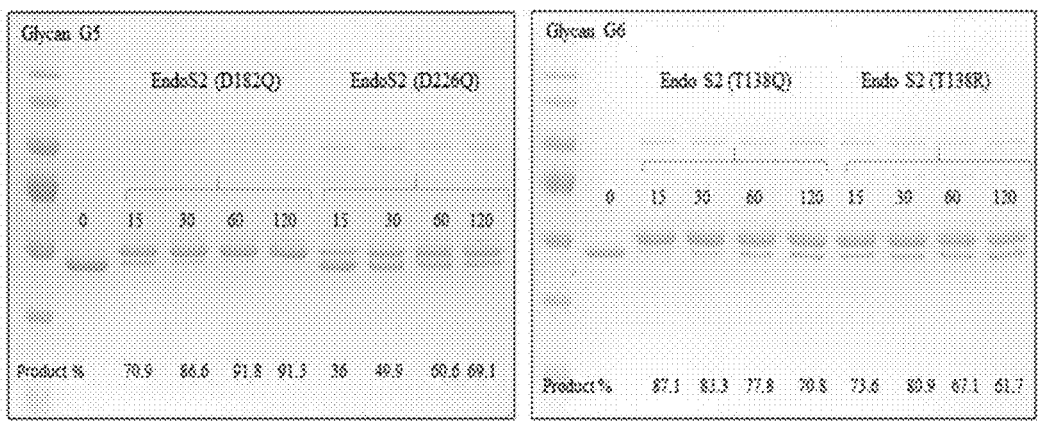
FIG. 7 shows the transglycosylation activity of selected mutants of EndoS2 against tri-antennary complex type glycans G5-with terminal galactose residues and G6-with terminal α-2, 6 sialic acids. The reaction was performed using GlcNAc-Rituximab as an acceptor and glycan-oxazolines (G4-G5) as donor substrate. The reaction progress was monitored by sodium dodecyl sulfate polyacrylamide gel electrophoresis (SDS-PAGE). Lane 1: marker; Lane 2: GlcNAc-Rituximab; time points are in Min.; product % is shown at the bottom.
Figure 8:
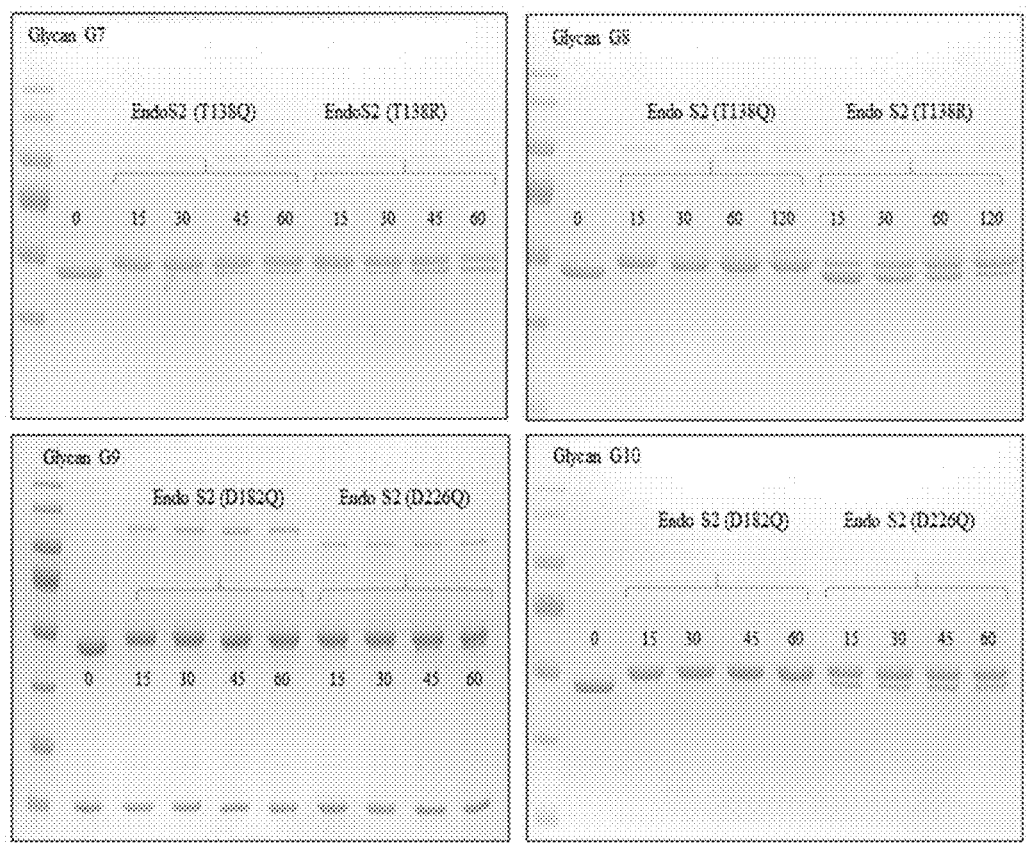
FIG. 8 shows the transglycosylation activity of selected mutants of EndoS2 against series of bi-antennary complex type structures. Glycan G7 is bi-antennary with terminal di-galactose, glycan G8 is bi-antennary with bisected GlcNAc and terminal di-galactose, glycan G9 is bi-antennary with alpha 1, 2 fucose on one of the two terminal galactose, and glycan G10 is bi-antennary with alpha 1, 3 fucose on both GlcNAc and terminal di-galactose. The transglycosylation was performed using GlcNAc-Rituximab as an acceptor and glycan-oxazolines (G7-G10) as donor substrate. The reaction progress was monitored by sodium dodecyl sulfate polyacrylamide gel electrophoresis (SDS-PAGE). Lane 1: marker; Lane 2: GlcNAc-Rituximab; time points are in Min.
Figure 9:
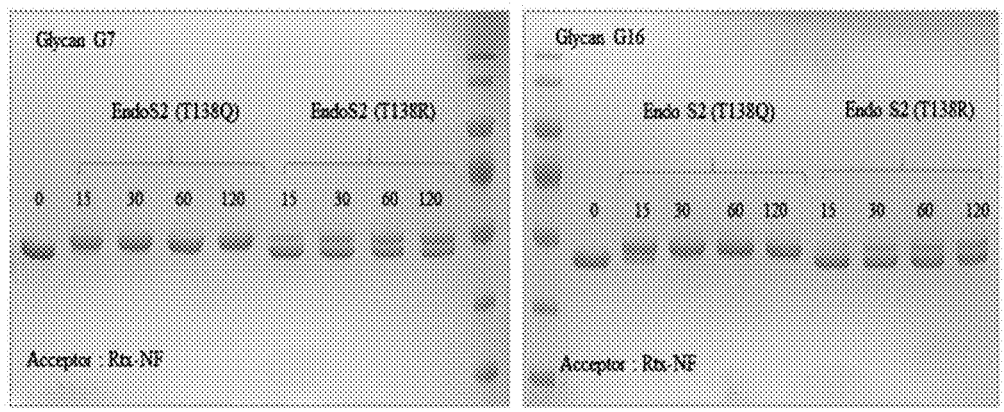
FIG. 9 shows transglycosylation activity of selected mutants of EndoS2 against bi-antennary complex type glycans G7-with terminal galactose residues and G16-with terminal α-2, 6 sialic acids. The reaction was performed using Fuc(α-1, 6)-GlcNAc-Rituximab as an acceptor and glycan-oxazolines (G4 and G16) as donor substrate. The reaction progress was monitored by sodium dodecyl sulfate polyacrylamide gel electrophoresis (SD S-PAGE). Lane 1: marker; Lane 2: GlcNAc-Rituximab; time points are in Min.; product % is shown at the bottom.
Figure 10:
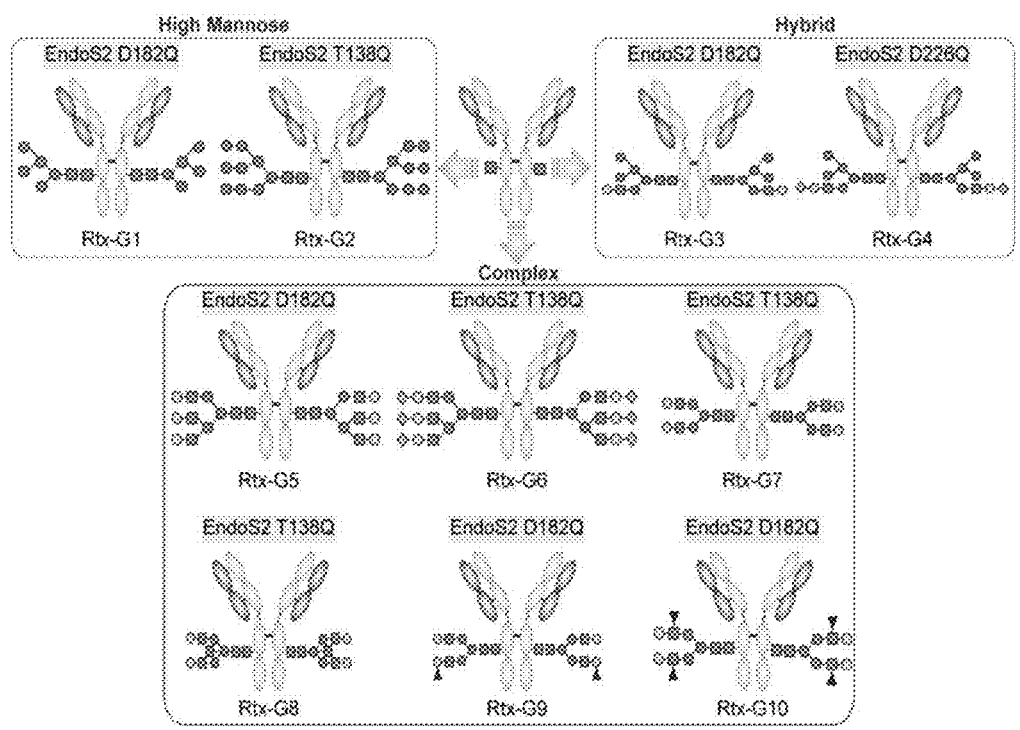
FIG. 10 shows the substrate specificity of selected mutants of EndoS2 against broad range of high mannose, hybrid, and complex type glycans.
Figure 11:
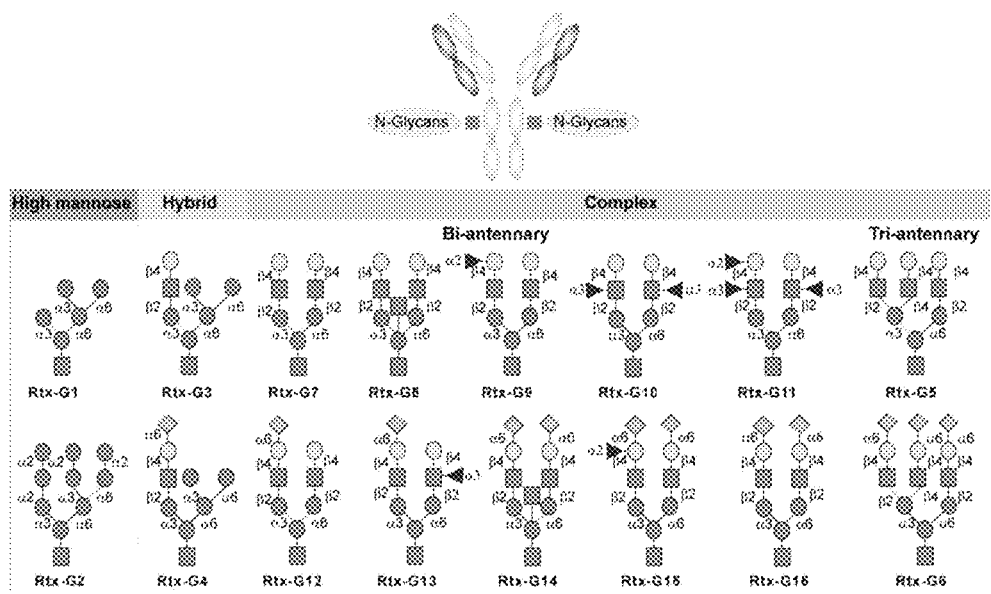
FIG. 11 shows the structures of Rituximab with diverse glycoforms at Fc region. The glycoforms includes series of high mannose, hybrid, and bi- and tri-antennary complex type structures.
Figure 12:
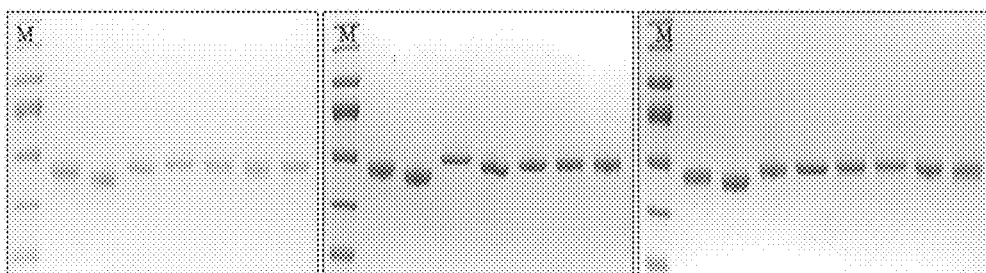
FIG. 12 shows SDS PAGE analysis of glycoengineered Rituximabs (Rtx G1-G16), GlcNAc-Rituximab, and commercial Rituximab.

The complex type glycans are divided into bi-, tri-, and tetra-antennary types based on the number of antennae present on the Man-GlcNAc-GlcNAc core. It is quite unusual that a glyocosynthase that accepts bi-antennary glycan-oxazoline can also accept tri- or tetra-antennary glycan-oxazolines because of the bulky nature of these glycans. In order to prove the effectiveness of these novel EndoS2 mutants, a series of complex type glycan oxazolines (Table 2) were used for transglycosylations, wherein Rituximab was used as a model antibody. The results are shown in FIGS. 7-8. These results indicate the remarkable transglycosylation efficiencies of the EndoS2 glycosynthase mutants to transfer diverse high mannose, hybrid and complex type glycans to an IgG-Fc region. Therefore, the EndoS2 glycosynthase mutants of the invention can be used for efficient and complete transglycosylation of different therapeutic antibodies for enhancement of their effector functions, because these novel mutants are devoid of (or with minimal) product hydrolytic activities.

The present invention discloses selected mutants of EndoS2 that show excellent transglycosylation activities with a broad range of N-glycans, including high mannose, hybrid and complex types.

In preferred embodiments, N-glycans of high mannose, hybrid and complex types are in an active oxazoline form, as shown by the general formula in Table 2.

In some embodiments, the high mannose type N-glycans described herein are selected from group consisting of Man$_3$GlcNAc, Man$_5$GlcNAc, Man$_6$GlcNAc, Man$_7$GlcNAc, Man$_8$GlcNAc, and Man$_9$GlcNAc. In preferred embodiments, the high mannose type N-glycan is Man$_5$GlcNAc.

In some embodiments, the hybrid type N-glycans described herein comprise at least one α-2,6- or α-2,3 terminal sialic acid on the alpha-1,3 arm, wherein the alpha-1,6 arm contains the trimannose residues.

In some embodiments, the hybrid type N-glycans described herein comprise at least one terminal galactose on the alpha-1,3 arm, wherein the alpha-1,6 arm contains the trimannose residues.

In some embodiments, the hybrid type N-glycans described herein comprise at least one terminal GlcNAc on the alpha-1,3 arm, wherein the alpha-1,6 arm contains the trimannose residues.

In some embodiments, the complex type glycans are of bi-, tri- and tetra-antennary complex types.

In some embodiments, the bi-antennary complex type N-glycans described herein comprise at least one α-2,6 or α-2,3 terminal sialic acid. In preferred embodiments, the N-glycans comprise two α-2,6 and/or α-2,3 terminal sialic acids.

In some embodiments, the bi-antennary complex type N-glycans described herein comprise at least one terminal galactose or GlcNAc. In preferred embodiments, the N-glycans comprise two terminal galactose and/or GlcNAc.

In some embodiments, the bi-antennary complex type N-glycans described herein comprise at least one alpha-1,2-fucose. In preferred embodiments, the N-glycans comprise two alpha-1,2-fucoses.

In some embodiments, the bi-antennary complex type N-glycans described herein comprise at least one alpha-1,3-fucose. In preferred embodiments, the N-glycans comprise two alpha-1,3-fucose.

In some embodiments, the bi-antennary complex type N-glycans described herein comprise bisecting GlcNAc.

In some embodiments, the bi-antennary complex type N-glycans described herein comprise at least one LacNAc repeat unit. In preferred embodiments, the N-glycans comprise two LacNAc repeat units.

In some embodiments, the tri-antennary complex type N-glycans described herein comprise at least one α-2,6 or α-2,3 terminal sialic acid. In preferred embodiments, the N-glycans comprise three α-2-6 and/or α-2,3 terminal sialic acids.

In some embodiments, the tri-antennary complex type N-glycans described herein comprise at least one terminal galactose or GlcNAc. In preferred embodiments, the N-glycans comprise three terminal galactose and/or GlcNAc.

In some embodiments, the complex type glycans are of bi-, and triantennary complex types comprising asymmetric antennae on either the alpha-1,3 or alpha-1,6 arm.

In some embodiments, the hybrid and bi-, and triantennary complex type N-glycans described herein comprise α-2,6 or α-2,3 terminal sialic acid. In a preferred embodiments, the hybrid and bi-, and triantennary complex type N-glycan comprises α-2,6 terminal sialic acid.

Glycoengineering of Rituximab to Provide Diverse Non-Fucosylated Glycoform for Improvement of Effector Functions Rituximab is a monoclonal antibody targeting the CD20 protein which is primarily found on the surface of 95% of B cell lymphomas. Rituximab destroys B cells and is therefore used to treat diseases which are characterized by excessive numbers of B cells, overactive B cells, or dysfunctional B cells. Rituximab is produced in Chinese hamster ovary (CHO) cells often delivers heterogeneous mixtures of glycosylation patterns, which may not show similar biological properties. Diversity in Fc glycosylation within an antibody may lead to diversity in Fc effector functions. Thus, this heterogeneity in Fc glycans has a functional consequence as it influences binding of IgG molecules to Fc receptors and Clq and thereby impacts antibody effector functions, and may trigger undesired effects in patients, which would be a safety concern.

Therefore, there is a need for improving monoclonal antibody therapy with improved anti-CD20 antibodies. A few specific glycoforms in the heterogeneous mixtures of glycosylation patterns are known to confer desired biological functions. Furthermore, in case of complex type glycoforms, apart from few modifications such core fucose and bisecting GlcNAc, several native modifications such as alpha-1,2 fucose on outer GlcNAc, alpha-1,3 fucose on Galactose, poly LacNAc motifs, and tri- and tetraantennary, have never been explored for their effects on biological activities. Thus, it is of great interest to generate therapeutic antibodies containing a well-defined glycan structure and sequence as desired glycoforms for therapeutic purposes.

Described herein are the functionally active anti-CD20 glycoengineered antibodies with optimized glycoforms that exhibit more potent biological activities, as compared to the therapeutic monoclonal antibodies.

The present disclosure features a novel class of anti-CD20 antibodies that can be generated from anti-CD20 monoclonal antibodies by Fc glycoengineering. The individual anti-CD20 glycoenginnered antibodies comprise homogeneous population and contain the same Fc glycan with a well-defined glycan structure and sequence. The glycoengineered anti-CD20 antibodies according to the present invention specifically bind to the same epitope of a human CD20 antigen on a cell membrane as its parental antibody. In addition, the homogeneous population of the same antibody all have the same effector binding site.

The term "parental antibody" as used herein refers to the anti-CD20 monoclonal antibody used to produce an anti-CD20 glycoengineered antibody. The parental antibodies can be obtained by cell culturing such as mammalian cell culture, *Pichia pastoris* or insect cell lines. Preferably, the parental antibodies are produced in mammalian cell culture. Exemplary parental antibodies include, but not limited to, Rituximab, Ofatumumab, Tositumomab, Ocrelizumab, 11B8 or 7D8 (disclosed in WO2004/035607).

In some embodiments, the exemplary anti-CD20 glycoengineered antibodies described herein comprise a heavy chain having the amino acid sequence set forth in SEQ ID NO.: 18, and a light chain having the amino acid sequence set forth in SEQ ID NO: 19. In preferred embodiments, the anti-CD20 glycoengineered antibodies each comprise a light chain sequence and a heavy chain sequence of Rituximab.

Table 3 below shows the heavy chain and the light chain sequences of Rituximab.

TABLE 3

Rituximab
Accession Number: DB00073
Source: http://www.drugbank.ca/drugs/DB00073
Rituximab heavy chain SEQ ID NO: 18:
QVQLQQPGAELVKPGASVKMSCKASGYTFTSYNMHWVKQTPGRGLEWI
GAIYPGNGDTSYNQKFKGKATLTADKSSSTAYMQLSSLTSEDSAVYYC
ARSTYYGGDWYFNVWGAGTTVTVSAASTKGPSVFPLAPSSKSTSGGTA
ALGCLVKDYFPEPVTVSWNSGALTSGVHTFPAVLQSSGLYSLSSVVTV
PSSSLGTQTYICNVNHKPSNTKVDKKVEPKSCDKTHTCPPCPAPELLG
GPSVFLFPPKPKDTLMISRTPEVTCVVVDVSHEDPEVKFNWYVDGVEV

TABLE 3-continued

Rituximab
Accession Number: DB00073
Source: http://www.drugbank.ca/drugs/DB00073
Rituximab heavy chain HNAKTKPREEQYNSTYRVVSVLTVLHQDWLNGKEYKCKVSNKALPAPI
EKTISKAKGQPREPQVYTLPPSRDELTKNQVSLTCLVKGFYPSDIAVE
WESNGQPENNYKTTPPVLDSDGSFFLYSKLTVDKSRWQQGNVFSCSVM
HEALHNHYTQKSLSLSPGK SEQ ID NO: 19 Rituximab light chain
QIVLSQSPAILSASPGEKVTMTCRASSSVSYIHWFQQKPGSSPKPWIY
ATNLASGVPVRFSGSGSGTSYSLTISRVEAEDAATYYCQQWTSNPPTF
GGGTKLEIKRTVAAPSVFIFPPSDEQLKSGTASVVCLLNNFYPREAKV
QWKVDNALQSGNSQESVTEQDSKDSTYSLSSTLTLSKADYEKHKVYAC
EVTHQGLSSPVTKSFNRGEC In some embodiments, the N-glycan is attached to the Asn-297 of the Fc region of Rituximab.

Figure 13:
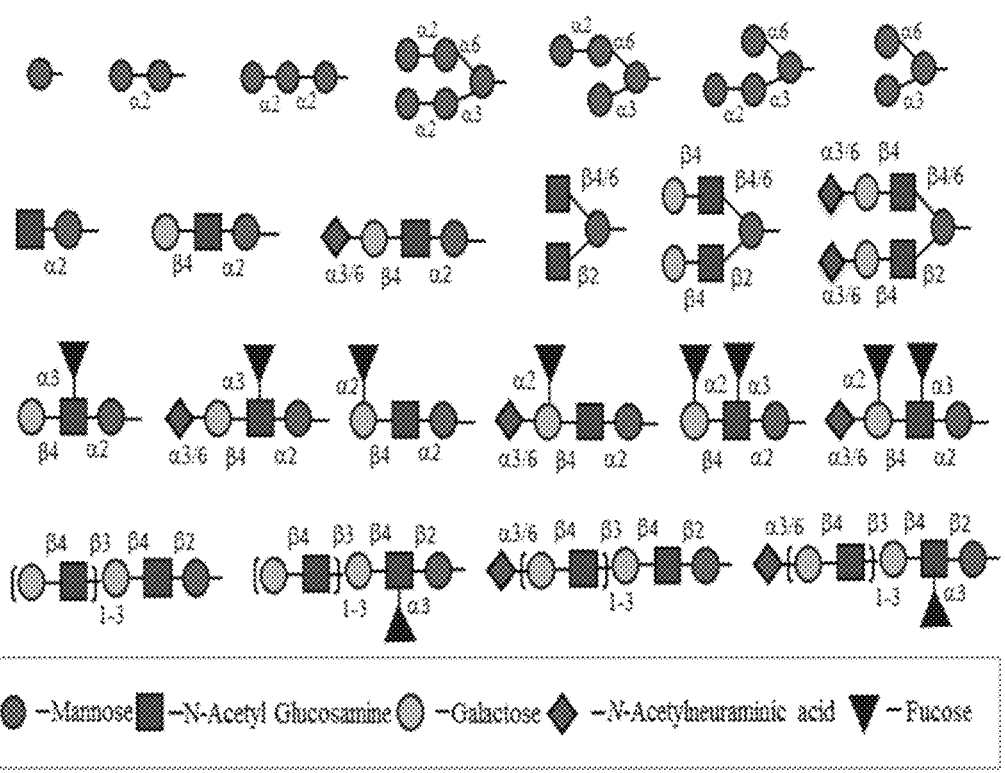
FIG. 13 shows structures of various glycosyl groups that can be used with embodiments of the invention.

The N-glycans according to the invention may have high mannose, hybrid and bi- and tri-antennary complex type structures, wherein the N-glycan structures having general formula:

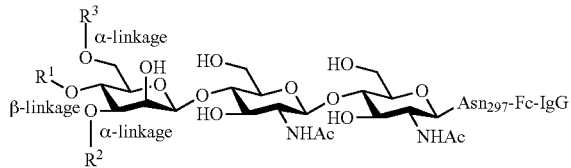

wherein, $R^1$ is —H or N-acetyl glucosamine attached via a β-1,4 linkage and $R^2$ and $R^3$ are same or different and are independently selected from the glycosyl groups shown in FIG. 13.

In some embodiments, the N-glycans described herein may have additional intrachain substitutions comprising "bisecting" GlcNAc, α-1,2 fucose, α-1,3 fucose, with or without an α-2,3 and/or α-2,6 sialic acids, and may be extended poly LacNAc motifs.

In some embodiments, the high mannose type N-glycan described herein are selected from group consisting of $Man_3GlcNAc$, $Man_5GlcNAc$, $Man_6GlcNAc$, $Man_7GlcNAc$, $Man_8GlcNAc$, and $Man_9GlcNAc$. In preferred embodiments, the high mannose type N-glycan is $Man_5GlcNAc$.

In some embodiments, the hybrid type N-glycans described herein comprise at least one α-2,6 or α-2,3 terminal sialic acid, or at least one terminal galactose, or at least one terminal GlcNAc on the alpha-1,3 arm, while the alpha-1,6 arm contains trimannose residues.

In some embodiments, the complex type glycans are of bi-, tri- or tetra-antennary complex types.

In some embodiments, the bi-antennary complex type N-glycans described herein comprise at least one α-2,6 or α-2,3 terminal sialic acid. In preferred embodiments, the N-glycans comprise two α-2,6 and/or α-2,3 terminal sialic acids.

In some embodiments, the bi-antennary complex type N-glycans described herein comprise at least one terminal galactose or GlcNAc. In preferred embodiments, the N-glycans comprise two terminal galactose and/or GlcNAc.

In some embodiments, the bi-antennary complex type N-glycans described herein comprise at least one alpha-1,2 fucose. In preferred embodiments, the N-glycans comprise two alpha-1,2 fucoses.

In some embodiments, the bi-antennary complex type N-glycans described herein comprises at least one alpha-1,3 fucose. In preferred embodiments, the N-glycans comprise two alpha-1,3 fucoses.

In some embodiments, the bi-antennary complex type N-glycans described herein comprise bisecting GlcNAc.

In some embodiments, the bi-antennary complex type N-glycans described herein comprise at least one LacNAc repeat unit. In preferred embodiments, the N-glycans comprise two LacNAc repeat units.

In some embodiments, the tri-antennary complex type N-glycans described herein comprise at least one α-2,6 or α-2,3 terminal sialic acid. In preferred embodiments, the N-glycans comprise three α-2,6 and/or α-2,3 terminal sialic acids.

In some embodiments, the tri-antennary complex type N-glycans described herein comprise at least one terminal galactose or GlcNAc. In preferred embodiments, the N-glycans comprise three terminal galactose and/or GlcNAc.

In some embodiments, the complex type glycans are of bi-, tri- or tetra-antennary complex types, comprising asymmetric antennae on either the alpha-1,3 or alpha-1,6 arm.

In some embodiments, the hybrid and bi- or tri-antennary complex type N-glycans described herein comprise α-2,6 or α-2,3 terminal sialic acid. In a preferred embodiments, the hybrid and bi-, tri- and tetra-complex type N-glycans comprise α-2,6 terminal sialic acid.

Preferably, the N-glycans according to embodiments of the invention are free of core fucose.

Table 4 lists exemplary N-glycans in anti-CD20 glycoengineered antibodies. Embodiments of the present disclosure may include or exclude any of the N-glycans listed herein.

TABLE 4

| Glycan Type | Glycoengineered Rituximab |
| --- | --- |
| High mannose type | Rtx-G1 |
|  | Rtx-G2 |
| Hybrid Type | Rtx-G3 |
|  | Rtx-G4 |
| Tri-antennary Complex Type | Rtx-G5 |
|  | Rtx-G6 |
| Bi-antennary Complex Type | Rtx-G7 |
|  | Rtx-G8 |
|  | Rtx-G9 |
|  | Rtx-G10 |
|  | Rtx-G11 |
|  | Rtx-G12 |
|  | Rtx-G13 |
|  | Rtx-G14 |
|  | Rtx-G15 |
|  | Rtx-G16 |

Figure 15:
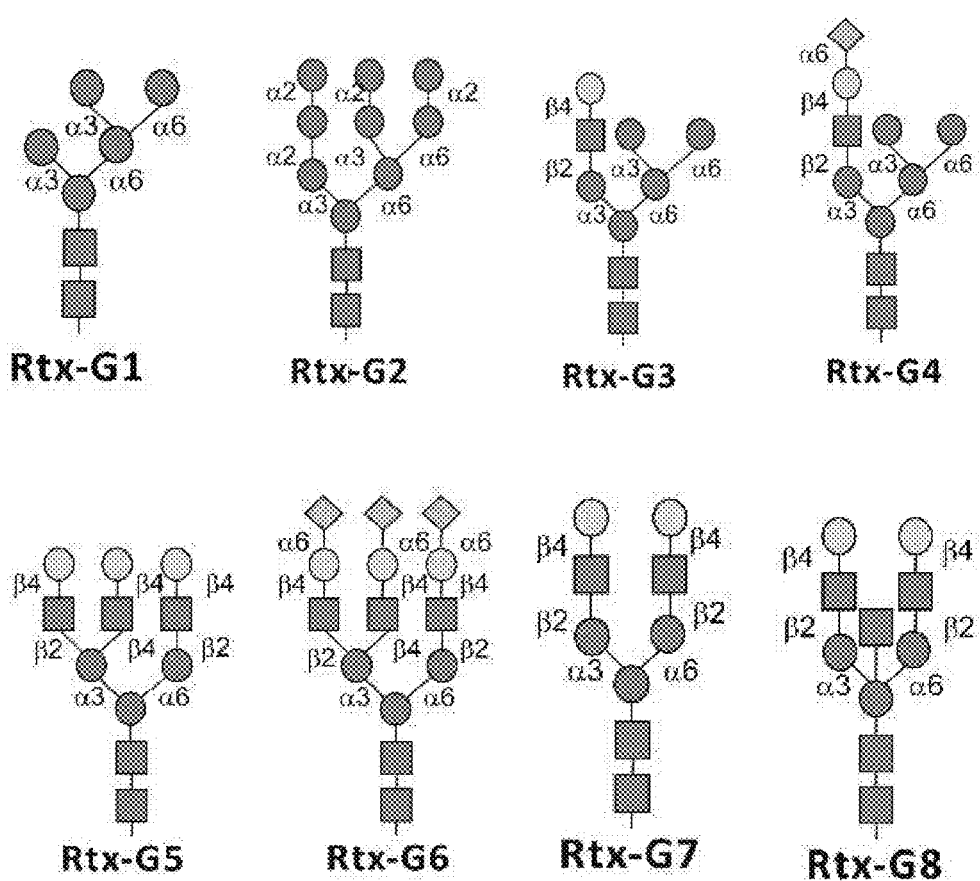
FIG. 15 shows schematics of structures of glycoengineered Rituximabs, (Rtx-G1-Rtx-G16) in accordance with embodiments of the invention.

Note:
the structures of Rtx-G1-Rtx-G16 are shown in FIG. 15.

Biological Functions of Glycoengineered Rituximab

Fc-glycosylation of a variety of antibodies greatly influence the effector-mediated functions, including ADCC, CDC, and circulating half-life. ADCC enhancement is a key strategy for improving therapeutic antibody drug efficacy. It has the potential of lowering effective drug dosage for the benefits of lower drug cost. The glycoengineered anti-CD20 antibodies described herein have cell growth inhibitory activities including apoptosis against human CD20 expressing cells. In some embodiments, the glycoengineered anti- CD20 antibodies exhibits more potent cell growth inhibitory activities, as compared to its parent antibody.

Binding Between FcγRIIIA and Glycoengineered Rituximab

Table 5 lists exemplary FcγRIIIA binding of anti-CD20 glycoengineered antibodies and Rituximab.

TABLE 5

Bindings of FcγRIIIA to glycoengineered Rituximabs using ELISA

| Glycoform | $EC_{50}$ (ng/mL) | Maxi binding (A450 nm) | $EC_{50}$ improvement Folds | Note |
|---|---|---|---|---|
| Commercial Rituximab | 1045 | 1.2 | 1 | Category A: increase >30% |
| Rtx-G1 | 160 | 1.4 | 6.5 | |
| Rtx-G2 | 1050 | 1.1 | ~1 | |
| Rtx-G3 | 320 | 1.3 | 3.2 | Category B: |
| Rtx-G4 | 394 | 1.2 | 2.7 | |
| Rtx-G5 | 31 | 2.6 | 35 | increase >15-30% |
| Rtx-G6 | 32 | 2.8 | 34 | |
| Rtx-G7 | 31 | 2.5 | 35 | Category C: increase >5-10% |
| Rtx-G8 | 34 | 2.3 | 32 | |
| Rtx-G9 | 61 | 2.4 | 17 | |
| Rtx-G10 | 43 | 2.2 | 26 | |
| Rtx-G11 | 199 | 2.4 | 5.4 | Category D: No change |
| Rtx-G12 | 33 | 2.6 | 33 | |
| Rtx-G13 | 48 | 2.6 | 22 | |
| Rtx-G14 | 33 | 2.4 | 33 | |
| Rtx-G15 | 34 | 2.3 | 32 | |
| Rtx-G16 | 32 | 2.5 | 34 | |

FcγRIIIA binding may be measured using assays known in the art. Exemplary assays are described in the examples. The Fc receptor binding may be determined as the relative ratio of anti-CD20 glycoengineered antibodies vs. Rituximab. Fc receptor binding in exemplary embodiments is increased by at least 2.5-fold, 3-fold, 4-fold, 5-fold, 6-fold, 7-fold, 8-fold, 9-fold, 10-fold, 11-fold or 20-fold, 30-fold or higher. High mannose series Man$_9$GlcNAc2 glycoforms are unable to offer promising binding. However, Man$_5$GlcNAc2 glycoform was better than the non-modified Rituximab. Both hybrid type glycoforms could only achieve 2-3 folds enhanced binding to FcγRIIIA Interestingly, all the complex type glycoforms, including bi- and tri-antennary types, provided more than 30-folds enhanced bindings to FcγRIIIA, as compared to the original Rituximab. Having alpha-1,3 fucose on GlcNAc showed no major effect on the FcγRIIIA binding. However, 1,2 fucose slightly reduced the binding. Furthermore, having multiple antennae, such as those present in the tri-antennary glycoform, showed no major contribution in the binding. However, it is believed that glycans with increased sialic acid contents might gain anti-inflammatory activities.

As compared to Rituximab, the binding data showed that the glycoengineered anti-CD20 antibodies, particularly those having complex glycoforms, exhibit stronger binding affinities for the FcγRIIIA ADCC Activities of Glycoengineered Rituximab The ADCC activity of the glycoengineered rituximab's according to the invention is at least 3 fold increased, preferably at least 9 fold, more preferably at least 10 fold increased ADCC activity, preferably at least 12 fold increased ADCC activity, preferably at least 20 fold increased ADCC activity, most preferred at least 30 fold increased ADCC activity compared to the ADCC activity of the parental antibody.

Table 6 lists exemplary enhanced ADCC activities of selected glycoengineered anti-CD20 antibodies and commercial Rituximab. Exemplary assays are described in the examples.

TABLE 6

| Glycoform | $R^2$ | $EC_{50}$ [ng/mL] | Maximal cell lysis (%) | Folds |
|---|---|---|---|---|
| Commercial Rituximab | 0.987 | 13.55 | 27.79 | 1 |
| Rtx-G5 | 0.946 | 2.181 | 32.02 | 6.55 |
| Rtx-G6 | 0.954 | 2.927 | 39.18 | 4.6 |
| Rtx-G14 | 0.942 | 2.323 | 38.76 | 5.8 |
| Rtx-G15 | 0.968 | 1.911 | 37.98 | 7.0 |

A series of anti-CD20 glycoengineered antibodies disclosed by present invention, in particular those with complex glycoforms, exhibit enhanced ADCC activities, as compared to the parental antibody, Rituximab. It is contemplated that the glycoengineered antibodies of the invention may exhibit superior effect as therapeutic agents for B cell-mediated malignant tumors and immunological diseases, in which B cells or antibodies produced by B cells are involved. An object of the present invention is to use the anti-CD20 glycoengineered antibodies in development of therapeutic agents.

Taken together, anti-CD20 glycoengineered antibodies, exhibit enhanced ADCC activities and stronger FcγRIIIA binding affinities, as compared to Rituximab. The glycoantibodies of the invention may provide a superior clinical response either alone or, in a composition comprising two or more such antibodies, and optionally in combination with other treatments such as chemotherapy. The ADCC-enhanced anti-CD20 glycoengineered antibody may provide an alternative therapeutic for B-cell lymphoma and other diseases. The glycoengineered antibodies of the present invention advantageously can be used to alter current routes of administration and current therapeutic regimens, as their increased effector function means they can be dosed at lower concentrations and with less frequency, thereby reducing the potential for antibody toxicity and/or development of antibody tolerance. Furthermore, the improved effector function yields new approaches to treating clinical indications that have previously been resistant or refractory to treatment with the corresponding anti-CD20 monoclonal antibody produced in recombinant host systems.

A Method of Glycoengineering of Anti-CD20 Antibodies

The anti-CD20 glycoengineered antibodies of the invention can be produced by Fc glycoengineering from any anti-CD20 monoclonal antibodies ("parental antibodies"), which may be commercially available or in the preclinical or clinical development. Fc glycoengineering may be performed enzymatically or chemoenzymatically. In a preferred embodiment, the parental antibody is Rituximab.

The N-glycans in the glycoengineered antibodies of the invention are preferably defucosylated.

Disclosed herein includes an improved method for making glycoengineered antibodies, such as an anti-CD20 glycoengineered antibody. A method of the invention may comprise the steps of (a) contacting an anti-CD20 monoclonal antibody with an α-fucosidase and endoglycosidase, thereby yielding a defucosylated antibody having a single N-acetylglucosamine (GlcNAc), and (b) adding a carbohydrate moiety to GlcNAc under suitable conditions.

In some embodiments, the anti-CD20 monoclonal antibody according to the method of the invention is Rituximab.

Any suitable endoglycosidase may be used to trim off the variable portions of an oligosaccharide in N-glycan. Examples of endoglycosidases used herein include EndoS2.

Step (a) in the method of the invention leads to a defucosylated antibody having a single N-acetylglucosamine (GlcNAc). Subsequently, EndoS2 mutants mediate transglycosylations to add a broad range of selected carbohydrate moieties to GlcNAc to extend the sugar chain. A homogenous population of glycoantibodies can therefore be produced. Examples of transglycosylases as described herein include the selected mutants of EndoS2 having the sequences of SEQ ID NOs. 2-17.

In some embodiments, the carbohydrate moieties according to embodiments of the invention may comprise diverse N-glycans of high mannose, hybrid and complex types having the formula:

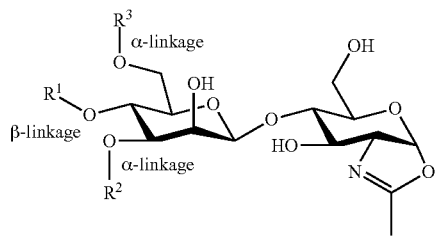

wherein, $R^1$ is —H or N-acetyl glucosamine attached via a β-1,4 linkage and $R^2$ and $R^3$ are same or different and are independently selected from the glycosyl groups shown in FIG. 13.

In some embodiments, the carbohydrate moiety is a sugar oxazoline.

Suitable conditions also include incubation of the reaction mixture for at least 20 minutes, 30 minutes, 40 minutes, 50 minutes, 60 minutes, 70 minutes, 80 minutes, 90 minutes or 100 minutes, preferably less than 60 minutes. Incubation preferably takes place at room temperature, more preferably at approximately 20° C., 25° C., 30° C., 35° C., 40° C. or 45° C., and most preferably at approximately 37° C.

Pharmaceutical Formulations

Therapeutic formulations comprising an antibody of the invention may be prepared for storage by mixing the antibody having the desired degree of purity with one or more optional physiologically acceptable carriers, excipients or stabilizers (Remington's Pharmaceutical Sciences 16th edition, Osol, A. Ed. (1980)), in the form of aqueous solutions, lyophilized or other dried formulations. Acceptable carriers, excipients, or stabilizers are nontoxic to recipients at the dosages and concentrations employed, and include buffers such as phosphate, citrate, histidine and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulation herein may also contain more than one active compound as necessary for the particular indication being treated, including, but not limited to, those with complementary activities that do not adversely affect each other. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the immunoglobulin of the invention, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(—)-3-hydroxybutyric acid. While polymers such as ethylene-vinyl acetate and lactic acid-glycolic acid enable release of molecules for over 100 days, certain hydrogels release proteins for shorter time periods. When encapsulated immunoglobulins remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

The amount of antibody in the pre-lyophilized formulation is determined taking into account the desired dose volumes, mode(s) of administration etc. Where the protein of choice is an intact antibody (a full-length antibody), from about 2 mg/mL to about 50 mg/mL, preferably from about 5 mg/mL to about 40 mg/mL and most preferably from about 20-30 mg/mL is an exemplary starting protein concentration. The protein is generally present in solution. For example, the protein may be present in a pH-buffered solution at a pH from about 4-8, and preferably from about 5-7. Exemplary buffers include histidine, phosphate, Tris, citrate, succinate and other organic acids. The buffer concentration can be from about 1 mM to about 20 mM, or from about 3 mM to about 15 mM, depending, for example, on the buffer and the desired isotonicity of the formulation (e.g. of the reconstituted formulation). The preferred buffer is histidine in that, as demonstrated below, this can have lyoprotective properties. Succinate was shown to be another useful buffer.

The lyoprotectant is added to the pre-lyophilized formulation. In preferred embodiments, the lyoprotectant is a non-reducing sugar such as sucrose or trehalose. The amount of lyoprotectant in the pre-lyophilized formulation is generally such that, upon reconstitution, the resulting formulation will be isotonic. However, hypertonic reconstituted formulations may also be suitable. In addition, the amount of lyoprotectant must not be too low such that an unacceptable amount of degradation/aggregation of the protein occurs upon lyophilization. Where the lyoprotectant is a sugar (such as sucrose or trehalose) and the protein is an antibody, exemplary lyoprotectant concentrations in the pre-lyophilized formulation are from about 10 mM to about 400 mM, and preferably from about 30 mM to about 300 mM, and most preferably from about 50 mM to about 100 mM.

The ratio of protein to lyoprotectant is selected for each protein and lyoprotectant combination. In the case of an antibody as the protein of choice and a sugar (e.g., sucrose or trehalose) as the lyoprotectant for generating an isotonic reconstituted formulation with a high protein concentration, the molar ratio of lyoprotectant to antibody may be from about 100 to about 1500 moles lyoprotectant to 1 mole antibody, and preferably from about 200 to about 1000 moles of lyoprotectant to 1 mole antibody, for example from about 200 to about 600 moles of lyoprotectant to 1 mole antibody.

In preferred embodiments of the invention, it has been found to be desirable to add a surfactant to the pre-lyophilized formulation. Alternatively, or in addition, the surfactant may be added to the lyophilized formulation and/or the reconstituted formulation. Exemplary surfactants include nonionic surfactants such as polysorbates (e.g. polysorbates 20 or 80); poloxamers (e.g. poloxamer 188); Triton; sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g lauroamidopropyl); myristamidopropyl palmidopropyl-, or isostearamidopropyl-dimethylamine; sodium methyl cocoyl-, or disodium methyl oleyl-taurate; and the MONAQUAT™ series (Mona Industries, Inc., Paterson, N.J.), polyethyl glycol, polypropyl glycol, and copolymers of ethylene and propylene glycol (e.g. Pluronics, PF68 etc). The amount of surfactant added is such that it reduces aggregation of the reconstituted protein and minimizes the formation of particulates after reconstitution. For example, the surfactant may be present in the pre-lyophilized formulation in an amount from about 0.001-0.5%, and preferably from about 0.005-0.05%.

In certain embodiments of the invention, a mixture of the lyoprotectant (such as sucrose or trihalose) and a bulking agent (e.g. mannitol or glycine) is used in the preparation of the pre-lyophilization formulation. The bulking agent may allow for the production of a uniform lyophilized cake without excessive pockets therein etc.

Other pharmaceutically acceptable carriers, excipients or stabilizers such as those described in Remington's Pharmaceutical Sciences 16th edition, Osol, A. Ed. (1980) may be included in the pre-lyophilized formulation (and/or the lyophilized formulation and/or the reconstituted formulation) provided that they do not adversely affect the desired characteristics of the formulation. Acceptable carriers, excipients or stabilizers are nontoxic to recipients at the dosages and concentrations employed and include; additional buffering agents; preservatives; co-solvents; antioxidants including ascorbic acid and methionine; chelating agents such as EDTA; metal complexes (e.g. Zn-protein complexes); biodegradable polymers such as polyesters; and/or salt-forming counterions such as sodium.

The pharmaceutical compositions and formulations described herein are preferably stable. A "stable" formulation/composition is one in which the antibody therein essentially retains its physical and chemical stability and integrity upon storage. Various analytical techniques for measuring protein stability are available in the art and are reviewed in Peptide and Protein Drug Delivery, 247-301, Vincent Lee Ed., Marcel Dekker, Inc., New York, N.Y., Pubs. (1991) and Jones, A. Adv. Drug Delivery Rev. 10: 29-90 (1993). Stability can be measured at a selected temperature for a selected time period.

The formulations to be used for in vivo administration must be sterile. This is readily accomplished by filtration through sterile filtration membranes, prior to, or following, lyophilization and reconstitution. Alternatively, sterility of the entire mixture may be accomplished by autoclaving the ingredients, except for protein, at about 120° C. for about 30 minutes, for example.

After the protein, lyoprotectant and other optional components are mixed together, the formulation is lyophilized. Many different freeze-dryers are available for this purpose such as Hull50® (Hull, USA) or GT20® (Leybold-Heraeus, Germany) freeze-dryers. Freeze-drying is accomplished by freezing the formulation and subsequently subliming ice from the frozen content at a temperature suitable for primary drying. Under this condition, the product temperature is below the eutectic point or the collapse temperature of the formulation. Typically, the shelf temperature for the primary drying will range from about −30 to 25° C. (provided the product remains frozen during primary drying) at a suitable pressure, ranging typically from about 50 to 250 mTorr. The formulation, size and type of the container holding the sample (e.g., glass vial) and the volume of liquid will mainly dictate the time required for drying, which can range from a few hours to several days (e.g. 40-60 hrs). A secondary drying stage may be carried out at about 0-40° C., depending primarily on the type and size of container and the type of protein employed. However, it was found herein that a secondary drying step may not be necessary. For example, the shelf temperature throughout the entire water removal phase of lyophilization may be from about 15-30° C. (e.g., about 20° C.). The time and pressure required for secondary drying will be that which produces a suitable lyophilized cake, dependent, e.g., on the temperature and other parameters. The secondary drying time is dictated by the desired residual moisture level in the product and typically takes at least about 5 hours (e.g. 10-15 hours). The pressure may be the same as that employed during the primary drying step. Freeze-drying conditions can be varied depending on the formulation and vial size.

In some instances, it may be desirable to lyophilize the protein formulation in the container in which reconstitution of the protein is to be carried out in order to avoid a transfer step. The container in this instance may, for example, be a 3, 5, 10, 20, 50 or 100 cc vial. As a general proposition, lyophilization will result in a lyophilized formulation in which the moisture content thereof is less than about 5%, and preferably less than about 3%.

At the desired stage, typically when it is time to administer the protein to the patient, the lyophilized formulation may be reconstituted with a diluent such that the protein concentration in the reconstituted formulation is at least 50 mg/mL, for example from about 50 mg/mL to about 400 mg/mL, more preferably from about 80 mg/mL to about 300 mg/mL, and most preferably from about 90 mg/mL to about 150 mg/mL. Such high protein concentrations in the reconstituted formulation are considered to be particularly useful where subcutaneous delivery of the reconstituted formulation is intended. However, for other routes of administration, such as intravenous administration, lower concentrations of the protein in the reconstituted formulation may be desired (for example from about 5-50 mg/mL, or from about 10-40 mg/mL protein in the reconstituted formulation). In certain embodiments, the protein concentration in the reconstituted formulation is significantly higher than that in the pre-lyophilized formulation. For example, the protein concentration in the reconstituted formulation may be about 2-40 times, preferably 3-10 times and most preferably 3-6 times (e.g. at least three fold or at least four fold) that of the pre-lyophilized formulation.

Reconstitution generally takes place at a temperature of about 25° C. to ensure complete hydration, although other temperatures may be employed as desired. The time required for reconstitution will depend, e.g., on the type of diluent, amount of excipient(s) and protein. Exemplary diluents include sterile water, bacteriostatic water for injection (BWFI), a pH buffered solution (e.g. phosphate-buffered saline), sterile saline solution, Ringer's solution or dextrose solution. The diluent optionally contains a preservative. Exemplary preservatives have been described above, with aromatic alcohols such as benzyl or phenol alcohol being the preferred preservatives. The amount of preservative employed is determined by assessing different preservative concentrations for compatibility with the protein and preservative efficacy testing. For example, if the preservative is an aromatic alcohol (such as benzyl alcohol), it can be present in an amount from about 0.1-2.0% and preferably from about 0.5-1.5%, but most preferably about 1.0-1.2%. Preferably, the reconstituted formulation has less than 6000 particles per vial which are >10 µm in size.

Therapeutic Applications

The glycoengineered antibodies described herein may be used for treating a patient having a cancer. The method of the treatment comprises administering to the patient an effective amount of a glycoengineered antibody or a pharmaceutical composition described herein. Examples of the cancers include, but are not limited to, B cell lymphomas, NHL, precursor B cell lymphoblastic leukemia/lymphoma and mature B cell neoplasms, B cell chronic lymphocytic leukemia (CLL)/small lymphocytic lymphoma (SLL), B cell prolymphocytic leukemia, lymphoplasmacytic lymphoma, mantle cell lymphoma (MCL), follicular lymphoma (FL), low-grade, intermediate-grade and high-grade (FL), cutaneous follicle center lymphoma, marginal zone B cell lymphoma, MALT type marginal zone B cell lymphoma, nodal marginal zone B cell lymphoma, splenic type marginal zone B cell lymphoma, hairy cell leukemia, diffuse large B cell lymphoma, Burkitt's lymphoma, plasmacytoma, plasma cell myeloma, post-transplant lymphoproliferative disorder, Waldenstrom's macroglobulinemia, and anaplastic large-cell lymphoma (ALCL).

In certain embodiments, the cancer is B-cell lymphoma such as non-Hodgkin's lymphoma.

Further, the glycoengineered antibodies described herein may be used for treating a patient having an autoimmune or inflammatory disease. The method of the treatment comprises administering to the patient an effective amount of a glycoengineered antibody or a pharmaceutical composition described herein. Examples of the autoimmune or inflammatory disease include, but are not limited to, rheumatoid arthritis, juvenile rheumatoid arthritis, systemic lupus erythematosus (SLE), Wegener's disease, inflammatory bowel disease, idiopathic thrombocytopenic purpura (ITP), thrombotic thrombocytopenic purpura (TTP), autoimmune thrombocytopenia, multiple sclerosis, psoriasis, IgA nephropathy, IgM polyneuropathies, myasthenia gravis, vasculitis, diabetes mellitus, Reynaud's syndrome, Crohn's disease, ulcerative colitis, gastritis, Hashimoto's thyroiditis, ankylosing spondylitis, hepatitis C-associated cryoglobulinemic vasculitis, chronic focal encephalitis, bullous pemphigoid, hemophilia A, membranoproliferative glomerulnephritis, adult and juvenile dermatomyositis, adult polymyositis, chronic urticaria, primary biliary cirrhosis, neuromyelitis optica, Graves' dysthyroid disease, bullous pemphigoid, membranoproliferative glonerulonephritis, Churg-Strauss syndrome, asthma, psoriatic arthritis, dermatitis, respiratory distress syndrome, meningitis, encephalitits, uveitis, eczema, atherosclerosis, leukocyte adhesion deficiency, juvenile onset diabetes, Reiter's disease, Behcet's disease, hemolytic anemia, atopic dermatitis, Wegener's granulomatosis, Omenn's syndrome, chronic renal failure, acute infectious mononucleosis, HIV and herpes-associated disease, systemic sclerosis, Sjorgen's syndrome and glomerulonephritis, dermatomyositis, ANCA, aplastic anemia, autoimmune hemolytic anemia (AIHA), factor VIII deficiency, hemophilia A, autoimmune neutropenia, Castleman's syndrome, Goodpasture's syndrome, solid organ transplant rejection, graft versus host disease (GVHD), autoimmune hepatitis, lymphoid interstitial pneumonitis (HIV), bronchiolitis obliterans (non-transplant), Guillain-Barre Syndrome, large vessel vasculitis, giant cell (Takayasu's) arteritis, medium vessel vasculitis, Kawasaki's Disease, and polyarteritis nodosa.

In certain embodiments, the autoimmune or inflammatory disease is rheumatoid arthritis.

In these treatment methods, the anti-CD20 glycoengineered antibody can be administered alone or in conjunction with a second therapeutic agent such as a second antibody, or a chemotherapeutic agent or an immunosuppressive agent. The second antibody can be one that binds CD20 or a different B cell antigen, or a NK or T cell antigen.

Embodiments of the invention will be further illustrated with the following specific examples. One skilled in the art would appreciate that these specific examples are for illustration only and that other modifications and variations are possible without departing from the scope of the invention. For example, the EndoS2 mutants of the invention may be used to glycoengineer any glycoproteins or glycopeptides, including antibodies. The specific examples described herein use anti-CD20 antibodies. However, one skilled in the art would appreciate that other glycoproteins or antibodies may also be used in a similar manner.

Material and Methods

Monoclonal antibody Rituximab was purchased commercial source or in-house produced. N-glycans of high mannose, hybrid and complex type were synthesized according to previously reported procedures. (20, 21).

Clone Constructions, Overexpression, and Purification of EndoS2 and Mutants

The EndoS2 encoding gene, ndoS2, from *Streptococcus pyogenes* GAS NZ131, was synthesized and subcloned into the pET28a expression vector. The signal peptide sequence (amino acid 1-36) of ndoS2 was replaced by a $His_6$-tag on its N-terminal. The mutants of ndoS2 were generated by site-directed mutagenesis according to the manufacturer's instructions (Agilent Technologies) that PCR reactions were performed by using ndoS2 expression vector as a template and oligonucleotide pairs containing desired mutation as primers. Then, the amplified DNA was treated with DpnI and transformed into DH5a competent cells. The mutated sequences were confirmed by DNA sequencing (Genomics). After the transformation into BL21 (DE3) competent cells for expression, cells were induced with 0.1 mM isopropyl-β-D-thiogalactopyranoside (IPTG), the recombinant EndoS2 mutant proteins with their $His_6$ tag were expressed at 20° C. for 16 h and pelleted by centrifugation at 6500 rpm for 30 min. The cells were resuspended in lysis buffer (30 mM HEPES, pH 8.0, 300 mM NaCl) and disrupted using Ultrasonic Processor (10 min, 4 s-on/5 s-off, ChromTech). The total cell lysates were centrifuged at 10000 rpm for 45 min and the soluble recombinant EndoS2 and mutant proteins were purified by immobilized metal-ion chromatography with a Ni-NTA column (GE Healthcare). The eluted protein fractions were collected and concentrated against storage buffer (30 mM HEPES, pH 8.0, 100 mM NaCl) by using Amicon ultra centrifugal filters 10 kDa. Concentrated protein samples were analyzed by SDS-PAGE, and protein concentration was quantified using a Nano-Drop 2000c spectrophotometer. The yield of overproduction of the wild-type EndoS2 was approximately 35 mg/L, and the yield for the mutants was approximately 25 mg/L.

Preparation of GlcNAc-Rituximab from Commercially Available Rituximab

Rituximab (2.5 mg, from commercial source) in 1.25 ml 50 mM sodium phosphate buffer pH 7.0 was incubated with EndoS2 (125 βg) and fucosidase (2.5 mg) at 37° C. for 22 h. After the complete cleavage of the N-glycans on the heavy chain, as checked by SDS-PAGE analyses, the reaction mixture was then subjected to affinity chromatography on a column of 1 ml protein A-agarose resin preequilibrated with 20 mM sodium phosphate pH 7.0. After washing, the bound IgG was eluted with 10 ml 50 mM glycine HCl pH3.0. The elution fractions were immediately neutralized with 1 M Tris-Cl pH 8.3 and concentrated by centrifugal filtration (Amicon Ultra centrifugal filter) to give GlcNAc-Rituximab (1.93 mg). The product was trypsinized, and the glycopeptides, TKPREEQYNSTYR and EEQYNSTYR were analyzed using nanospray LC/MS to confirm the glycosylation pattern of GlcNAc-Rituximab.

Preparation of Glycan-Oxazolines

A solution of respective glycan (3-5 mg), 2-chloro-1,3-dimethylimidazolinium chloride (DMC) (6-10 mg) and $Et_3N$ (10-20 μL) in water (300-500 μL) was stirred at 4° C. for 1 h. The reaction mixture was subjected to gel filtration chromatography on a Sephadex G-25 column eluted by 0.05% aqueous $Et_3N$. The fractions containing the products G1-G16 (glycan oxazolines) were combined and lyophilized to give a white powder (2.5-4 mg, Yield ~80-90%).

Hydrolytic Activity Assay of EndoS2 and its Mutants

A solution containing 52 μM rituximab (400 μg) and 52 nM EndoS2 or its selected mutant proteins in 100 mM HEPES buffer pH 7.0 was incubated at 37° C. with 700 rpm shaking. At the indicated time points, 2 μg aliquots were taken and analyzed by 10% SDS-PAGE. Rituximab with glycan hydrolyzed would display faster migration on PAGE. The relative percentage of hydrolyzed product was calculated by using Image J software based on the intensity of bands on SDS-PAGE (FIG. 3).

Transglycosylation Activity Assay of EndoS2 and its Mutants Using SCT-Oxazoline as Donor Substrate A solution containing 67.5 μM mono GlcNAc-Rituximab (400 μg) and 2.5 mM sialylated complex type glycan (SCT)-oxazoline (200 μg) in 100 mM HEPES buffer pH 7.0 was incubated with 67.5 nM EndoS2 or selected mutant proteins at 37° C. with 700 rpm shaking. At the indicated time points, 2 μg aliquots were taken and analyzed by 10% SDS-PAGE. Glycosylated Rituximab would display slower migration on PAGE. The relative percentage of Rituximab-SCT was calculated by using Image J software based on the intensity of bands on SDS-PAGE.

Transglycosylation of GlcNAc-Rituximab with Various Glycan Oxazoline Using EndoS2 Mutants General procedure: To a mixture of EndoS2 mutants (16.8 μM) and GlcNAc-Rituximab (2 mg, 0.337 mM) in 100 mM HEPES buffer (pH 7.0) was added glycan oxazoline (2-3 mg) and incubated at 37° C. with 700 rpm shaking for 1 to 2 h. The reaction was quenched by adding 0.1 mM of EDTA solution. The reaction mixture was purified with protein A affinity column, followed by amanion exchange column capto Q to collect the desired product, anti-CD20 glycoengineered Rituximab. The product was trypsinized, and the glycopeptides, TKPREEQYNSTYR and EEQYNSTYR, were analyzed using nanospray LC/MS to confirm the desired glycosylation pattern.

Table 7 lists the optimized reaction details for preparation of each of the Rituximab glycoforms

TABLE 7

| Starting Material | Rituximab Glycoform | EndoS2 mutants | Enzyme ratio | Glycan oxazoline | Glycan amount | Reaction time |
|---|---|---|---|---|---|---|
| GlcNAc-Rituximab (2 mg, 0.337 mM) | Rtx-G1 | D226Q | 16.8 μM | G1 | 2 mg | 30 min |
| | Rtx-G2 | T138Q | 33.7 μM | G2 | 3 mg | 30 min |
| | Rtx-G3 | D182Q | 16.8 μM | G3 | 2 mg | 30 min |
| | Rtx-G4 | D226Q | 16.8 μM | G4 | 2 mg | 60 min |
| | Rtx-G5 | D182Q | 16.8 μM | G5 | 3 mg | 30 min |
| | Rtx-G6 | D138Q | 33.7 μM | G6 | 3 mg | 30 min |
| | Rtx-G7 | T138Q | 16.8 μM | G7 | 2 mg | 30 min |
| | Rtx-G8 | T138Q | 16.8 μM | G8 | 2 mg | 30 min |
| | Rtx-G9 | D182Q | 16.8 μM | G9 | 2 mg | 30 min |
| | Rtx-G10 | D182Q | 16.8 μM | G10 | 2 mg | 30 min |
| | Rtx-G11 | D182Q | 16.8 μM | G11 | 2 mg | 60 min |
| | Rtx-G12 | D182Q | 16.8 μM | G12 | 2 mg | 60 min |
| | Rtx-G13 | D138Q | 16.8 μM | G13 | 2 mg | 30 min |
| | Rtx-G14 | D182Q | 16.8 μM | G14 | 3 mg | 60 min |
| | Rtx-G15 | D182Q | 16.8 μM | G15 | 2 mg | 60 min |
| | Rtx-G16 | D182Q | 16.8 μM | G15 | 2 mg | 60 min |

Binding Affinity of Glycoenginnered Anti-CD20 Antibodies to FcγRIIIA

The affinity of the remodeled glycoforms of Rituximab for FcγIIA receptors was examined by ELISA.

Microtiter plate (Corning® 96 Well Clear Flat Bottom Polystyrene High Bind, #9018) was coated with 50 ng/well of recombinant soluble FcγRIIIA diluted in 50 mM Bicarbonate/carbonate coating buffer (pH 10) overnight at 4° C. The plate was then washed 3 times with PBST (0.05% Tween 20 in PBS) and blocked with 5% BSA in PBST for 1 h at room temperature. The binding activity of glycoengineered antibodies (Rtx G1-G16) was determined for serial eight dilutions, starting with concentration of 100 µg/ml in 2% BSA/PBST in duplicates. The plate was incubated for 1 h at room temperature, and washed 3 times with PBST. Next, 100 µl of goat anti-human IgG conjugated to horseradish peroxidase (Jackson immune, #109-035-088) in 2% BSA/PBST was added per well and incubated for 30 min at room temperature. The plate was washed 5 times with PBST then 100 µL per well of TMB substrate (eBioscience, #00-4201-56) was added and the resulting plate was incubated in the dark 15 min at room temperature. The absorbance value was determined at 450 nm in an ELISA reader (Molecular Devices Corporation, Sunnyvale, Calif., USA).

ADCC Activity of Glycoenginnered Anti-CD20 Antibodies

The antibody-mediated ADCC was evaluated using the calcein release assay. Raji cells (human Burkitt's lymphoma cell line) were obtained from BCRC as target cells. Peripheral blood-mononuclear cells (PBMC) were separated from the blood of healthy volunteers using Ficoll-Paque (GE healthcare) as effector cells. The target cells ($1\times10^6$/ml) were labeled for 30 minutes at 37° C. with 10 µM calcein-acetoxymethyl ester (Thermo Fisher Scientific). After washing, labeled target cells were distributed in 96-well plates at a density of $1\times10^4$ cells in 50 µl per well. Antibodies with various concentrations, and effector cells ($2.5\times10^5$ per well) with a 25:1 E/T ratio were then added. After incubation for 4 h at 37° C., cells were sedimented by centrifugation, and 150 µl of supernatants were collected and analyzed by using fluorescence microplate reader to measure the release of calcein. For maximal release, the cells were lysed with 1% Triton X-100. The fluorescence value of the culture medium background was subtracted from that of the experimental results.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

REFERENCE

1. Ecker D. M; Jones S. D; Levine H L., The therapeutic monoclonal antibody market MAbs. 2015, 7(1), 9-14.
2. Reichert J. M., Antibodies to watch in 2015. MAbs. 2015, 7(1):1-8.
3. Dietmar R.; Max L. T., Fc glycans of therapeutic antibodies as critical quality attributes Glycobiology. 2015, 25(12), 1325-1334.
4. Higel F.; Seidl A.; Sörgel F.; Friess W., N-glycosylation heterogeneity and the influence on structure, function and pharmacokinetics of monoclonal antibodies and Fc fusion proteins. Eur. J. Pharm. Biopharm. 2016, 100, 94-100
5. Hodoniczky J.; Zheng Y. Z.; James D. C., Control of recombinant monoclonal antibody effector functions by Fc N-glycan remodeling in vitro. Biotechnol. Prog. 2005, 21(6), 1644-52.
6. Jefferis R., Glycosylation of recombinant antibody therapeutics. Biotechnol. Prog. 2005, 21, 11-16.
7. Nimmerjahn F.; Ravetch J. V., Fcγ receptors as regulators of immune responses. Nat. Rev. Immunol. 2008, 8, 34-47.
8. Adams, G. P.; Weiner, L. M., Monoclonal antibody therapy of cancer. Nat. Biotechnol. 2005, 23, 1147-1157.
9. Parekh R. B.; Dwek R. A.; Sutton B. J.; Fernandes D. L.; Leung A.; Stanworth D.; Rademacher T. W.; Mizuochi T.; Taniguchi T.; Matsuta K., Association of rheumatoid arthritis and primary osteoarthritis with changes in the glycosylation pattern of total serum IgG. Nature. 1985, 316, 6027-37.
10. Golay J.; Da Roit F.; Bologna L.; Ferrara C.; Leusen J. H.; Rambaldi A.; Klein C.; Introna M., Glycoengineered CD20 antibody obinutuzumab activates neutrophils and mediates phagocytosis through CD16B more efficiently than rituximab. Blood. 2013, 122(20), 3482-91.
11. Newkirk M. M.; Novick J.; Stevenson M. M.; Fournier M. J.; Apostolakos P., Differential clearance of glycoforms of IgG in normal and autoimmune-prone mice. Clin. Exp. Immunol. 1996, 106(2), 259-64.
12. Ferrara C.; Grau S.; Jäger C.; Sondermann P.; Brünker P.; Waldhauer I.; Hennig M.; Ruf A.; Rufer A. C.; Stihle M.; Umaña P.; Benz J., Unique carbohydrate-carbohydrate interactions are required for high affinity binding between FcgammaRIII and antibodies lacking core fucose. Proc. Natl. Acad. Sci. USA. 2011, 108(31), 12669-74.
13. Lin C. W; Tsai M. H.; Li S. T., A common glycan structure on immunoglobulin G for enhancement of effector functions. Proc. Natl. Acad. Sci. USA. 2015, 112(34), 10611-6.
14. Durocher Y.; Butler M., Expression systems for therapeutic glycoprotein production. Curr. Opin. Biotechnol. 2009, 20(6), 700-7.
15. Jefferis R., Glycosylation as a strategy to improve antibody-based therapeutics. Nat. Rev. Drug Discov. 2009, 8(3), 226-34.
16. Wang L. X., Chemoenzymatic Glycoengineering of Intact IgG Antibodies for Gain of Functions. J. Am. Chem. Soc. 2012, 134(29), 12308-12318.
17. Collin M.; Olsen A., EndoS, a novel secreted protein from *Streptococcus pyogenes* with endoglycosidase activity on human IgG. EMBO J. 2001, 20(12), 3046-55.
18. Sjögren J; Struwe W. B.; Cosgrave E. F.; Rudd P. M.; Stervander M.; Allhorn M.; Hollands A.; Nizet V.; Collin M., EndoS2 is a unique and conserved enzyme of serotype M49 group A *Streptococcus* that hydrolyses N-linked glycans on IgG and α1-acid glycoprotein. Biochem J. 2013, 455(1), 107-18.
19. Sjögren J.; Collin M., EndoS and EndoS2 hydrolyze Fc-glycans on therapeutic antibodies with different glycoform selectivity and can be used for rapid quantification of high-mannose glycans. Glycobiology. 2015, 25(10), 1053-1063.
20. Shivatare, S. S., Wu, C. Y., Wong, C., H, Efficient convergent synthesis of bi-, tri-, and tetra-antennary complex type N-glycans and their HIV-1 antigenicity. J. Am. Chem. Soc. 2013, 135(41), 15382-91.
21. Shivatare, S. S., Wu, C. Y., Wong, C., H, Modular synthesis of N-glycans and arrays for the hetero-ligand binding analysis of HIV antibodies. Nat. Chem. 2016, 8(4), 338-46.

What is claimed is:

1. A method for preparing an engineered glycoprotein using a mutant endoglycosidase S2 (EndoS2), comprising coupling an activated oligosaccharide to a glycoprotein acceptor, wherein the mutant EndoS2 comprises one or more mutations in the sequence of a wild-type EndoS2 as set forth in SEQ ID NO:1, wherein the one or more mutations are in a peptide region located within residues 133-143, residues 177-178 residue 182, residues 187-189, residues 221-231, and residues 232-237, wherein the mutant of EndoS2 has a hydrolyzing activity lower than that of the wild-type EndoS2 and has a tranglycosylation activity higher than that of the wild-type EndoS2, and wherein the mutation at residue 182 is D182Q.

2. The method according to claim 1, wherein the one or more mutations are at residues T138, D226, T227, and/or T228.

3. The method according to claim 1, wherein the one or more mutations are selected from the group consisting of T138D, T138E, T138F, T138H, T138K, T138L, T138M, T138N, T138Q, T138R, T138V, T138W, D226Q, T227Q, and T228Q.

4. The method according to claim 1, wherein the mutant comprises the sequence of SEQ ID NO.6, SEQ ID NO.7, SEQ ID NO.8, SEQ ID NO.9, SEQ ID NO.10, SEQ ID NO.11, SEQ ID NO.12, SEQ ID NO.13, SEQ ID NO.14, SEQ ID NO.15, SEQ ID NO.16, SEQ ID NO.17, SEQ ID NO. 2, SEQ ID NO. 3, SEQ ID NO. 4, or SEQ ID NO. 5.

5. The method according to claim 1, wherein the activated oligosaccharide is a glycan oxazoline.

6. The method according to claim 5, wherein the glycan oxazoline comprises an N-glycan having the following formula:

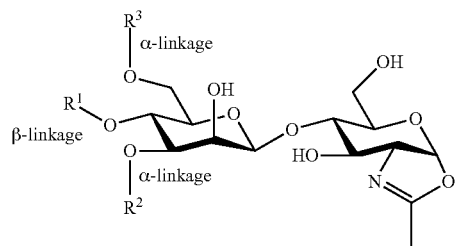

wherein $R^1$ is —H or N-acetyl glucosamine attached via a β-1,4 linkage, and $R^2$ and $R^3$ are same or different and are independently selected from the group consisting of: mannosyl-(Man), di-mannosyl-(Man$_2$), tri-mannosyl-(Man$_3$), biantennary penta-mannosyl-(Man$_2$-(Man$_2$)Man), biantennary tetra-mannosyl-(Man$_2$-(Man)Man), biantennary tri-mannosyl-(Man-(Man)Man), N-acetylglucosamine-mannosyl-(GlcNac-Man), galactose-N-acetylglucosamine-mannosyl-(Gal-GlcNAc-Man), N-acetylneuraminic acid-galactose-N-acetylglucosamine-mannosyl-(Nur5Ac-Gal-GlcNAc-Man), biantennary di-N-acetylglucosamine-mannosyl (GlcNAc)$_2$-Man), biantennary di-(galactose-N-acetylglucosamine)-mannosyl-((Gal-GlcNAc)$_2$-Man), biantennary di-(N-acetyl-neuraminic acid-galactose-N-acetylglucosamine)-mannosyl-((Neu5Ac-Gal-GlcNAc)$_2$-Man), galactose-(fucosyl-N-acetylglucosamine)-mannosyl-(Gal-(Fuc-GlcNAc)-Man), N-acetylneuraminic acid-galactose-(fucosyl-N-acetylglucosamine)-mannosyl-((Neu5Ac-Gal-(Fuc-GlcNAc)-Man), fucosyl-galactose-N-acetylglucosamine-mannosyl-fucosyl-galactose-(fucosyl-N-acetylglucosamine)-mannosyl-(Fuc-Gal-GlcNAc-Man), N-neuraminic acid-(fucose-galactose)-N-acetylglucosamine-mannosyl-(Nur5Ac-(Fuc-Gal)-GlcNAc-Man), fucose-galactose-(fucose-N-acetylglucosamine)-mannosyl-(Fuc-Gal-(Fuc-GlcNAc)-Man), N-neuraminic acid-(fucose-galactose)-(fucose-N-acetylglucosamine)-mannosyl-(Neu5Ac-(Fuc-Gal)-(Fuc-GlcNAc)-Man), (galactose-N-acetylglucosamine)$_n$-galactose-N-acetylglucosamine-mannosyl-(Gal-GlcNAc)$_n$-Gal-GlcNAc-Man), (galactose-N-acetylglucosamine)$_n$-galactose-(fucose-N-acetylglucosamine)-mannosyl-((Gal-GlcNAc)$_n$-Gal-(Fuc-GlcNAc)-Man), N-acetylneuraminic acid-(galactose-N-acetylglucosamine)$_n$-galactose-N-acetylglucosamine)-mannosyl-(Neu5Ac-(Gal-GlcNAc)$_n$-Gal-GlcNAc-Man), and N-acetylneuraminic acid-(galactose-N-acetylglucosamine)$_n$-galactose-(fucose-N-acetylglucosamine)-mannosyl-(Neu5Ac-(Gal-GlcNAc)$_n$-Gal-(Fuc-GlcNAc)-Man), wherein n is an integer from 1 to 3.

7. The method according to claim 1, wherein the glycoprotein acceptor contains a GlcNAc monosaccharide.

8. The method according to claim 1, wherein the glycoprotein acceptor is a non-fucosylated GlcNAc-acceptor.

9. The method according to claim 1, wherein the glycoprotein acceptor is a glycopeptide, a glycoprotein, an antibody or a fragment thereof.

10. The method according to claim 1, wherein the glycoprotein acceptor is a core fucosylated or non-fucosylated GlcNAC-IgG acceptor or a fragment thereof.

11. The method according to claim 1, wherein the GlcNAC-IgG acceptor is derived from a monoclonal antibody selected from the group consisting of cetuximab, rituximab, muromonab-CD3, abciximab, daclizumab, basiliximab, palivizumab, infliximab, trastuzumab, gemtuzumab ozogamicin, alemtuzumab, ibritumomab tiuxetan, adalimumab, omalizumab, tositumomab, 1-131 tositumomab, efalizumab, bevacizumab, panitumumab, pertuzumab, natalizumab, etanercept, IGN101, volociximab, Anti-CD80 mAb, Anti-CD23 mAb, CAT-3888, CDP-791, eraptuzumab, MDX-010, MDX-060, MDX-070, matuzumab, CP-675,206, CAL, SGN-30, zanolimumab, adecatumumab, oregovomab, nimotuzumab, ABT-874, denosumab, AM 108, AMG 714, fontolizumab, daclizumab, golimumab, CNTO 1275, ocrelizumab, HuMax-CD20, belimumab, epratuzumab, MLN1202, visilizumab, tocilizumab, ocrerlizumab, certolizumab pegol, eculizumab, pexelizumab, abciximab, ranibizimumab.

12. A method for treating cancer, comprising administering to a subject in need thereof an effective amount of a glycoprotein prepared by the method of claim 1.

\* \* \* \* \*